(12) United States Patent
McDonagh et al.

(10) Patent No.: US 9,428,585 B2
(45) Date of Patent: Aug. 30, 2016

(54) HUMANIZED ANTI-CD70 BINDING AGENTS AND USES THEREOF

(71) Applicant: Seattle Genetics, Inc., Bothell, WA (US)

(72) Inventors: Charlotte McDonagh, Seattle, WA (US); Paul Carter, Mercer Island, WA (US)

(73) Assignee: Seattle Genetics, Inc., Bothell, WA (US)

( * ) Notice: Subject to any disclaimer, the term of this patent is extended or adjusted under 35 U.S.C. 154(b) by 278 days.

(21) Appl. No.: 14/053,164

(22) Filed: Oct. 14, 2013

(65) Prior Publication Data

US 2014/0178936 A1   Jun. 26, 2014

Related U.S. Application Data

(60) Division of application No. 13/271,143, filed on Oct. 11, 2011, now Pat. No. 8,562,987, which is a continuation of application No. 11/912,096, filed as application No. PCT/US2006/015145 on Apr. 19, 2006, now Pat. No. 8,067,546.

(60) Provisional application No. 60/673,070, filed on Apr. 19, 2005.

(51) Int. Cl.
| | | |
|---|---|---|
| *C07H 21/00* | (2006.01) | |
| *C07K 16/28* | (2006.01) | |
| *A61K 39/00* | (2006.01) | |

(52) U.S. Cl.
CPC ..... *C07K 16/2875* (2013.01); *A61K 2039/505* (2013.01); *C07K 2317/24* (2013.01); *C07K 2317/732* (2013.01); *C07K 2317/734* (2013.01)

(58) Field of Classification Search
None
See application file for complete search history.

(56) References Cited

U.S. PATENT DOCUMENTS

| | | |
|---|---|---|
| 5,573,924 A | 11/1996 | Beckmann et al. |
| 6,214,345 B1 | 4/2001 | Firestone et al. |
| 6,342,219 B1 | 1/2002 | Thorpe et al. |
| 6,884,869 B2 | 4/2005 | Senter et al. |
| 7,261,892 B2 | 8/2007 | Terrett et al. |
| 7,491,390 B2 | 2/2009 | Law et al. |
| 7,498,298 B2 | 3/2009 | Doronina et al. |
| 7,641,903 B2 | 1/2010 | Law et al. |
| 7,659,241 B2 | 2/2010 | Senter et al. |
| 7,662,387 B2 | 2/2010 | Law et al. |
| 7,829,531 B2 | 11/2010 | Senter et al. |
| 7,851,437 B2 | 12/2010 | Senter et al. |
| 8,067,546 B2 | 11/2011 | McDonagh et al. |
| 8,337,838 B2 | 12/2012 | Law et al. |
| 8,562,987 B2 | 10/2013 | McDonagh et al. |
| 8,609,104 B2 | 12/2013 | Law et al. |
| 8,663,642 B2 | 3/2014 | Law et al. |
| 9,051,372 B2 | 6/2015 | Law et al. |
| 9,051,972 B2 | 6/2015 | Garvey et al. |
| 2003/0083263 A1 | 5/2003 | Doronina et al. |
| 2003/0096743 A1 | 5/2003 | Senter et al. |
| 2003/0105000 A1 | 6/2003 | Pero et al. |
| 2003/0130189 A1 | 7/2003 | Senter et al. |
| 2004/0131612 A1 | 7/2004 | Watkins et al. |
| 2004/0157782 A1 | 8/2004 | Doronina et al. |
| 2004/0180002 A1 | 9/2004 | Young et al. |
| 2005/0106644 A1 | 5/2005 | Cairns et al. |
| 2005/0113308 A1 | 5/2005 | Senter et al. |
| 2005/0118656 A1 | 6/2005 | Terrett |
| 2005/0123547 A1 | 6/2005 | Terrett |
| 2005/0191299 A1 | 9/2005 | Swamy et al. |
| 2005/0238649 A1 | 10/2005 | Doronina et al. |
| 2006/0074008 A1 | 4/2006 | Senter et al. |
| 2006/0083736 A1 | 4/2006 | Law et al. |
| 2006/0233794 A1 | 10/2006 | Law et al. |
| 2007/0292422 A1 | 12/2007 | Law et al. |
| 2008/0025989 A1 | 1/2008 | Law et al. |
| 2008/0138341 A1 | 6/2008 | Law et al. |
| 2008/0138343 A1 | 6/2008 | Law et al. |
| 2008/0226657 A1 | 9/2008 | Doronina et al. |
| 2008/0248051 A1 | 10/2008 | Doronina et al. |
| 2008/0248053 A1 | 10/2008 | Doronina et al. |
| 2009/0047296 A1 | 2/2009 | Doronina et al. |
| 2009/0074772 A1 | 3/2009 | Law et al. |
| 2010/0129362 A1 | 5/2010 | Law et al. |

(Continued)

FOREIGN PATENT DOCUMENTS

| | | |
|---|---|---|
| WO | WO01/94629 A2 | 12/2001 |
| WO | WO02/088172 A2 | 11/2002 |

(Continued)

OTHER PUBLICATIONS

Kettleburough et al, "Humanization of a mouse monoclonal antibody by CDR-grafting: the importance of framework residues on loop conformation," Protein Engineering, 4(7): 773-783, (1991).
U.S. Appl. No. 12/265,451, Non-Final Office Action mailed Sep. 24, 2014.
U.S. Appl. No. 12/265,451, Notice of Allowance mailed Feb. 15, 2015.
U.S. Appl. No. 12/635,607, Non-Final Office Action mailed Jul. 24, 2015.
U.S. Appl. No. 60/449,055, filed Feb. 20, 2003, Law et al.
Adam, et al. "CD70 (TNFSF7) is expressed at high prevalence in renal cell carcinomas and is rapidly internalised on antibody binding" *British J. of Cancer*. 95:298-306, (2006).

(Continued)

*Primary Examiner* — Bradley Duffy
(74) *Attorney, Agent, or Firm* — Alston & Bird LLP

(57) ABSTRACT

Disclosed are CD70 binding agents, such as humanized anti-CD70 antibodies and fragments and derivatives, that exert a cytotoxic, cytostatic or immunomodulatory on CD70 expressing cells, as well as pharmaceutical compositions and kits comprising the antibody, fragment or derivative. Also disclosed are methods for the treatment of CD70-expressing cancers and immunological disorders, comprising administering to a subject the CD70 binding agents or pharmaceutical compositions.

31 Claims, 16 Drawing Sheets

(56) References Cited

U.S. PATENT DOCUMENTS

| | | |
|---|---|---|
| 2010/0150925 A1 | 6/2010 | Law et al. |
| 2010/0158910 A1 | 6/2010 | Law et al. |
| 2010/0183636 A1 | 7/2010 | Law et al. |
| 2012/0294863 A1 | 11/2012 | Law et al. |

FOREIGN PATENT DOCUMENTS

| | | |
|---|---|---|
| WO | WO03/026577 A2 | 4/2003 |
| WO | WO03/046581 A2 | 6/2003 |
| WO | WO2004/010957 A2 | 2/2004 |
| WO | WO2004/073656 A2 | 9/2004 |
| WO | WO2005/081711 A2 | 9/2005 |
| WO | WO2006/044643 A2 | 4/2006 |
| WO | WO2006/113909 A2 | 10/2006 |
| WO | WO2007/038637 A2 | 4/2007 |
| WO | WO2008/074004 A2 | 6/2008 |

OTHER PUBLICATIONS

Agathanggelou et al., "Expression of immune regulatory molecules in Epstein-Barr virus-associated nasopharyngeal carcinomas with prominent lymphoid stroma. Evidence for a functional interaction between epithelial tumor cells and infiltrating lymphoid cells", *Am J.Pathol.*, 147(4):1152-1160, (1995).
Agematsu et al., "B cell subpopulations separated by CD27 and crucial collaboration of CD27+ B cells and helper T cells in immunoglobulin production," *Eur. J. Immunol.*, 27(8):2073-2079, (1997).
Agematsu et al., "Generation of plasma cells from peripheral blood memory B cells: synergistic effect of interleukin-10 and CD27/CD70 interaction," *Blood*, 91(1):173-180, (1998).
Akiba et al., "Critical contribution of OX40 ligand to T helper cell type 2 differentiation in experimental leishmaniasis", *J. Exp. Med.*, 191(2):375-380, (2000).
Baert, et al., "Influence of Immunogenicity on the Long-Term Efficacy of Infliximab in Crohn's Disease", *N. Engl. J. Med.*, 348(7):601-608, (2003).
Bahler et al., "Antigen selection in human lymphomagenesis", *Cancer Res.*, 52(19):5547s-5551s, (1992).
Bahler et al., "Clonal evolution of a follicular lymphoma: evidence for antigen selection," *PNAS*, 89(15):6770-6774, (1992).
Bindon et al., "Human Monoclonal IgG Isotypes Differ in Complement Activating Function at the Level of C4 As Well As C1q", *J. Exp. Med.* 168:127-142, (1988).
Bowman et al., "The cloning of CD70 and its identification as the ligand for CD27", *J. Immunol.*, 152(4):1756-1761, (1994).
Brugnoni et al., "CD70 expression on T-cell subpopulations: study of normal individuals and patients with chronic immune activation", *Immunol. Lett.*, 55(2):99-104, (1997).
Burgess et al., "Possible dissociation of the heparin-binding and mitogenic activities of heparin-binding (acidic fibroblast) growth factor-1 from its receptor-binding activities by site-directed mutagenesis of a single lysine residue", *J. Cell Biol.* 111:2129-2138, (1990).
Carter, P., "Improving the Efficacy of Antibody-Based Cancer Therapies", *Nature Reviews*, (1):118-129, (2001).
Casset, et al., "A peptide mimetic of an anti-CD4 monoclonal antibody of rational design", *Biochem. Biophys. Res.*, 307:198-205, (2003).
Chen et al., "Enhancement and destruction of antibody function by somatic mutation: unequal occurrence is controlled by V gene combinatorial associations", EMBO 14 (12):2784-2794, (1995).
Chen et al., "Potentiation of antitumor immunity by antibody-directed enzyme prodrug therapy", *Int. J. Cancer*, 94(6):850-858, (2001).
Chen et al., "Selection and Analysis of an Optimized Anti-VEGF Antibody: Crystal Structure of an Affinity-matured Fab in Complex with Antigen", *J. Mol. Bio.* 5:293(4):865-881, (1999).
Cohen, "Optimization Of Dose-Time Factors For a Tumor And Multiple Associated Normal Tissues," *Int J Radiat. Oncology Biol. Phys.*, 13:251-258, (1987).
Coleman, PM., "Effects of amino acid sequence changes on antibody-antigen interactions" *Res. Immunology*, 145:33-36, (1994).
De Jong et al., "Regulation of expression of CD27, a T cell-specific member of a novel family of membrane receptors", *J. Immunol.*, 146(8):2488-2494, (1991).
De Pascalis et al., "Grafting of "Abbreviated" Complementarity-Determining Regions Containing Specificity-Determining Residues Essential of Ligand Contact to Engineer a Less Immunogenic Humanized Monoclonal Antibody", *J. Immunol.* 15/169(6):3076-84, (2002).
Den Haan et al., "Identification of a graft versus host disease-associated human minor histocompatibility antigen" *Science*, 268(5216):1476-1480, (1995).
Dillman, R. O., "Monoclonal Antibodies for Treating Cancer", *Ann. Int. Med.*, 111:592-603, (1989).
Doronina et al., "Development of potent monoclonal cancer therapy", *Nature Biotechnology*, 21(7):778-784 (2003) + erratum: 21(8):941, (2003).
Drachman, et al., "SGN-70: Phase 1a Study of a Novel Humanized Antibody Targeting CD70 for the Treatment of Autoimmune Diseases." American College of Rheumatology, Abstract No. 1273, Atlanta, Georgia, Nov. 6-11, (2010) (poster).
Emery, et al., "Humanised monoclonal antibodies for therapeutic applications", *Exp. Opin. Invest. Drugs*, 3(3):241-251, (1994).
EP 1 594 542, European Search Report mailed Mar. 12, 2007.
EP 1 799 262, Supplemental European Search Report mailed Sep. 17, 2009.
EP 1 871 418, Supplementary European Search Report mailed Dec. 7, 2009.
EP 12 166 726, European Search Report mailed Sep. 13, 2012.
EP 6 751 010, European Exam Report mailed Jul. 22, 2011.
EP 98 99 4484, European Search Report mailed Aug. 10, 2009.
Freshney, "Culture of Animal Cells, A Manual of Basic Technique," *Alan R. Liss, Inc.*, 4, (1983).
Giralt et al., "Leukemia relapse after allogeneic bone marrow transplantation: a review", *Blood*, 84(11):3603-3612, (1994).
Goodwin et al., "Molecular and biological characterization of a ligand for CD27 defines a new family of cytokines with homology to tumor necrosis factor", *Cell*, 73(3):447-456, (1993).
Gordon et al., "Humanized Anti-CD70 Auristatin Antibody-Drug Conjugates Show Potent In Vitro Cytotoxicity in Renal Cell Carcinoma Primary Cultures Established from Patient Tumor Isolates," Abstract No. 3733, 97th Annual Meeting of the American Association for Cancer Research, Apr. 1-5, 2006, Washington, D.C.
Gravestein et al., "Cloning and expression of murine CD27: comparison with 4-1BB, another lymphocyte-specific member of the nerve growth factor receptor family", *Eur. J. Immunol.*, 23(4):943-950, (1993).
Gravestein et al., "Novel mAbs reveal potent co-stimulatory activity of murine CD27", *Int. Immunol.*, 7(4):551-557, (1995).
Grewal. "CD70 as a therapeutic target in human malignancies", *Expert Opin. Ther. Targets.* 12(3):341-351, (2008).
Gruss et al., "Pathophysiology of Hodgkin's disease: functional and molecular aspects", *Baillieres Clin. Haematol.*, 9(3):417-446, (1996).
Gura, "Systems for Identifying New Drugs Are Often Faulty", *Science*, 278:1041-1042, (1997).
Harlow et al., "Antibodies, A Laboratory Manual," *Cold Spring Harbor Laboratory*, 140-243, (1998).
Held-Feindt et al., "CD70/CD27 ligand, a member of the TNF family, is expressed in human brain tumors", *Int. J. Cancer*, 98(3):352-356, (2002).
Hintzen et al., "A soluble form of the human T cell differentiation antigen CD27 is released after triggering of the TCR/CD3 complex," *J. Immunol.*, 147(1):29-35, (1991).
Hintzen et al., "CD27: marker and mediator of T-cell activation?", *Immunol. Today*, 15(7):307-311, (1994).
Hintzen et al., "CD70 represents the human ligand for CD 27", *Int. Immunol.*, 6(3):477-480, (1994).

(56) References Cited

OTHER PUBLICATIONS

Hintzen et al., "Characterization of the human CD27 ligand, a novel member of the TNF gene family", *J. Immunol.*, 152(4):1762-1773, (1994).
Hintzen et al., "Engagement of CD27 with its ligand CD70 provides a second signal for T cell activation", *J. Immunol.*, 154(6):2612-2623, (1995).
Hintzen et al., "Regulation of CD27 expression on subsets of mature T-lymphocytes", *J. Immunol.*, 151(5):2426-2435, (1993).
Hishima et al., "CD70 expression in thymic carcinoma", *Am. J. Surg. Pathol.*, 24(5):742-746, (2000).
Holm et al., "Functional mapping and single chain construction of the anti-cytokeratin 8 monoclonal antibody TS1", *Mol. Immunol.*, 44:1075-84, (2007). Epub 2006.
Jacquot et al., "CD154/CD40 and CD70/CD27 interactions have different and sequential functions in T cell-dependent B cell responses: enhancement of plasma cell differentiation by CD27 signaling", *J. Immunol.*, 159(6):2652-2657, (1997).
Janeway et al., "Antigen Recognition by B-Cell and T-Cell Receptors," *Immunobiology*, 5:100-101, (2001).
Jeffrey et al., "Development and properties of beta-glucuronide linkers for monoclonal antibody-drug conjugates", *Bioconjug. Chem.*, 17(3):831-840, (2006). (300EP SR).
Klussman, et al., "Immune Modulation Mediated by the Humanized Anti-CD70 Monoclonal Antibody SGN-70", Experimental Biology, San Diego, California, Apr. 5-9, 2008 (poster).
Knoll et al., "Targeted Therapy of Experimental Renal Cell Carcinoma with a Novel Conjugate of Monoclonal Antibody 138H11 and Calicheamicin ØII", *Cancer Research*, 60:6089-6094, (2000). (300EP SR).
Kobata et al., "CD27-CD70 interactions regulate B-cell activation by T cells," *PNAS*, 92(24):11249-11253, (1995).
Kussie et al., "A Single Engineered Amino Acid Substitution Changes Antibody Fine Specificity", *J. Immunol.* 152:146-152, (1994).
Law et al., "Anti-CD70 Antibody Drug Conjugates Mediate Renal Carcinoma Cell Killing Through Cytotoxic Drug Delivery and Antibody-Dependent Cellular Cytotoxicity (abstract only)", *Proc Amer Assoc Cancer Res.* 46:6143, (2005).
Law et al., "Novel antibody-based therapeutic agents targeting CD70: a potential approach for treating Waldenström's macroglobulinemia", *Clinical Lymphoma & Myeloma* 9(1):90-93, (2009).
Law et al., "Anti-CD70 Auristatin Conjugates with Potent and Selective Activity Against Renal Cell Carcinoma," poster presentation, 4th International Kidney Cancer Symposium, Oct. 21-23, 2005, Chicago, IL.
Law et al., "Lymphocyte Activation Antigen CD70 Expressed by Renal Cell Carcinoma Is a Potential Therapeutic Target for Anti-CD70 Antibody-Drug Conjugates", *Cancer Res.*, 66:(4) 2328-2337, (2006).
Lazar et al., "Transforming growth factor a: mutation of aspartic acid 47 and leucine 48 results in different biological activities", *Mol. Cell. Biol.* 8:1247-1252, (1988).
Lens et al., "Aberrant expression and reverse signaling of CD70 on malignant B cells," *Br. J. Haematol.*, 106(2):491-503, (1999).
Lens et al., "Antigen-presenting cell-derived signals determine expression levels of CD70 on primed T cells", *Immunol.*, 90:38-45, (1997).
Lens et al., "Control of lymphocyte function through CD27-CD70 interactions," *Semin Immunol.*, 10(6):491-499, (1998).
Lens et al., "Phenotype and function of human B cells expressing CD70 (CD27 ligand)", *Eur. J. Immunol.*, 26(12):2964-2971, (1996).
Liu et al., "Chimeric Mouse-Human IGG1 Antibody That Can Mediate Lysis of Cancer Cells", *Proc Natl Acad Sci* 84(1): 3439-3443, (1987).
Locksley et al., "The TNF and TNF receptor superfamilies: integrating mammalian biology", *Cell*, 104(4):487-501, (2001).
MacCallum, et al "Antibody-antigen Interactions: Contact Analysis and Binding Site Topography", *J. Mol. Biol.*, 262:732-745, (1996).

Manocha et al., "Blocking CD27-CD70 Costimulatory Pathway Suppresses Experimental Colitis", *J Immunol* 183: 270-276 (2009).
Maurer et al., "CD27 expression by a distinct subpopulation of human B lymphocytes," *Eur. J. Immunol.*, 20(12):2679-2684, (1990).
McEarchern et al., "Engineered Anti-CD70 Antibody Variants Support Multiple Effector Functions and Exhibit Potent In Vitro and In Vivo Antitumor Activities (abstract only)" , *Proc Amer Assoc Cancer Res.* 46:6142, (2005).
McEarchern et al., "Preclinical characterization of SGN-70, a humanized antibody directed against CD70", *Clin. Cancer Res.*, 14(23):7763-7772, (2008).
McEarchern et al., "SGN-70, A Humanized Anti-CD70 Antibody, Target CD70-Expressing Hematologic Tumors", ASH, Orlando, Florida, Dec. 9-12, 2006 (poster).
McEarchern et al., "Targeting CD70 for the Treatment of Autoimmune Disorders", ACR, San Francisco, California, Oct. 24-29, 2008 (poster).
McEarchern et al., "A Humanized Anti-CD70 Monoclonal Antibody Targets CD70-Expressing Multiple Myeloma," Publication No. 1591, 47th Annual Meeting and Exposition of The American Society of Hematology, Dec. 10-13, 2005, Atlanta, Georgia.
McEarchern et al., "Engineered Anti-CD70 Antibody with Multiple Effector Functions Exhibits in vitro and in vivo Antitumor Activities", *Blood*, 109(3) 1185-1192, (2007).
McEarchern, Julie, "Antitumor Activities of Engineered Anti-CD70 Antibody (h1F6)", *Presentation by Seattle Genetics at Annual Meeting of American Association for Cancer Research* Apr. 16-20:1-15, (2005).
Morrison, "In Vitro Antibodies: Strategies for Production and Application", *Annual Rev Immunol* 10(1): 239-265, (1992).
Nakajima et al., "Involvement of CD70-CD27 interactions in the induction of experimental autoimmune encephalomyelitis", *J. Neuroimmunol.*, 109(2):188-196, (2000).
Nakajima et al., "Roles of IL-4 and IL-12 in the development of lupus in NZB/W F1 mice", *J. Immunol.*, 158(3):1466-1472, (1997).
Oelke et al., "Overexpression of CD70 and Overstimulation of IgG Synthesis by Lupus T Cells and T Cells Treated With DNA Methylation Inhibitors", *Arthritis & Rheumatism*, 50(6):1850-1860, (2004).
Oflazoglu et al. "Blocking of CD27-CD70 Pathway by Anti-CD70 Antibody Ameliorates Joint Disease in Murine Collagen-Induced Arthritis", *J Immunol* 183: 3770-3777, (2009).
Oflazoglu et al., "Inhibition of collagen-induced arthritis by an antibody targeting CD70", FOCIS 2008, Boston, MA, Jun. 7, 2008 (poster).
Oflazoglu et al."In Vivo Characterization of the Mechanism of Action of c1F6, an Anti-CD70 Antibody," Abstract No. 3732, 97th Annual Meeting of the American Association for Cancer Research, Apr. 1-5, 2006, Washington, D.C.
Orengo et al., "Reciprocal expression of CD70 and of its receptor, CD27, in human long term-activated T and natural killer (NK) cells: inverse regulation by cytokines and role in induction of cytotoxicity", *Clin. Exp. Immunol.*, 107(3):608-613, (1997).
Oshima et al., "Characterization of murine CD70 by molecular cloning and mAb", *Int. Immunol.*, 10(4):517-526, (1998).
Paul, Willliam, "Fundamental Immunology", 3rd edition, Laboratory of Immunology National Institute of Allergy and Infectious Diseases 292-295, (1993).
PCT/US04/05247 (published as WO 2004/073656 A3), International Search Report mailed Dec. 22, 2004.
PCT/US04/05247 (published as WO 2004/073656 A3), International Search Report mailed Dec. 22, 2004 (Corrected Version as published on Sep. 1, 2005).
PCT/US05/36994 (published as WO 2006/044643 A3), International Search Report and Written Opinion mailed Jun. 2, 2006.
PCT/US05/36994 (published as WO/2006/044643 A3), Written Opinion of the International Searching Authority mailed Jun. 2, 2006.
PCT/US06/015145 (published as WO 2006/113909 A3), International Search Report and Written Opinion mailed Oct. 16, 2007.
PCT/US06/037753 (published as WO 2007/038637 A3), International Search Report mailed Oct. 4, 2007.

(56) References Cited

OTHER PUBLICATIONS

PCT/US07/087401 (published as WO 2008/074004 A3), International Search Report mailed Oct. 7, 2008.
Peitsch et al., "Comparative molucular modeling of the Fas-ligand and other members of the TNF family", *Mol. Immunol.*, 32(10):761-772, (1995).
Ranheim et al., "Expression of CD27 and its ligand, CD70, on chronic lymphocytic leukemia B cells", *Blood*, 85(12):3556-3565, (1995).
Reff, M. et al., "Future of Monoclonal Antibodies in the Treatment of Hematologic Malignancies," *Cancer Control.* 9(2):152-166, (2002).
Rudikoff et al.,"Single amino acid substitution altering antigen-binding specificity", *PNAS*, 79(6):1979-1983, (1982).
Schnell et al., "Current Strategies of Antibody-Based Treatment in Hodgkin's Disease", *Annals of Oncology*, 13(1):57-66, 2002.
Skolnick et al., "From genes to protein structure and function: novel applications of computational approaches in the genomic era", *Trends in Biotechnology* 18:34-39, (2000).
Smith et al., "A receptor for tumor necrosis factor defines an unusual family of cellular and viral proteins", *Science*, 248(4958):1019-1023, (1990).
Stein et al., "A5 Cluster Report: CDw70", pp. 446-449 from Leucocyte Typing IV White Cell Differentiation Antigens, Knapp, eds., Oxford University Press, 1989.
Sugita et al., "Participation of the CD27 antigen in the regulation of IL-2-activated human natural killer cells", *J. Immunol.*, 149(4):1199-1203, (1992).
Tesselaar et al., "Characterization of murine CD70, the ligand of the TNF receptor family member CD27," *J. Immunol.*, 159(10):4959-4965, (1997).
Tesselaar et al., "Lethal T cell immunodeficiency induced by chronic costimulation via CD27-CD70 interactions", *Nature Immunol* 4(1): 49-54, (2003).
U.S. Appl. No. 10/546,304, Final Office Action mailed May 22, 2008.
U.S. Appl. No. 10/546,304, Non-Final Office Action mailed Feb. 13, 2009.
U.S. Appl. No. 10/546,304, Non-Final Office Action mailed Jul. 23, 2007.
U.S. Appl. No. 10/546,304, Notice of Allowance mailed Sep. 18, 2009.
U.S. Appl. No. 10/546,304, Restriction Requirement mailed Apr. 13, 2007.
U.S. Appl. No. 10/983,340, Office Action mailed Oct. 4, 2007.
U.S. Appl. No. 11/251,173, Non-Final Office Action mailed Apr. 10, 2008.
U.S. Appl. No. 11/251,173, Non-Final Office Action mailed Jul. 10, 2007.
U.S. Appl. No. 11/251,173, Non-Final Office Action mailed Jul. 25, 2008.
U.S. Appl. No. 11/251,173, Notice of Allowance mailed Oct. 23, 2008.
U.S. Appl. No. 11/251,173, Restriction Requirement mailed Mar. 21, 2007.
U.S. Appl. No. 11/735,365, Non-Final Office Action mailed Jan. 13, 2009.
U.S. Appl. No. 11/735,365, Non-Final Office Action mailed Apr. 30, 2009.
U.S. Appl. No. 11/735,365, Notice of Allowance mailed Aug. 18, 2009.
U.S. Appl. No. 11/735,365, Restriction Requirement mailed Sep. 30, 2008.
U.S. Appl. No. 11/735,376, Non Final Office Action mailed May 26, 2010.
U.S. Appl. No. 11/735,376, Non Final Office Action mailed Aug. 3, 2009.
U.S. Appl. No. 11/735,376, Notice of Abandonment mailed Dec. 27, 2010.
U.S. Appl. No. 11/735,376, Restriction Requirement mailed Nov. 5, 2008.
U.S. Appl. No. 11/912,096, Non Final Office Action mailed Feb. 7, 2011.
U.S. Appl. No. 11/912,096, Notice of Allowance mailed Jul. 11, 2011.
U.S. Appl. No. 11/912,096, Restriction Requirement mailed Nov. 12, 2010.
U.S. Appl. No. 12/265,451, Final Office Action mailed Apr. 1, 2011.
U.S. Appl. No. 12/265,451, Final Office Action mailed Dec. 16, 2013.
U.S. Appl. No. 12/265,451, Non-Final Office Action mailed Jul. 9, 2013.
U.S. Appl. No. 12/265,451, Non-Final Office Action mailed Jul. 21, 2010.
U.S. Appl. No. 12/265,451, Restriction Requirement mailed Apr. 13, 2010.
U.S. Appl. No. 12/370,151, Non-Final Office Action mailed Jan. 19, 2011.
U.S. Appl. No. 12/370,151, Notice of Allowance mailed Apr. 3, 2012.
U.S. Appl. No. 12/370,151, Notice of Allowance mailed Jun. 21, 2011.
U.S. Appl. No. 12/370,151, Notice of Allowance mailed Aug. 23, 2012.
U.S. Appl. No. 12/467,182, Non Final Office Action mailed Aug. 23, 2011.
U.S. Appl. No. 12/467,182, Restriction Requirement mailed Apr. 21, 2001.
U.S. Appl. No. 12/635,571, Final Office Action mailed Mar. 7, 2012.
U.S. Appl. No. 12/635,571, Non Final Office Action mailed Oct. 13, 2011.
U.S. Appl. No. 12/635,607, Advisory Action mailed Aug. 28, 2013.
U.S. Appl. No. 12/635,607, Final Office Action mailed Apr. 18, 2013.
U.S. Appl. No. 12/635,607, Non Final Office Action mailed May 7, 2012.
U.S. Appl. No. 12/635,607, Non Final Office Action mailed Oct. 11, 2011.
U.S. Appl. No. 12/635,607, Non Final Office Action mailed Oct. 18, 2012.
U.S. Appl. No. 12/891,716, Final Office Action mailed Apr. 26, 2013.
U.S. Appl. No. 12/891,716, Non-Final Office Action mailed Dec. 14, 2012.
U.S. Appl. No. 12/891,716, Notice of Allowance mailed Oct. 17, 2013.
U.S. Appl. No. 13/271,143, Non-Final Office Action mailed Feb. 28, 2013.
U.S. Appl. No. 13/271,143, Notice of Allowance mailed Apr. 24, 2013.
U.S. Appl. No. 13/271,143, Restriction Requirement mailed Dec. 10, 2012.
U.S. Appl. No. 13/491,475, Non Final Office Action mailed Aug. 2, 2012.
U.S. Appl. No. 13/491,475, Notice of Allowance mailed Jan. 22, 2013.
U.S. Appl. No. 13/566,827, Final Office Action mailed Jun. 19, 2013.
U.S. Appl. No. 13/566,827, Non-Final Office Action mailed Feb. 1, 2013.
Vajdos et al. "Comprehensive Functional Maps of the Antigen-binding Site of an Anti-ErbB2 Antibody Obtained with Shotgun Scanning Mutagenesis", *J. Mol. Biol.*, 5;320(2):415-428, (2002).
Van Lier et al., "Tissue distribution and biochemical and functional properties of Tp55 (CD27), a novel T cell differentiation antigen", *J. Immunol.*, 139(5):1589-1596, (1987).
White, "Antibody-Targeted Immunotherapy For Treatment of Malignancy", *Annual Review of Medicine*; 52:125-145, (2001).
Winkler et al., "Changing the Antigen Binding Specificity by Single Point Mutations of an Anti-p24 (HIV-1 antibody", *J. Immunol.*, 165(16):4505-4514, (2000).

(56) References Cited

OTHER PUBLICATIONS

Wischhusen et al., "Identification of CD70-mediated apoptosis of immune effector cells as a novel immune escape pathway of human glioblastoma", *Cancer Res.*, 6299):2592-2599, (2002).

Witzig et al., "Radioimmunotherapy for patients with relapsed B-cell non-Hodgkin lymphoma", *Cancer Chemother. Pharmacol.*, 48(suppl. 1):S91-S95, (2001).

Wu et al., "Humanization of a Murine Monoclonal Antibody by Simultaneous Optimization of Framework and CDR Residues", *J. Mol. Biol.*, 19:294(1):151-62, (1999).

Wu et al., "Simultaneous Humanization and Affinity Optimization of Monoclonal Antibodies", *Methods in Mol. Biol.*, 207:197-212,(2003).

Zips et al., "New Anticancer Agents: In Vitro and In Vivo Evaluation", *In Vivo* 19:1-8, (2005).

Figure 1

```
                                                    46
                                                    |
1F6 mV_H   (1)   QIQLVQSGPEVKKPGETVKISCKASGYTFTNYGMNWVKQAPGKGLKWMGW
1F6 hV_HE  (1)   .V..A..........AS..V.............R...Q..E........
1F6 hV_HJ  (1)   .V..A..........AS..V.............R...Q..K........
V_H1-2     (1)   .V..A..........AS..V.........G.Y.H...R...Q..E....
                                                                  <

1F6 mV_H   (51)  INTYTGEPTYADAFKGREAFSLETSASTAYLQINNLKNEDTATYFCARDY
1F6 hV_HE  (51)  .................VTMTRD..I....MELSR.RSD....V..Y..
1F6 hV_HJ  (51)  .................VTMTRD..I....MELSR.RSD....V..Y..
V_H1-2     (51)  .PNS.GTN.....QKFQ.VTMTRD..I....MELSR.RSD....V..Y..
                                                                   <

1F6 mV_H   (121) GDYGMDYWGQGTSVTVSS
1F6 hV_HE  (111) .........T........
1F6 hV_HJ  (111) .........T........
J_H6             ..Y...V..T........
```

Figure 2

```
                   QIQLVQSGPEVKKPGETVKISCKASGYTFTNYGMNWVKQAPGKGLKWMGW
1F6 mVH    (1)     ...............................R......Q..E....
1F6 hVHH   (1)     .V....A...............AS.V.....................
1F6 hVHM   (1)     .V....A...............AS.V.....R......Q..K.....
VH1-18     (1)     .V....A...............AS.V.....R......Q..E.....

67  71                    80 82A
                        |   |                     |  |
                   INTYTGEPTYADAFKGRFAFSLETSASTAYLQINNLKNEDTATYFCARDY
1F6 mVH   (51)     ................FAFSID..T......LQINS.RSD.....V.Y.
1F6 hVHH  (51)     .SA.N.NIN......QKLQFAFSID..T......MELRS.RSD.....V.Y.
1F6 hVHM  (51)     ..........S.IS.FAFSID..T......MELRS.RSD.....V.Y.
VH1-18    (51)     ................VTMTTD..T................Y

GDYGMDYWGQGTSVTVSS
1F6 mVH   (101)    ..................
1F6 hVHH  (101)    ...........T......
1F6 hVHM  (101)    YY.........T......
JH6                ....V......T......
```

Figure 3

```
1F6 mVL    (1)   DIVLTQSPASLAVSLGQRATISCRASKSVSTSG--YSFMHWYQQKPGQPP
1F6 hVLA   (1)   .....D.........E......N............... ........
B3         (1)   .....D.........E......N.KS.Q..LY.SNNKNYLA.......
                                        <                         <

1F6 mVL   (49)   KLLIYLASNLESGVPARFSGSGSGTDFTLNIHPVEEEDAATYYCQHSREV
1F6 hVLA  (49)   ..........D..........T.SSIQA..V.V........
B3        (51)   W..TR........D..........T.SSIQA..V.V....QYYST
                                                                  <

1F6 mVL   (99)   PWTFGGGTKLEIKR
1F6 hVLA  (99)   .....Q....V....
B3/JK-1  (101)   .....Q....V....
```

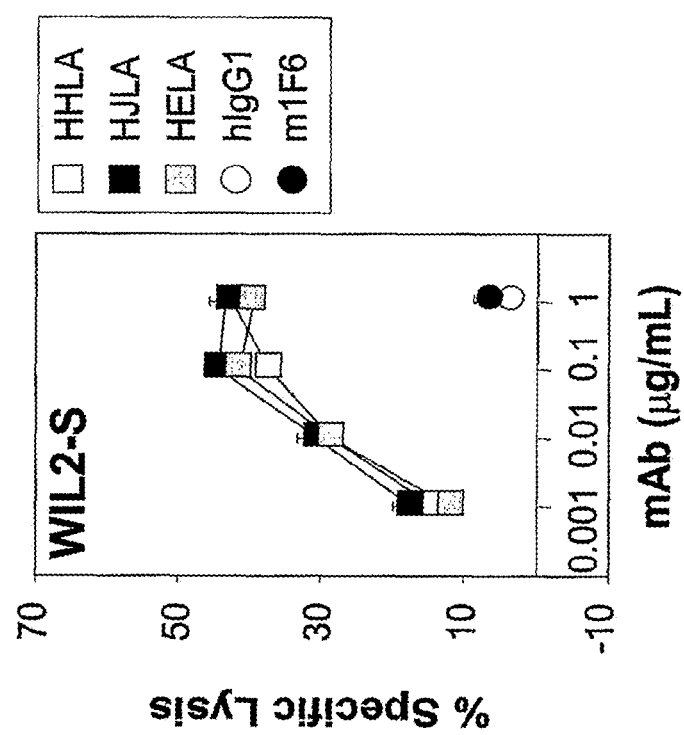

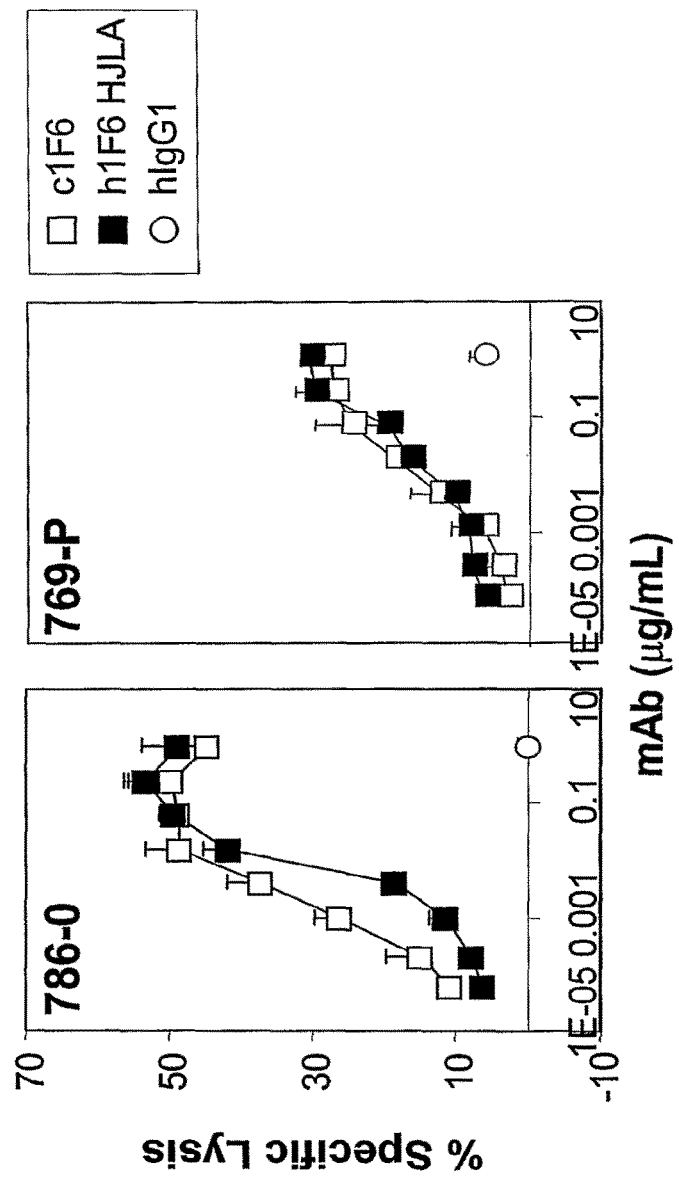

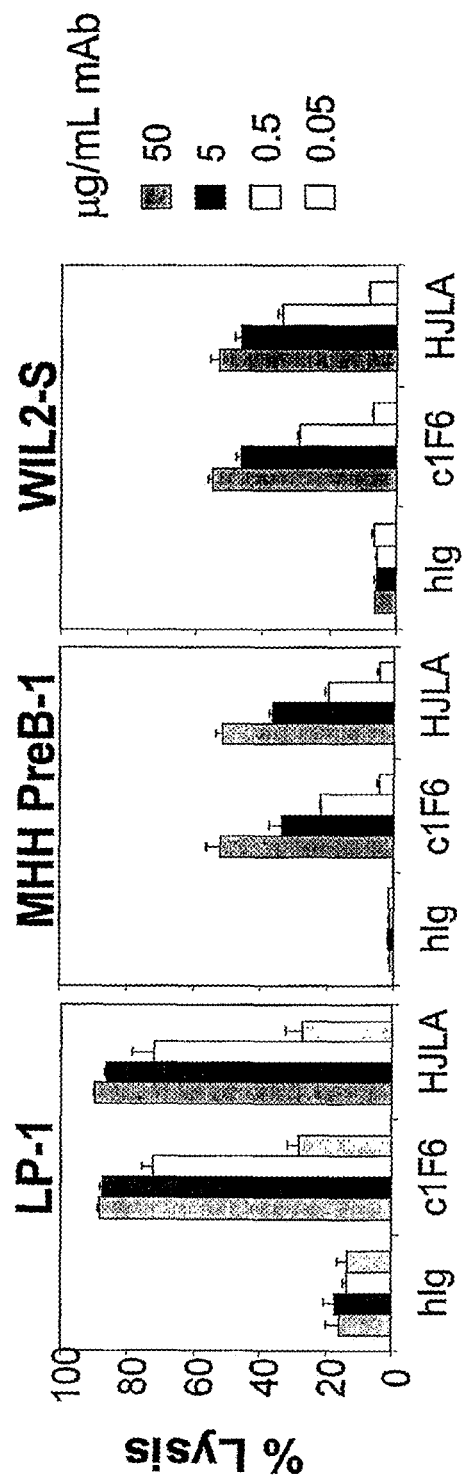

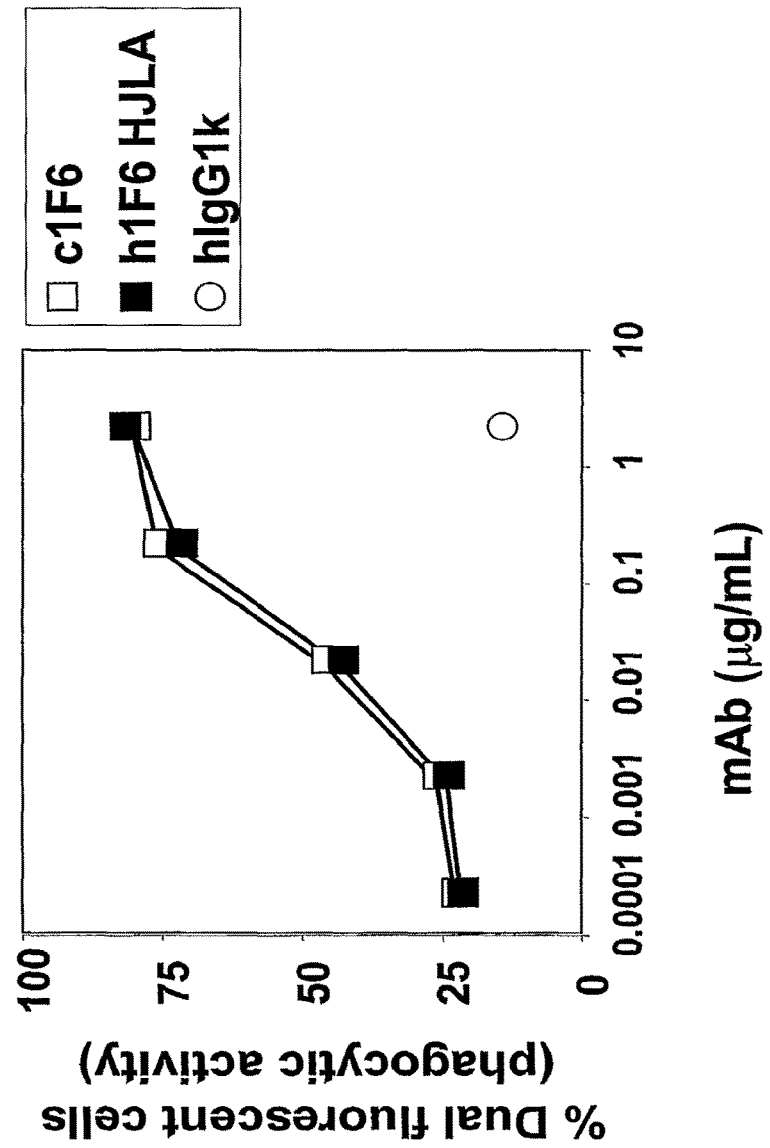

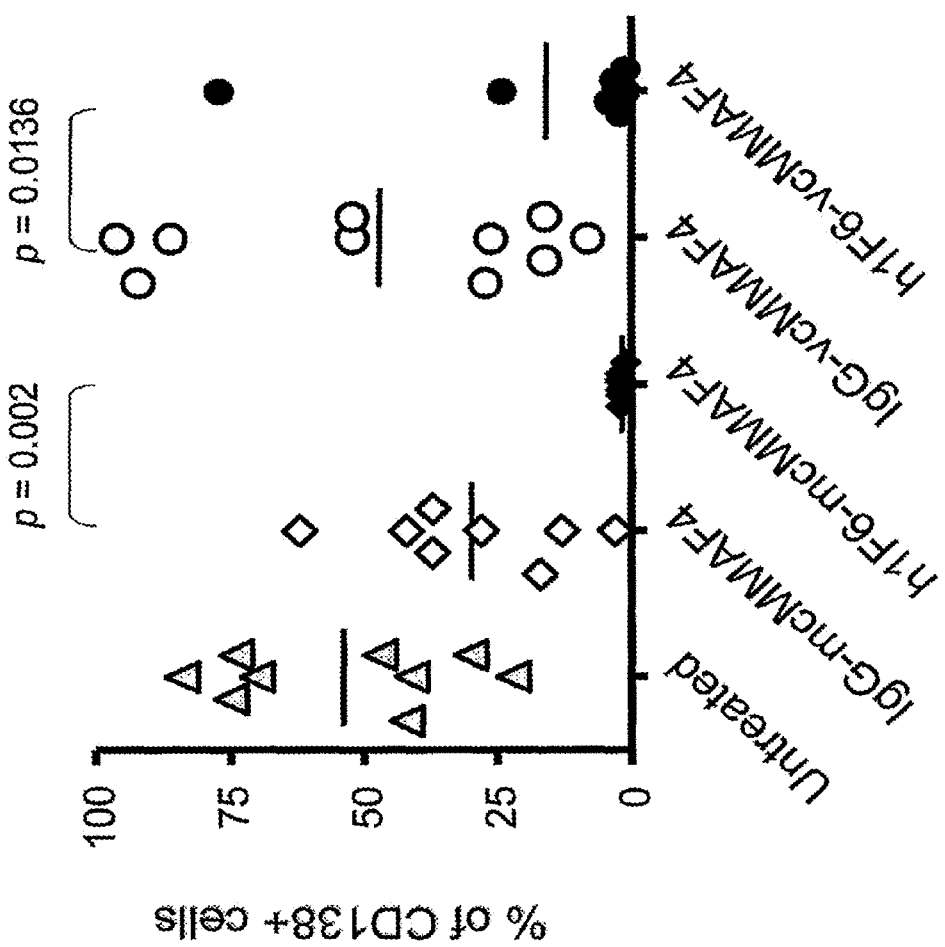

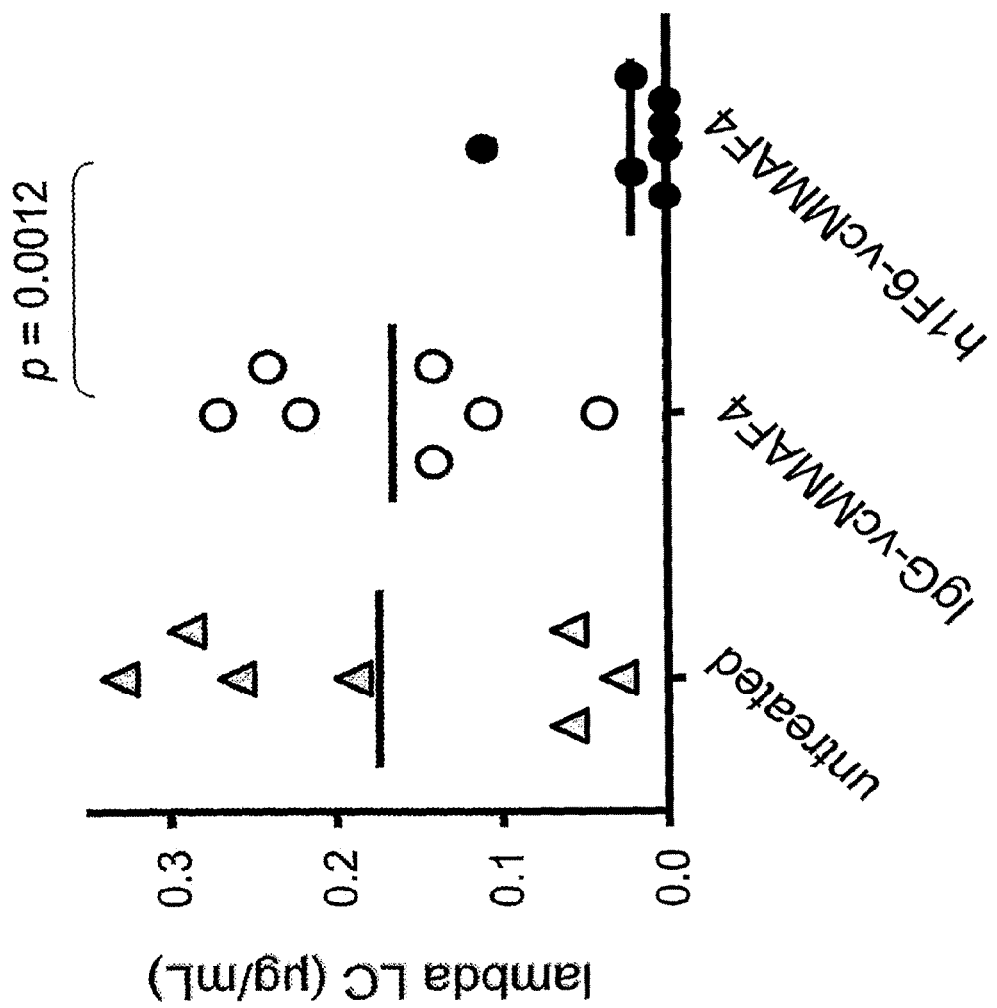

HUMANIZED ANTI-CD70 BINDING AGENTS AND USES THEREOF

RELATED APPLICATIONS

This application is a division of U.S. application Ser. No. 13/271,143, filed Oct. 11, 2011, now U.S. Pat. No. 8,562,987, which is a continuation of U.S. application Ser. No. 11/912,096, filed Oct. 23, 2008, now U.S. Pat. No. 8,067,546, which is a U.S. National Stage Application under 35 USC 371 of International Application No. PCT/US2006/015145, filed Apr. 19, 2006, which claims the benefit under 35 USC 119(e) of U.S. Provisional Patent Application No. 60/673,070, filed Apr. 19, 2005, each of which is incorporated by reference herein in its entirety.

REFERENCE TO A SEQUENCE LISTING

This application includes an electronic sequence listing in a file named "437966-Sequence.txt", created on Oct. 14, 2013 and containing 52,029 bytes, which is hereby incorporated by reference in its entirety for all purposes.

BACKGROUND

CD70 is a member of the tumor necrosis factor (TNF) family of cell membrane-bound and secreted molecules that are expressed by a variety of normal and malignant cell types. The primary amino acid (AA) sequence of CD70 predicts a transmembrane type II protein with its carboxyl terminus exposed to the outside of cells and its amino terminus found in the cytosolic side of the plasma membrane (Bowman et al., 1994, *J. Immunol.* 152:1756-61; Goodwin et al., 1993, *Cell* 73:447-56). Human CD70 is composed of a 20 AA cytoplasmic domain, an 18 AA transmembrane domain, and a 155 AA extracytoplasmic domain with two potential N-linked glycosylation sites (Bowman et al., supra; Goodwin et al., supra). Specific immunoprecipitation of radioisotope-labeled CD70-expressing cells by anti-CD70 antibodies yields polypeptides of 29 and 50 kDa (Goodwin et al., supra; Hintzen et al., 1994, *J. Immunol.* 152:1762-73). Based on its homology to TNF-alpha and TNF-beta, especially in structural strands C, D, H and I, a trimeric structure is predicted for CD70 (Petsch et al., 1995, *Mol. Immunol.* 32:761-72).

Original immunohistological studies revealed that CD70 is expressed on germinal center B cells and rare T cells in tonsils, skin, and gut (Hintzen et al., 1994, *Int. Immunol.* 6:477-80). Subsequently, CD70 was reported to be expressed on the cell surface of recently antigen-activated T and B lymphocytes, and its expression wanes after the removal of antigenic stimulation (Lens et al., 1996, *Eur. J. Immunol.* 26:2964-71; Lens et al., 1997, *Immunology* 90:38-45). Within the lymphoid system, activated natural killer cells (Orengo et al., 1997, *Clin. Exp. Immunol.* 107:608-13) and mouse mature peripheral dendritic cells (Akiba et al., 2000, *J. Exp. Med.* 191:375-80) also express CD70. In non-lymphoid lineages, CD70 has been detected on thymic medullar epithelial cells (Hintzen et al., 1994, supra; Hishima et al., 2000, *Am. J. Surg. Pathol.* 24:742-46).

CD70 is not expressed on normal non-hematopoietic cells. CD70 expression is mostly restricted to recently antigen-activated T and B cells under physiological conditions, and its expression is down-regulated when antigenic stimulation ceases. Evidence from animal models suggests that CD70 may contribute to immunological disorders such as, e.g., rheumatoid arthritis (Brugnoni et al., 1997, *Immunol. Lett.* 55:99-104), psoriatic arthritis (Brugnoni et al., 1997, *Immunol. Lett.* 55:99-104), and lupus (Oelke et al., 2004, *Arthritis Rheum.* 50:1850-60). In addition to its potential role in inflammatory responses, CD70 is also expressed on a variety of transformed cells including lymphoma B cells, Hodgkin's and Reed-Sternberg cells, malignant cells of neural origin, and a number of carcinomas.

Accordingly, there is a need for anti-CD70 antibodies and other CD70 binding agents that can exert a clinically useful cytotoxic, cytostatic, or immunomodulatory effect on CD70-expressing cells, particularly without exerting undesirable effects on non-CD70-expressing cells. Such compounds would be useful therapeutic agents against cancers that express CD70 or immune disorders that are mediated by CD70-expressing cells. (The recitation of any reference in this application is not an admission that the reference is prior art to this application.)

BRIEF SUMMARY

The present invention provides CD70 antibodies and related CD70 binding agents and methods relating to the use of such binding agents for the prophylaxis or treatment of CD70-expressing cancers and immunological disorders where CD70-expressing cells are present. The CD70 binding agent, alone or in combination with a therapeutic agent, exerts a cytotoxic, cytostatic, and/or immunomodulatory effect on CD70-expressing cells.

In an aspect, CD70 binding agents are provided. The CD70 binding agent can be, for example, an antibody. In some embodiments, the binding agent includes at least one effector domain mediating at least an ADCC, ADCP or CDC response in the subject. In some embodiments, the binding agent exerts a cytostatic, cytotoxic or immunomodulatory effect in the absence of conjugation to a therapeutic agent. In some embodiments, the binding agent is conjugated to a therapeutic agent that exerts a cytotoxic, cytostatic or immunodulatory effect. The antibody can compete for binding to CD70 with monoclonal antibody 1F6 or 2F2.

In another aspect, a method of treating a CD70-expressing cancer in a subject is provided. The method generally includes administering to the subject an effective amount of a CD70 binding agent. In some embodiments, the binding agent includes at least one effector domain mediating at least an ADCC, ADCP or CDC response in the subject. In some embodiments, the binding agent exerts a cytostatic, cytotoxic or immunomodulatory effect in the absence of conjugation to a therapeutic agent. In some embodiments, the binding agent is conjugated to a therapeutic agent that exerts a cytotoxic, cytostatic or immunodulatory effect.

The CD70-binding agent can be, for example, an antibody. The antibody can include, for example, an effector domain of a human IgM or IgG antibody. The IgG antibody can be, for example, a human IgG1 or IgG3 subtype. In some embodiments, the antibody includes a human constant region. In some embodiments, the CD70 binding agent competes for binding to CD70 with monoclonal antibody 1F6 or 2F2. In other embodiments, the antibody is a humanized 1F6. In other embodiments, the antibody is a humanized 2F2. The antibody can be, for example, monovalent, divalent or multivalent.

The CD70-expressing cancer can be, a kidney tumor, a B cell lymphoma, a colon carcinoma, Hodgkin's Disease, multiple myeloma, Waldenström's macroglobulinemia, non-Hodgkin's lymphoma, a mantle cell lymphoma, chronic lymphocytic leukemia, acute lymphocytic leukemia, a nasopharyngeal carcinoma, brain tumor or a thymic carcinoma. The kidney tumor can be, for example, a renal cell carcinoma. The brain tumor can be, for example, a glioma, a glioblastoma, an astrocytoma or a meningioma. The subject can be, for example, a mammal, such as a human being.

In another aspect, a method for treating an immunological disorder is provided. The method includes administering to a subject an effective amount of a CD70 binding agent. In some embodiments, the binding agent includes at least one effector domain mediating at least an ADCC, ADCP or CDC response in the subject. In some embodiments, the binding agent exerts a cytostatic, cytotoxic or immunomodulatory effect in the absence of conjugation to a therapeutic agent. In some embodiments, the binding agent is conjugated to a therapeutic agent that exerts a cytotoxic, cytostatic or immunomodulatory effect. The CD70 binding agent can be, for example, an antibody. The antibody can include, for example, an effector domain of a human IgM or IgG antibody. The IgG antibody can be, for example, a human $IgG_1$ or $IgG_3$ subtype. In some embodiments, the antibody includes a human constant region.

The immunological disorder can be, for example, a T cell-mediated immunological disorder. In some embodiments, the T cell mediated immunological disorder comprises activated T cells expressing CD70. In some embodiments, resting T cells are not substantially depleted by administration of the antibody-drug conjugate. The T cell-mediated immunological disorder also can be, for example, rheumatoid arthritis, psoriatic arthritis, systemic lupus erythematosus (SLE), Type I diabetes, asthma, atopic dermatitis, allergic rhinitis, thrombocytopenic purpura, multiple sclerosis, psoriasis, Sjögren's syndrome, Hashimoto's thyroiditis, Graves' disease, primary biliary cirrhosis, Wegener's granulomatosis, tuberculosis, or graft versus host disease. In other embodiments, the immunological disorder is an activated B-lymphocyte disorder. The subject can be, for example, a mammal, such as a human being.

In a related aspect, also provided is a pharmaceutical composition for the treatment of a CD70-expressing cancer or an immunological disorder. The composition includes a CD70 binding agent and at least one pharmaceutically compatible ingredient. Further provided is a pharmaceutical kit including a container including a CD70 binding agent, wherein the agent is lyophilized, and a second container comprising a pharmaceutically acceptable diluent.

The present invention may be more fully understood by reference to the following detailed description of the invention, non-limiting examples of specific embodiments of the invention and the appended figures and sequence listing.

BRIEF DESCRIPTION OF THE DRAWINGS

FIG. 1 is an alignment of humanized 1F6 $V_H$ humanized variants $hV_HE$ (SEQ ID NO:6) and $hV_HJ$ (SEQ ID NO:14) with 1F6 $mV_H$ (residues 20-137 of SEQ ID NO:2) and human germline $V_H$ exon $V_H$1-2 and $J_H$ exon JH6 (collectively SEQ ID NO:31). In the alignment, a <•> indicates that the amino acid is identical to the murine residue. The highlighted lysine residue (K) at H46 of $hV_HJ$ indicates a back mutation to the murine residue. Underlined amino acid residues indicate positions in CDR1 and CDR2 according to the Kabat definition, whereas boxed residues indicate positions in the corresponding CDR identified by the Chothia definition. A < >, as at positions 37, 39, 45, 47, 95 and 97, indicates a residue in involved in the $V_H/V_L$ interface.

FIG. 2 is an alignment of humanized 1F6 $V_H$ humanized variants $hV_HH$ (SEQ ID NO:10) and $hV_HM$ (SEQ ID NO:18) with 1F6 $mV_H$ (residues 20-137 of SEQ ID NO:2) and human germline $V_H$ exon $V_H$1-18 and $J_H$ exon JH6 (collectively SEQ ID NO:32). In the alignment, a <•> indicates that the amino acid is identical to the murine residue. The highlighted residues at H46, H67, H68, H69, H70, and H71 of $hV_HM$ indicate back mutations to the murine residues. Similarly, the highlighted residues at H67, H68, H69, H70, H71, H80, H81, H82, and H82A of $hV_HH$ indicate back mutations to the murine residues. Underlined amino acid residues indicate positions in CDR1, CDR2, and CDR3 according to the Kabat definition, whereas boxed residues indicate positions in the corresponding CDR identified by the Chothia definition. A < >, as at positions 37, 39, 45, 47, 98, and 100 indicates a residue in involved in the $V_H/V_L$ interface.

FIG. 3 is an alignment of humanized 1F6 $V_L$ variant $hV_LA$ (SEQ ID NO:24) with 1F6 $mV_L$ (residues 21-132 of SEQ ID NO:22) and human germline $V_\kappa$ exon B3 and $J_\kappa$ exon Jκ-1 (collectively SEQ ID NO:33). In the alignment, a <•> indicates that the amino acid is identical to the murine residue. Underlined amino acid residues indicate positions in CDR1, CDR2, and CDR3 according to the Kabat definition, whereas boxed residues indicate positions in the corresponding CDR identified by the Chothia definition. A < >, as at positions 42, 44, 50, 52, and 93, indicates a residue in involved in the $V_H/V_L$ interface.

FIGS. 4A and 4B show that humanized 1F6 anti-CD70 antibodies mediate antibody-dependent cellular cytotoxicity (ADCC). $Na_2^{51}CrO_4$-labeled target cells (WIL2-S B lymphoblastoid cells, 786-O renal cell carcinoma cells, and 769-P renal cell carcinoma cells) were coated with antibody and incubated with peripheral blood mononuclear cells (PBMC) at an effector to target ratio of 10 $CD16^+$ (FcγIII receptor) cells to 1 target cell. After 4 hours, the supernatants from lysed cells were measured on a scintillation counter. The percent specific lysis was calculated as {(test sample cpm–spontaneous cpm)±(total cpm–spontaneous cpm)}× 100. Points represent the mean±standard deviation of triplicate samples. FIG. 4A shows the ADCC activity mediated by humanized 1F6 variants HHLA, HJLA and HELA compared to non-binding antibody control $hIgG_1$ and murine 1F6 antibody. FIG. 4B shows antibody-directed lysis of renal cell carcinoma cell lines mediated by chimeric 1F6 and humanized 1F6 variant HJLA, and $hIgG_1$.

FIG. 5 shows that humanized 1F6 anti-CD70 variant HJLA mediates complement-dependent cellular cytotoxicity (CDC). LP-1, MHH PreB-1 and WIL-S target cells were mixed with chimeric 1F6, humanized 1F6 (HJLA) or non-binding human Ig in the presence of human serum as a source of complement. After 2 hours at 37° C., propidium iodide was added to determine cell viability as measured by flow cytometry, and the amount of lytic activity was calculated. Bars represent the mean±standard deviation of triplicate samples.

FIG. 6 shows that humanized 1F6 anti-CD70 antibodies mediate antibody-dependent cellular phagocytosis (ADCP). 786-O $CD70^+$ renal cell carcinoma target cells were labeled with a red fluorescent cell membrane dye (PKH26, Sigma-Aldrich, Inc., St. Louis, Mo.) and then coated with chimeric 1F6, humanized 1F6 (HJLA) or non-binding human Ig for 30 minutes on ice. Labeled, antibody-treated target cells were mixed with monocyte-derived macrophages at a ratio of 1 macrophage to 4 target cells for 1 hour at 37° C. Macrophages were stained with an Alexa Fluor® 488 (Molecular Probes, Inc., Eugene, Oreg.) anti-CD11b antibody and the percent phagocytic activity was determined by the percentage of macrophages exhibiting dual fluorescence when analyzed by flow cytometry.

DETAILED DESCRIPTION

Figure 7:
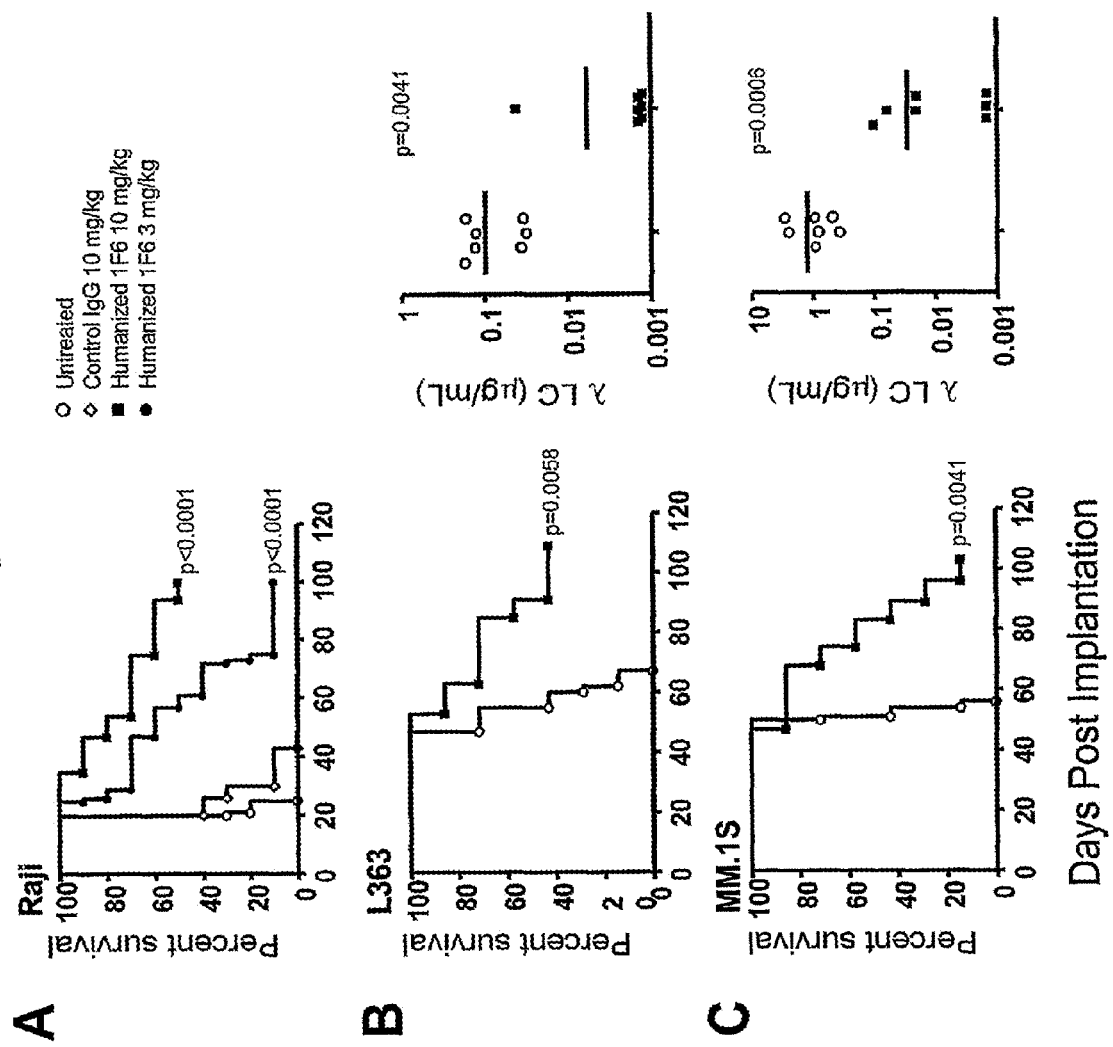
FIG. 7 shows humanized 1F6 anti-CD70 antibody prolongs survival of mice in xenograft models of disseminated lymphoma and multiple myeloma. (A) Survival of mice injected with Raji cells and treated with humanized 1F6 antibody or control non-binding antibody. Treatment was initiated one day after tumor cell injection and was administered by intraperitoneal injection every four days for a total of six doses (n=10 per group). (B, C, left panels) Survival of mice injected with L363- or MM.1S-cells and treated with humanized 1F6 starting one day after cell implant. The antibody was administered by intravenous injection once weekly for a total of five doses. Mice were monitored twice weekly and were euthanized upon manifestation of disease (n=7 per group). (B, C, right panels) Analysis of λ light chain concentrations in sera collected from mice injected with L363- or MM.1S-cells. Samples were collected on days 35 and 42 post tumor injection, respectively. In all studies, p values given are between humanized 1F6-treated groups and the untreated group.

The present invention provides CD70 binding agents and methods for using such binding agents for the prophylaxis or treatment of CD70-expressing cancers and immunological disorders. The CD70 binding agent specifically binds to CD70 (e.g., the extracellular domain). The binding agent may include at least one effector domain mediating an ADCC, ADCP and/or CDC response. The binding agent may exert a cytostatic, cytotoxic or immunomodulatory effect in the absence of conjugation to a therapeutic agent. The binding agent may be conjugated to a therapeutic agent that exerts a cytotoxic, cytostatic or immunodulatory effect.

In one aspect, the compositions and methods relate to CD70 binding agents, such as antibodies and antibody derivatives. The anti-CD70 antibody can be a monoclonal, chimeric or humanized antibody, or a fragment or derivative thereof. In some embodiments, the anti-CD70 antibody includes an antibody constant region or domain. The antibody constant region or domain can be, for example, of the IgG subtype. In an exemplary embodiment, the anti-CD70 antibody, fragment or derivatives thereof, competes with the murine monoclonal antibody (mAb) 1F6 or 2F2 for binding to CD70 and comprises human antibody constant region sequences. In another exemplary embodiment, the anti-CD70 antibody, or fragment or derivative thereof, has an effector domain (e.g., an Fc portion) that can interact with effector cells or complement to mediate a cytotoxic, cytostatic, and/or immunomodulatory effect that results in the depletion or inhibition of the proliferation of CD70-expressing cells. In another exemplary embodiment, the anti-CD70 antibody lacks effector function. In another exemplary embodiment, the anti-CD70 antibody is conjugated to a therapeutic agent.

Also included are kits and articles of manufacture comprising a CD70 binding agent (e.g., a humanized anti-CD70 antibody).

For clarity of disclosure, and not by way of limitation, the detailed description of the invention is divided into the subsections which follow.

I. DEFINITIONS AND ABBREVIATIONS

Unless defined otherwise, all technical and scientific terms used herein have the same meaning as commonly understood by one of ordinary skill in the art pertinent to the methods and compositions described. When trade names are used herein, applicants intend to independently include the trade name product formulation, the generic drug, and the active pharmaceutical ingredient(s) of the trade name product. As used herein, the following terms and phrases have the meanings ascribed to them unless specified otherwise.

The terms "CD70 binding agent" and "anti-CD70 binding agent" as used herein means an anti-CD70 antibody, a derivative or a fragment of an anti-CD70 antibody, or other agent that binds to CD70 and comprises at least one CDR or variable region of a CD70 binding antibody, or a derivative thereof.

The term "specifically binds" means that the binding agent will react, in a highly selective manner, with its corresponding antigen and not with the multitude of other antigens (e.g., non-CD70 molecules).

As used herein, the term "functional" in the context of a CD70 binding agent indicates that the binding agent is capable of binding to CD70.

The terms "inhibit" or "inhibition of" as used herein means to reduce by a measurable amount, or to prevent entirely.

The term "deplete" in the context of the effect of a CD70-binding agent on CD70-expressing cells refers to a reduction in the number of or elimination of the CD70-expressing cells.

"Intact antibodies" and "intact immunoglobulins" are defined herein as heterotetrameric glycoproteins, typically of about 150,000 daltons, composed of two identical light (L) chain and two identical heavy (H) chains. Each light chain is covalently linked to a heavy chain by a disulfide bond to form a heterodimer. The heterotetramer is formed by covalent disulfide linkage between the two identical heavy chains of such heterodimers. Although the light and heavy chains are linked together by a disulfide bond, the number of disulfide linkages between the two heavy chains varies by immunoglobulin (Ig) isotype. Each heavy and light chain also has regularly spaced intrachain disulfide bridges. Each heavy chain has at the amino-terminus a variable domain ($V_H$), followed by three or four constant domains ($C_H1$, $C_H2$, $C_H3$, and/or $C_H4$), as well as a hinge (J) region between $C_H1$ and $C_H2$. Each light chain has two domains, an amino-terminal variable domain ($V_L$) and a carboxy-terminal constant domain ($C_L$). The $V_L$ domain associates non-covalently with the $V_H$ domain, whereas the $C_L$ domain is commonly covalently linked to the $C_H1$ domain via a disulfide bond. Particular amino acid residues are believed to form an interface between the light and heavy chain variable domains (Chothia et al., 1985, *J. Mol. Biol.* 186: 651-663).

The term "hypervariable" refers to certain sequences within the variable domains that differ extensively in sequence among antibodies and contain residues that are directly involved in the binding and specificity of each particular antibody for its specific antigenic determinant. Hypervariability, both in the light chain and the heavy chain variable domains, is concentrated in three segments known as complementarity determining regions (CDRs) or hypervariable loops (HVLs). CDRs are defined by sequence comparison in Kabat et al., 1991, In: Sequences of Proteins of Immunological Interest, 5th Ed. Public Health Service, National Institutes of Health, Bethesda, M.D., whereas HVLs are structurally defined according to the three-dimensional structure of the variable domain, as described by Chothia and Lesk, 1987, *J. Mol. Biol.* 196:901-917. Where these two methods result in slightly different identifications of a CDR, the structural definition is preferred. As defined by Kabat (see Kabat et al., "Sequences of proteins of immunological interest, 5th ed., Pub. No. 91-3242, U.S. Dept. Health & Human Services, NIH, Bethesda, M.D., 1991), CDR-L1 is positioned at about residues 24-34, CDR-L2, at about residues 50-56, and CDR-L3, at about residues and 89-97 in the light chain variable domain and at about 31-35 in CDR-H1, at about 50-65 in CDR-H2, and at about 95-102 in CDR-H3 in the heavy chain variable domain.

The three CDRs within each of the heavy and light chains are separated by framework regions (FRs), which contain sequences that tend to be less variable. From the amino terminus to the carboxy terminus of the heavy and light chain variable domains, the FRs and CDRs are arranged in the order: FR1, CDR1, FR2, CDR2, FR3, CDR3, and FR4. The largely β-sheet configuration of the FRs brings the CDRs within each of the chains to close proximity to each other as well as to the CDRs from the other chain. The resulting conformation contributes to the antigen binding site (see Kabat et al., 1991, NIH Publ. No. 91-3242, Vol. I, pages 647-669), although not all CDR residues are necessarily directly involved in antigen binding.

FR residues and Ig constant domains typically are not directly involved in antigen binding, but can contribute to antigen binding or mediate antibody effector function. Some FR residues can have a significant effect on antigen binding in at least three ways: by noncovalently binding directly to an epitope, by interacting with one or more CDR residues, and by affecting the interface between the heavy and light chains. The constant domains mediate various Ig effector functions, such as participation of the antibody in antibody dependent cellular cytotoxicity (ADCC), complement dependent cytotoxicity (CDC) and/or antibody dependent cellular phagocytosis (ADCP).

The light chains of vertebrate immunoglobulins are assigned to one of two clearly distinct classes, kappa (k) and lambda (λ), based on the amino acid sequence of the constant domain. By comparison, the heavy chains of mammalian immunoglobulins are assigned to one of five major classes, according to the sequence of the constant domains: IgA, IgD, IgE, IgG, and IgM. IgG and IgA are further divided into subclasses (isotypes), e.g., IgG1, IgG2, IgG3, IgG4, IgA, and IgA2. The heavy chain constant domains that correspond to the different classes of immunoglobulins are called α, δ, ε, γ, and µ, respectively. The subunit structures and three-dimensional configurations of the classes of native immunoglobulins are well known.

The terms "antibody", "anti-CD70 antibody", "humanized anti-CD70 antibody", and "variant humanized anti-CD70 antibody" are used herein in the broadest sense and specifically encompass full-length and native antibodies, monoclonal antibodies (including full-length monoclonal antibodies), polyclonal antibodies, multispecific antibodies (e.g., bispecific antibodies), and antibody or antigen-binding fragments thereof, such as variable domains and other portions of antibodies that exhibit a desired biological activity, e.g., CD70 binding.

The term "monoclonal antibody" (mAb) refers to an antibody obtained from a population of substantially homogeneous antibodies; that is, the individual antibodies comprising the population are identical except for naturally occurring mutations that may be present in minor amounts. Monoclonal antibodies are highly specific, being directed against a single antigenic determinant, also referred to as an epitope. The modifier "monoclonal" is indicative of a substantially homogeneous population of antibodies directed to the identical epitope and is not to be construed as requiring production of the antibody by any particular method. Monoclonal antibodies can be made by any technique or methodology known in the art; for example, the hybridoma method first described by Köhler et al., 1975, *Nature* 256: 495, or recombinant DNA methods known in the art (see, e.g., U.S. Pat. No. 4,816,567). In another example, monoclonal antibodies can also be isolated from phage antibody libraries, using techniques described in Clackson et al., 1991, *Nature* 352: 624-628, and Marks et al., 1991, *J. Mol. Biol.* 222:581-597.

In contrast, the antibodies in a preparation of polyclonal antibodies are typically a heterogeneous population of immunoglobulin isotypes and/or classes and also exhibit a variety of epitope specificity.

The term "chimeric" antibody, as used herein, is a type of monoclonal antibody in which a portion of or the complete amino acid sequence in one or more regions or domains of the heavy and/or light chain is identical with, homologous to, or a variant of the corresponding sequence in a monoclonal antibody from another species or belonging to another immunoglobulin class or isotype, or from a consensus sequence. Chimeric antibodies include fragments of such antibodies, provided that the antibody fragment exhibits the desired biological activity of its parent antibody, for example binding to the same epitope (see, e.g., U.S. Pat. No. 4,816, 567; and Morrison et al., 1984, *Proc. Natl. Acad. Sci. USA* 81:6851-6855). Methods for producing chimeric antibodies are known in the art. (See, e.g., Morrison, 1985. *Science* 229:1202; Oi et al., 1986, *BioTechniques* 4:214; Gillies et al., 1989, *J. Immunol. Methods* 125:191-202; U.S. Pat. Nos. 5,807,715; 4,816,567; and 4,816,397.)

The terms "antibody fragment", "anti-CD70 antibody fragment", "humanized anti-CD70 antibody fragment", and "variant humanized anti-CD70 antibody fragment" refer to a portion of a full-length anti-CD70 antibody in which a variable region or a functional capability is retained, for example, specific CD70 epitope binding. Examples of antibody fragments include, but are not limited to, a Fab, Fab', F(ab')$_2$, Fd, Fv, scFv and scFv-Fc fragment, diabody, triabody, tetrabody, linear antibody, single-chain antibody, and other multispecific antibodies formed from antibody fragments. (See Holliger and Hudson, 2005, *Nat. Biotechnol.* 23:1126-1136.)

A "single-chain Fv" or "scFv" antibody fragment is a single chain Fv variant comprising the $V_H$ and $V_L$ domains of an antibody, in which the domains are present in a single polypeptide chain and which is capable of recognizing and binding antigen. The scFv polypeptide optionally contains a polypeptide linker positioned between the $V_H$ and $V_L$ domains that enables the scFv to form a desired three-dimensional structure for antigen binding (see, e.g., Pluckthun, 1994, In *The Pharmacology of Monoclonal Antibodies*, Vol. 113, Rosenburg and Moore eds., Springer-Verlag, New York, pp. 269-315).

The term "diabody" refers to small antibody fragment having two antigen-binding sites. Each fragment contains a heavy chain variable domain ($V_H$) concatenated to a light chain variable domain ($V_L$) to form a $V_H$-$V_L$ or $V_L$-$V_H$ polypeptide. By using a linker that is too short to allow pairing between the two domains on the same chain, the linked $V_H$-$V_L$ domains are forced to pair with complementary domains of another chain, creating two antigen-binding sites. Diabodies are described more fully, for example, in EP 404 097; WO 93/11161; and Hollinger et al., 1993, *Proc. Natl. Acad. Sci. USA* 90:6444-6448.

The term "linear antibody" refers to antibodies that comprises a pair of tandem Fd segments ($V_H$-$C_H$1-$V_H$-$C_H$1) that form a pair of antigen binding regions. Linear antibodies can be bispecific or monospecific, as described in Zapata et al., 1995, *Protein Eng.* 8(10):1057-1062.

A "humanized antibody" refers to an immunoglobulin amino acid sequence variant or fragment thereof which is capable of binding to a predetermined antigen and which comprises a variable region polypeptide chain having framework regions having substantially the amino acid sequence of a human immunoglobulin and a CDR(s) having substantially the amino acid sequence of a non-human immunoglobulin.

Generally, a humanized antibody has one or more amino acid residues introduced into it from a source which is non-human. These non-human amino acid residues are referred to herein as "import" residues, which are typically taken from an "import" antibody domain, particularly a variable domain. An import residue, sequence, or antibody has a desired affinity and/or specificity, or other desirable antibody biological activity as discussed herein.

In general, the humanized antibody will comprise substantially all of at least one, and typically two, variable domains in which all or substantially all of the CDR regions correspond to those of a non-human immunoglobulin and all or substantially all of the framework regions are those of a human immunoglobulin sequence, such as from, for example, a consensus or germline sequence. The humanized antibody optionally also will comprise at least a portion of an immunoglobulin Fc domain, typically that of a human immunoglobulin. For example, the antibody may contain both the light chain as well as at least the variable domain of a heavy chain. The antibody also may include the $C_H$1, hinge (J), $C_H$2, $C_H$3, and/or $C_H$4 regions of the heavy chain, as appropriate.

The humanized antibody can be selected from any class of immunoglobulins, including IgM, IgG, IgD, IgA and IgE, and any isotype, including IgG$_1$, IgG$_2$, IgG$_3$ and IgG$_4$. The constant region or domain can include, for example, a complement fixing constant domain where it is desired that the humanized antibody exhibit cytotoxic activity (e.g., IgG$_1$). Where such cytotoxic activity is not desirable, the constant domain may be of another class (e.g., IgG$_2$). The humanized antibody may comprise sequences from more than one class or isotype, and selecting particular constant domains to optimize desired effector functions is within the ordinary skill in the art.

The FR and CDR regions of the humanized antibody need not correspond precisely to the parental sequences, e.g., the import CDR or the consensus FR may be altered by substitution, insertion or deletion of at least one residue so that the CDR or FR residue at that site does not correspond to either the consensus or the import antibody. Such mutations typically will not be extensive. Usually, at least 75% of the humanized antibody residues will correspond to those of the parental FR and CDR sequences, more often at least 90%, and most often greater than 95%.

The term "antibody effector function(s)" as used herein refers to a function contributed by an Fc domain(s) of an Ig. Such functions can be, for example, antibody-dependent cellular cytotoxicity, antibody-dependent cellular phagocytosis or complement-dependent cytotoxicity. Such function can be effected by, for example, binding of an Fc effector domain(s) to an Fc receptor on an immune cell with phagocytic or lytic activity or by binding of an Fc effector domain(s) to components of the complement system. Typically, the effect(s) mediated by the Fc-binding cells or complement components result in inhibition and/or depletion of the CD70 targeted cell. Without intending to be bound by any particular theory, Fc regions of antibodies can recruit Fc receptor (FcR)-expressing cells and juxtapose them with antibody-coated target cells. Cells expressing surface FcR for IgGs including FcγRIII (CD16), FcγRII (CD32) and FcγRIII (CD64) can act as effector cells for the destruction of IgG-coated cells. Such effector cells include monocytes, macrophages, natural killer (NK) cells, neutrophils and eosinophils. Engagement of FcγR by IgG activates antibody-dependent cellular cytotoxicity (ADCC) or antibody-dependent cellular phagocytosis (ADCP). ADCC is mediated by CD16$^+$ effector cells through the secretion of membrane pore-forming proteins and proteases, while phagocytosis is mediated by CD32$^+$ and CD64$^+$ effector cells (see *Fundamental Immunology*, 4$^{th}$ ed., Paul ed., Lippincott-Raven, N.Y., 1997, Chapters 3, 17 and 30; Uchida et al., 2004, *J. Exp. Med.* 199:1659-69; Akewanlop et al., 2001, *Cancer Res.* 61:4061-65; Watanabe et al., 1999, *Breast Cancer Res. Treat.* 53:199-207). In addition to ADCC and ADCP, Fc regions of cell-bound antibodies can also activate the complement classical pathway to elicit complement-dependent cytotoxicity (CDC). C1q of the complement system binds to the Fc regions of antibodies when they are complexed with antigens. Binding of C1q to cell-bound antibodies can initiate a cascade of events involving the proteolytic activation of C4 and C2 to generate the C3 convertase. Cleavage of C3 to C3b by C3 convertase enables the activation of terminal complement components including C5b, C6, C7, C8 and C9. Collectively, these proteins form membrane-attack complex pores on the antibody-coated cells. These pores disrupt the cell membrane integrity, killing the target cell (see *Immunobiology*, 6$^{th}$ ed., Janeway et al., Garland Science, N.Y., 2005, Chapter 2).

The term "antibody-dependent cellular cytotoxicity", or ADCC, is a mechanism for inducing cell death that depends upon the interaction of antibody-coated target cells with immune cells possessing lytic activity (also referred to as effector cells). Such effector cells include natural killer cells, monocytes/macrophages and neutrophils. The effector cells attach to an Fc effector domain(s) of Ig bound to target cells via their antigen-combining sites. Death of the antibody-coated target cell occurs as a result of effector cell activity.

The term "antibody-dependent cellular phagocytosis", or ADCP, refers to the process by which antibody-coated cells are internalized, either in whole or in part, by phagocytic immune cells (e.g., macrophages, neutrophils and dendritic cells) that bind to an Fc effector domain(s) of Ig.

The term "complement-dependent cytotoxicity", or CDC, refers to a mechanism for inducing cell death in which an Fc effector domain(s) of a target-bound antibody activates a series of enzymatic reactions culminating in the formation of holes in the target cell membrane. Typically, antigen-antibody complexes such as those on antibody-coated target cells bind and activate complement component C1q which in turn activates the complement cascade leading to target cell death. Activation of complement may also result in deposition of complement components on the target cell surface that facilitate ADCC by binding complement receptors (e.g., CR3) on leukocytes.

"Immune cell" as used herein refers to a cell of hematopoietic lineage involved in regulating an immune response. In typical embodiments, an immune cell is a T lymphocyte, a B lymphocyte, an NK cell, a monocyte/macrophage, or a dendritic cell.

"Effector cell" as used herein refers to a cell that expresses a surface receptor for the Fc domain of an immunoglobulin (FcR). For example, cells that express surface FcR for IgGs including FcγRIII (CD16), FcγRII (CD32) and FcγRIII (CD64) can act as effector cells. Such effector cells include monocytes, macrophages, natural killer (NK) cells, neutrophils and eosinophils.

A "therapeutic agent" is an agent that exerts a cytotoxic, cytostatic, and/or immunomodulatory effect on cancer cells, activated immune cells or other target cell population. Examples of therapeutic agents include cytotoxic agents, chemotherapeutic agents, cytostatic agents, and immunomodulatory agents.

A "cytotoxic effect" refers to the depletion, elimination and/or the killing of a target cell. A "cytotoxic agent" refers to an agent that has a cytotoxic effect on a cell. The term is intended to include radioactive isotopes (such as $I^{131}$, $I^{125}$, $Y^{90}$, and $Re^{186}$), chemotherapeutic agents, and toxins such as enzymatically active toxins of bacterial, fungal, plant, or animal origin, and fragments thereof. Such cytotoxic agents can be coupled to an antibody, e.g., a humanized anti-CD70 antibody, and used, for example, to treat a patient indicated for therapy with the antibody. In one embodiment, "cytotoxic agent" includes monoclonal antibodies, e.g., antibodies used in combination with the humanized antibodies described herein.

A "chemotherapeutic agent" is a chemical compound useful in the treatment of cancer. Examples of chemotherapeutic agents include alkylating agents such a thiotepa and cyclophosphamide (CYTOXAN™); alkyl sulfonates such as busulfan, improsulfan, and piposulfan; aziridines such as benzodopa, carboquone, meturedopa, and uredopa; ethylenimines and methylamelamines including altretamine, triethylenemelamine, triethylenephosphoramide, triethylenethiophosphoramide, and trimethylolomelamine; acetogenins (especially bullatacin and bullatacinone); camptothecin (including the synthetic analogue topotecan); bryostatin; callystatin; CC-1065 (including its adozelesin, carzelesin, and bizelesin synthetic analogues) and derivatives thereof; cryptophycines (particularly cryptophycin 1 and cryptophycin 8); dolastatin, auristatins (including analogues monomethyl-auristatin E and monomethyl-auristatin F (see, e.g., U.S. Published Application No. 2005-0238649, published Oct. 27, 2005, incorporated herein in its entirety); duocarmycin (including the synthetic analogues, KW-2189 and CBI-TMI); eleutherobin; pancratistatin; sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine; trofosfamide, uracil mustard; nitrosureas such as carmustine, chlorozotocin, fotemustine, lomustine, nimustine, ranimustine; antibiotics such as the enediyne antibiotics (e.g., calicheamicin, especially calichemicin gamma1I and calicheamicin phi1I, see for example, *Agnew, Chem. Intl. Ed. Engl.*, 33:183-186; dynemicin, including dynemicin A; bisphosphonates, such as clodronate; esperamicin; as well as neocarzinostatin chromophore and related chromoprotein enediyne antibiotic chromomophores), aclacinomysins, actinomycin, authramycin, azaserine, bleomycins, cactinomycin, carabicin, caminomycin, carzinophilin, chromomycins, dactinomycin, daunorubicin, detorubicin, 6-diazo-5- oxo-L-norleucine, doxorubicin (Adriamycin™) (including morpholino-doxorubicin, cyanomorpholino-doxorubicin, 2-pyrrolino-doxorubicin, and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such a methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adranals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; democolcine; diaziquone; elformithine; elliptinium acetate; an epothilone; etoglucid; gallium nitrate; hydroxyurea; lentinan; lonidamine; maytansinoids such as maytansine and ansamitocins; mitoguazone, mitoxantrone; mopidamol; nitracrine; pentostatin; phenamet; pirarubicin; losoxantrone; podophyllinic acid; 2-ethylhydrazide; procarbazine; PSK®; razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitabronitol; mitolactol; pipobroman; gacytosine; arabinoside ("Ara-C"); cyclophosphamide; thiotepa; taxoids, e.g., paclitaxel (TAXOL®, Bristol-Myers Squibb Oncology, Princeton, N.J.) and doxetaxel (TAXOTERE®, Rhône-Poulenc Rorer, Antony, France); chlorambucil; gemcitabine (Gemzar™); 6-thioguanine; mercaptopurine; methotrexate; platinum analogs such as cisplatin and carboplatin; vinblastine; platinum; etoposide (VP-16); ifosfamide; mitoxantrone; vincristine; vinorelbine (Navelbine™); novantrone; teniposide; edatrexate; daunomycin; aminopterin; xeloda; ibandronate; CPT-11; topoisomerase inhibitor RFS 2000; difluoromethylornithine (DMFO); retinoids such as retinoic acid; capecitabine; and pharmaceutically acceptable salts, acids, or derivatives of any of the above. Also included in this definition are anti-hormonal agents that act to regulate or inhibit hormone action on tumors such as anti-estrogens and selective estrogen receptor modulators (SERMs), including, for example, tamoxifen (including Nolvadex™), raloxifene, droloxifene, 4-hydroxytamoxifen, trioxifene, keoxifene, LY117018, onapristone, and toremifene (Fareston™); aromatase inhibitors that inhibit the enzyme aromatase, which regulates estrogen production in the adrenal glands, such as, for example, 4(5)-imidazoles, aminoglutethimide, megestrol acetate (Megace™), exemestane, formestane, fadrozole, vorozole (Rivisor™), letrozole (Femara™), and anastrozole (Arimidex™); and anti-androgens such as flutamide, nilutamide, bicalutamide, leuprolide, and goserelin; and pharmaceutically acceptable salts, acids, or derivatives of any of the above.

The term "prodrug" as used herein refers to a precursor or derivative form of a pharmaceutically active substance that is less cytotoxic to tumor cells compared to the parent drug and is capable of being enzymatically activated or converted into the more active parent form. See, for example, Wilman, 1986, "Prodrugs in Cancer Chemotherapy", In *Biochemical Society Transactions*, 14, pp. 375-382, 615th Meeting Belfast; and Stella et al., 1985, "Prodrugs: A Chemical Approach to Targeted Drug Delivery, In: "*Directed Drug Delivery*, Borchardt et al., (ed.), pp. 247-267, Humana Press. Useful prodrugs include, but are not limited to, phosphate-containing prodrugs, thiophosphate-containing prodrugs, sulfate-containing prodrugs, peptide-containing prodrugs, D-amino acid-modified prodrugs, glycosylated prodrugs, β-lactam-containing prodrugs, optionally substituted phenoxyacetamide-containing prodrugs, and optionally substituted phenylacetamide-containing prodrugs, 5-fluorocytosine and other 5-fluorouridine prodrugs that can be converted into the more active cytotoxic free drug. Examples of cytotoxic drugs that can be derivatized into a prodrug form include, but are not limited to, those chemotherapeutic agents described above.

A "cytostatic effect" refers to the inhibition of cell proliferation. A "cytostatic agent" refers to an agent that has a cytostatic effect on a cell, thereby inhibiting the growth and/or expansion of a specific subset of cells.

The term "immunomodulatory effect" as used herein refers to a stimulation (immunostimulatory) or inhibition (immunosuppressive) of the development or maintenance of an immunologic response Inhibition can be effected by, for example, by elimination of immune cells (e.g., T or B lymphocytes); induction or generation of immune cells that can modulate (e.g., down-regulate) the functional capacity of other cells; induction of an unresponsive state in immune cells (e.g., anergy); or increasing, decreasing or changing the activity or function of immune cells, including, for example, altering the pattern of proteins expressed by these cells (e.g., altered production and/or secretion of certain classes of molecules such as cytokines, chemokines, growth factors, transcription factors, kinases, costimulatory molecules or other cell surface receptors, and the like). An "immunomodulatory agent" refers to an agent that has an immunomodulatory effect on a cell. In some embodiments, an immunomodulatory agent has a cytotoxic or cytostatic effect on an immune cell that promotes an immune response.

The term "label" refers to a detectable compound or composition that is conjugated directly or indirectly to the antibody. The label may itself be detectable (e.g., radioisotope labels or fluorescent labels) or, in the case of an enzymatic label, may catalyze chemical alteration of a substrate compound or composition that is detectable. Labeled anti-CD70 antibody can be prepared and used in various applications including in vitro and in vivo diagnostics.

An "isolated" nucleic acid molecule is a nucleic acid molecule that is identified and separated from at least one contaminant nucleic acid molecule with which it is ordinarily associated in the natural source of the nucleic acid. An isolated nucleic acid molecule is other than in the form or setting in which it is found in nature. Isolated nucleic acid molecules therefore are distinguished from the nucleic acid molecule as it exists in natural cells. However, an isolated nucleic acid molecule includes a nucleic acid molecule contained in cells that ordinarily express the antibody where, for example, the nucleic acid molecule is in a chromosomal location different from that of natural cells.

The term "control sequences" refers to polynucleotide sequences necessary for expression of an operably linked coding sequence in a particular host organism. The control sequences suitable for use in prokaryotic cells include, for example, promoter, operator, and ribosome binding site sequences. Eukaryotic control sequences include, but are not limited to, promoters, polyadenylation signals, and enhancers. These control sequences can be utilized for expression and production of anti-CD70 binding agent in prokaryotic and eukaryotic host cells.

A nucleic acid sequence is "operably linked" when it is placed into a functional relationship with another nucleic acid sequence. For example, a nucleic acid presequence or secretory leader is operably linked to a nucleic acid encoding a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading frame. However, enhancers are optionally contiguous. Linking can be accomplished by ligation at convenient restriction sites. If such sites do not exist, synthetic oligonucleotide adaptors or linkers can be used to link the DNA sequences.

The term "polypeptide" refers to a polymer of amino acids and its equivalent and does not refer to a specific length of a product; thus, "peptides" and "proteins" are included within the definition of a polypeptide. Also included within the definition of polypeptides are "antibodies" as defined herein. A "polypeptide region" refers to a segment of a polypeptide, which segment may contain, for example, one or more domains or motifs (e.g., a polypeptide region of an antibody can contain, for example, one or more complementarity determining regions (CDRs)). The term "fragment" refers to a portion of a polypeptide typically having at least 20 contiguous or at least 50 contiguous amino acids of the polypeptide. A "derivative" is a polypeptide or fragment thereof having one or more non-conservative or conservative amino acid substitutions relative to a second polypeptide; or a polypeptide or fragment thereof that is modified by covalent attachment of a second molecule such as, e.g., by attachment of a heterologous polypeptide, or by glycosylation, acetylation, phosphorylation, and the like. Further included within the definition of "derivative" are, for example, polypeptides containing one or more analogs of an amino acid (e.g., unnatural amino acids and the like), polypeptides with unsubstituted linkages, as well as other modifications known in the art, both naturally and non-naturally occurring.

An "isolated" polypeptide is one which has been identified and separated and/or recovered from a component of its natural environment. Contaminant components of its natural environment are materials which would interfere with diagnostic or therapeutic uses for the polypeptide, and may include enzymes, hormones, and other proteinaceous or nonproteinaceous solutes. An isolated polypeptide includes an isolated antibody, or a fragment or derivative thereof. "Antibody" includes the antibody in situ within recombinant cells since at least one component of the antibody's natural environment will not be present.

In certain embodiments, the antibody will be purified (1) to greater than 95% by weight of antibody as determined by the Lowry method, and in other aspects to more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain.

The term "heterologous," in the context of a polypeptide, means from a different source (e.g., a cell, tissue, organism, or species) as compared with another polypeptide, so that the two polypeptides are different. Typically, a heterologous polypeptide is from a different species.

In the context of immunoglobulin polypeptides or fragments thereof, "conservative substitution" means one or more amino acid substitutions that do not substantially reduce specific binding (e.g., as measured by the $K_D$) of the immunoglobulin polypeptide or fragment thereof to an antigen (i.e., substitutions that increase binding affinity, that do not significantly alter binding affinity, or that reduce binding affinity by no more than about 40%, typically no more than about 30%, more typically no more than about 20%, even more typically no more than about 10%, or most typically no more than about 5%, as determined by standard binding assays such as, e.g., ELISA).

The terms "identical" or "percent identity," in the context of two or more nucleic acids or polypeptide sequences, refer to two or more sequences or subsequences that are the same or have a specified percentage of nucleotides or amino acid residues that are the same, when compared and aligned for maximum correspondence. To determine the percent identity, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of positions (e.g., overlapping positions)×100). In some embodiments, the two sequences are the same length.

The term "substantially identical," in the context of two nucleic acids or polypeptides, refers to two or more sequences or subsequences that have at least 50%, at least 55%, at least 60%, or at least 65% identity; typically at least 70% or at least 75% identity; more typically at least 80% or at least 85% identity; and even more typically at least 90%, at least 95%, or at least 98% identity (e.g., as determined using one of the methods set forth infra).

The terms "similarity" or "percent similarity" in the context of two or more polypeptide sequences refer to two or more sequences or subsequences that have a specified percentage of amino acid residues that are the same or conservatively substituted when compared and aligned for maximum correspondence, as measured using one of the methods set forth infra. By way of example, a first amino acid sequence can be considered similar to a second amino acid sequence when the first amino acid sequence is at least 50%, 60%, 70%, 75%, 80%, 90%, or 95% identical, or conservatively substituted, to the second amino acid sequence when compared to an equal number of amino acids as the number contained in the first sequence, or when compared to an alignment of polypeptides that has been aligned by, e.g., one of the methods set forth infra.

The terms "substantial similarity" or "substantially similar," in the context of polypeptide sequences, indicate that a polypeptide region has a sequence with at least 70%, typically at least 80%, more typically at least 85%, or at least 90% or at least 95% sequence similarity to a reference sequence. For example, a polypeptide is substantially similar to a second polypeptide, for example, where the two peptides differ by one or more conservative substitution(s).

In the context of anti-CD70 antibodies, or derivatives thereof, a protein that has one or more polypeptide regions substantially identical or substantially similar to one or more antigen-binding regions (e.g., a heavy or light chain variable region, or a heavy or light chain CDR) of an anti-CD70 antibody retains specific binding to an epitope of CD70 recognized by the anti-CD70 antibody, as determined using any of various standard immunoassays known in the art or as referred to herein.

The determination of percent identity or percent similarity between two sequences can be accomplished using a mathematical algorithm. A preferred, non-limiting example of a mathematical algorithm utilized for the comparison of two sequences is the algorithm of Karlin and Altschul, 1990, *Proc. Natl. Acad. Sci. USA* 87:2264-2268, modified as in Karlin and Altschul, 1993, *Proc. Natl. Acad. Sci. USA* 90:5873-5877. Such an algorithm is incorporated into the NBLAST and XBLAST programs of Altschul et al., 1990, *J. Mol. Biol.* 215:403-410. BLAST nucleotide searches can be performed with the NBLAST program, score=100, wordlength=12, to obtain nucleotide sequences homologous to a nucleic acid encoding a protein of interest. BLAST protein searches can be performed with the XBLAST program, score=50, wordlength=3, to obtain amino acid sequences homologous to protein of interest. To obtain gapped alignments for comparison purposes, Gapped BLAST can be utilized as described in Altschul et al., 1997, *Nucleic Acids Res.* 25:3389-3402. Alternatively, PSI-Blast can be used to perform an iterated search which detects distant relationships between molecules (Id.). When utilizing BLAST, Gapped BLAST, and PSI-Blast programs, the default parameters of the respective programs (e.g., XBLAST and NBLAST) can be used. Another non-limiting example of a mathematical algorithm utilized for the comparison of sequences is the algorithm of Myers and Miller, CABIOS (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Additional algorithms for sequence analysis are known in the art and include ADVANCE and ADAM as described in Torellis and Robotti, 1994, *Comput. Appl. Biosci.* 10:3-5; and FASTA described in Pearson and Lipman, 1988, *Proc. Natl. Acad. Sci. USA* 85:2444-8. Within FASTA, ktup is a control option that sets the sensitivity and speed of the search. If ktup=2, similar regions in the two sequences being compared are found by looking at pairs of aligned residues; if ktup=1, single aligned amino acids are examined. ktup can be set to 2 or 1 for protein sequences, or from 1 to 6 for DNA sequences. The default if ktup is not specified is 2 for proteins and 6 for DNA. Alternatively, protein sequence alignment may be carried out using the CLUSTAL W algorithm, as described by Higgins et al., 1996, *Methods Enzymol.* 266:383-402.

As used herein, the expressions "cell", "cell line", and "cell culture" are used interchangeably and all such designations include the progeny thereof. Thus, "transformants" and "transformed cells" include the primary subject cell and cultures derived therefrom without regard for the number of transfers. It is also understood that all progeny may not be precisely identical in DNA content, due to deliberate or naturally occurring mutations. Mutant progeny that have the same function or biological activity as screened for in the originally transformed cell are included. Where distinct designations are intended, it will be clear from the context.

The term "subject" for purposes of treatment refers to any animal, particularly an animal classified as a mammal, including humans, domesticated and farm animals, and zoo, sports, or pet animals, such as dogs, horses, cats, cows, and the like. Preferably, the subject is human.

A "disorder", as used herein, and the terms "CD70-associated disorder" and "CD70-associated disease" refer to any condition that would benefit from treatment with an anti-CD70 binding agent, as described herein. A "CD70-associated disorder" and "CD70-associated disease" typically express CD70, or a fragment thereof, on the cell surface. This includes chronic and acute disorders or diseases including those pathological conditions that predispose the mammal to the disorder in question. Non-limiting examples or disorders to be treated herein include cancer, hematological malignancies, benign and malignant tumors, leukemias and lymphoid malignancies, carcinomas, and inflammatory, angiogenic and immunologic disorders. Specific examples of disorders are disclosed infra.

The terms "treatment" and "therapy", and the like, as used herein, are meant to include therapeutic as well as prophylactic, or suppressive measures for a disease or disorder leading to any clinically desirable or beneficial effect, including but not limited to alleviation or relief of one or more symptoms, regression, slowing or cessation of progression of the disease or disorder. Thus, for example, the term treatment includes the administration of an agent prior to or following the onset of a symptom of a disease or disorder, thereby preventing or removing all signs of the disease or disorder. As another example, the term includes the administration of an agent after clinical manifestation of the disease to combat the symptoms of the disease. Further, administration of an agent after onset and after clinical symptoms have developed where administration affects clinical parameters of the disease or disorder, such as the degree of tissue injury or the amount or extent of metastasis, whether or not the treatment leads to amelioration of the disease, comprises "treatment" or "therapy" as used herein.

As used herein, the terms "prevention" or "prevent" refer to administration of an anti-CD70 binding agent to a subject before the onset of a clinical or diagnostic symptom of a CD70-expressing cancer or immunological disorder (e.g., administration to an individual with a predisposition or at a high risk of acquiring the CD70-expressing cancer or immunological disorder) to (a) block the occurrence or onset of the CD70-expressing cancer or immunological disorder, or one or more of clinical or diagnostic symptoms thereof, (b) inhibit the severity of onset of the CD70-expressing cancer or immunological disorder, or (c) to lessen the likelihood of the onset of the CD70-expressing cancer or immunological disorder.

The term "intravenous infusion" refers to introduction of an agent, e.g., a therapeutic agent, into the vein of an animal or human patient over a period of time greater than approximately 15 minutes, generally between approximately 30 to 90 minutes.

The term "intravenous bolus" or "intravenous push" refers to drug administration into a vein of an animal or human such that the body receives the drug in approximately 15 minutes or less, generally 5 minutes or less.

The term "subcutaneous administration" refers to introduction of an agent, e.g., a therapeutic agent, under the skin of an animal or human patient, typically within a pocket between the skin and underlying tissue, by relatively slow, sustained delivery from a drug receptacle. Pinching or drawing the skin up and away from underlying tissue may create the pocket.

The term "package insert" is used to refer to instructions customarily included in commercial packages of therapeutic products, that contain information about the indications, usage, administration, contraindications and/or warnings concerning the use of such therapeutic products.

A "liposome" is a small vesicle composed of various types of lipids, phospholipids and/or surfactant which is useful for delivery of a drug (such as an antibody) to a mammal. The components of the liposome are commonly arranged in a bilayer formation, similar to the lipid arrangement of biological membranes.

The term "subcutaneous infusion" refers to introduction of a drug under the skin of an animal or human patient, preferably within a pocket between the skin and underlying tissue, by relatively slow, sustained delivery from a drug receptacle for a period of time including, but not limited to, 30 minutes or less, or 90 minutes or less. Optionally, the infusion may be made by subcutaneous implantation of a drug delivery pump implanted under the skin of the animal or human patient, wherein the pump delivers a predetermined amount of drug for a predetermined period of time, such as 30 minutes, 90 minutes, or a time period spanning the length of the treatment regimen.

The term "subcutaneous bolus" refers to drug administration beneath the skin of an animal or human patient, where bolus drug delivery is less than approximately 15 minutes; in another aspect, less than 5 minutes, and in still another aspect, less than 60 seconds. In yet even another aspect, administration is within a pocket between the skin and underlying tissue, where the pocket may be created by pinching or drawing the skin up and away from underlying tissue.

The term "effective amount" refers to the amount of an anti-CD70 binding agent (e.g., an antibody or derivative or other binding agent) that is sufficient to inhibit the occurrence or ameliorate one or more clinical or diagnostic symptoms of a CD70-expressing cancer or immunological disorder in a subject. An effective amount of an agent is administered according to the methods described herein in an "effective regimen." The term "effective regimen" refers to a combination of amount of the agent and dosage frequency adequate to accomplish treatment or prevention of a CD70-expressing cancer or immunological disorder.

The term "therapeutically effective amount" is used to refer to an amount of a therapeutic agent having beneficial patient outcome, for example, a growth arrest effect or deletion of the cell. In one aspect, the therapeutically effective amount has apoptotic activity, or is capable of inducing cell death. In another aspect, the therapeutically effective amount refers to a target serum concentration that has been shown to be effective in, for example, slowing disease progression. Efficacy can be measured in conventional ways, depending on the condition to be treated. For example, in neoplastic diseases or disorders characterized by cells expressing CD70, efficacy can be measured by assessing the time to disease progression (TTP), or determining the response rates (RR).

The term "pharmaceutically acceptable" as used herein means approved by a regulatory agency of the Federal or a state government or listed in the U.S. Pharmacopeia or other generally recognized pharmacopeia for use in animals, and more particularly in humans. The term "pharmaceutically compatible ingredient" refers to a pharmaceutically acceptable diluent, adjuvant, excipient, or vehicle with which an anti-CD70-binding agent is administered.

The phrase "pharmaceutically acceptable salt," as used herein, refers to pharmaceutically acceptable organic or inorganic salts of an anti-CD70 binding agent or therapeutic agent. The anti-CD70 binding agent or therapeutic agent contains at least one amino group, and accordingly acid addition salts can be formed with this amino group or other suitable groups. Exemplary salts include, but are not limited to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p toluenesulfonate, and pamoate (i.e., 1,1' methylene bis-(2 hydroxy 3 naphthoate)) salts. A pharmaceutically acceptable salt may involve the inclusion of another molecule such as an acetate ion, a succinate ion or other counterion. The counterion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counterion.

"Pharmaceutically acceptable solvate" or "solvate" refer to an association of one or more solvent molecules and an anti-CD70 binding agent and/or therapeutic agent. Examples of solvents that form pharmaceutically acceptable solvates include, but are not limited to, water, isopropanol, ethanol, methanol, DMSO, ethyl acetate, acetic acid, and ethanolamine.

The abbreviation "AFP" refers to dimethylvaline-valine-dolaisoleuine-dolaproine-phenylalanine-p-phenylenediamine.

The abbreviation "MMAE" refers to monomethyl auristatin E.

The abbreviation "AEB" refers to an ester produced by reacting auristatin E with paraacetyl benzoic acid.

The abbreviation "AEVB" refers to an ester produced by reacting auristatin E with benzoylvaleric acid.

The abbreviation "MMAF" refers to dovaline-valine-dolaisoleunine-dolaproine-phenylalanine.

The abbreviations "fk" and "phe-lys" refer to the linker phenylalanine-lysine.

II. ANTI-CD70 ANTIBODIES AND DERIVATIVES THEREOF

The compositions and methods described herein encompass the use of a CD70 binding agent that specifically binds to CD70. The CD70 binding agent may exert a cytotoxic, cytostatic or immunomodulatory effect on CD70-expressing cancer cells, activated immune cells or other target cells. The CD70 binding agent can be, for example, an anti-CD70 antibody, an antigen-binding fragment of an anti-CD70 antibody, a derivative thereof, or other CD70-binding agent comprising at least one complementarity determining region (CDR) of a CD70-binding antibody.

In one aspect, the CD70 binding agent comprises one or more complementarity determining regions (CDRs) identical, substantially identical or substantially similar to one or more CDR(s) of monoclonal antibody 1F6. (The nucleic acid and amino acid sequences of the heavy and light chain variable regions of 1F6 are set forth in SEQ ID NO:1 and SEQ ID NO:2, and SEQ ID NO: 21 and SEQ ID NO: 22, respectively, and are disclosed in International Patent Publication No. WO 04/073656; the disclosure of which is incorporated by reference herein.) For example, the binding agent can include a heavy chain CDR and/or a light chain CDR that is identical or substantially identical or substantially similar to a corresponding heavy chain CDR (H1, H2, or H3 regions) or corresponding light chain CDR (L1, L2, or L3 regions) of mAb 1F6. In typical embodiments, the anti-CD70 binding agent has two or three heavy chain CDRs and/or two or three light chain CDRs that are identical, substantially identical or substantially similar to corresponding heavy and/or light chain CDRs of mAb 1F6.

For example, in some embodiments, where the anti-CD70 binding agent has at least one heavy chain CDR substantially identical or substantially similar to a heavy chain CDR of mAb 1F6, the binding agent can further include at least one light chain CDR that is substantially identical or substantially similar to a light chain CDR of mAb 1F6.

In some embodiments, the anti-CD70 binding agent includes a heavy or light chain variable domain, the variable domain having (a) a set of three CDRs identical, substantially identical or substantially similar to corresponding CDRs of mAb 1F6, and (b) a set of four variable region framework regions from a human immunoglobulin. For example, an anti-CD70 antibody can include a heavy and/or light chain variable domain(s), the variable domain(s) having (a) a set of three CDRs, in which the set of CDRs are from monoclonal antibody 1F6, and (b) a set of four framework regions derived from a human IgG. The antibody can optionally include a hinge region. In an exemplary embodiment, the anti-CD70 antibody is a fully humanized antibody.

In another aspect, the CD70 binding agent comprises one or more complementarity determining regions (CDRs) substantially identical or substantially similar to one or more CDR(s) of monoclonal antibody 2F2. (The nucleic acid and amino acid sequences of the heavy and light chain variable regions of 2F2 are set forth in SEQ ID NO:27 and SEQ ID NO:28, and SEQ ID NO: 29 and SEQ ID NO: 30, respectively, and are disclosed in International Patent Publication No. WO 04/073656; the disclosure of which is incorporated by reference herein.) For example, the binding agent can include a heavy chain CDR and/or a light chain CDR that is identical or substantially identical or substantially similar to a corresponding heavy chain CDR (H1, H2, or H3 regions) or corresponding light chain CDR (L1, L2, or L3 regions) of mAb 2F2. In typical embodiments, the anti-CD70 binding agent has two or three heavy chain CDRs and/or two or three light chain CDRs that are identical, substantially identical or substantially similar to corresponding heavy and/or light chain CDRs of mAb 2F2.

For example, in some embodiments, where an anti-CD70 antibody has at least one heavy chain CDR substantially identical or substantially similar to a heavy chain CDR of mAb 2F2, the antibody or derivative thereof can further include at least one light chain CDR that is substantially identical or substantially similar to a light chain CDR of mAb 2F2.

In some embodiments, the anti-CD70 binding agent includes a heavy or light chain variable domain, the variable domain having (a) a set of three CDRs identical, substantially identical or substantially similar to corresponding CDRs of mAb 2F2, and (b) a set of four variable region framework regions from a human immunoglobulin. For example, an anti-CD70 antibody can include a heavy and/or light chain variable domain(s), the variable domain(s) having (a) a set of three CDRs, in which the set of CDRs are from monoclonal antibody 2F2, and (b) a set of four framework regions derived from a human IgG. The antibody can optionally include a hinge region. In an exemplary embodiment, the anti-CD70 antibody is a fully humanized antibody.

In some embodiments, the framework regions are chosen from human germline exon $V_H$, $J_H$, Vκ and Jκ sequences. For example, acceptor sequences for humanization of FR of a c1F6 $V_H$ domain can be chosen from germline $V_H$ exons $V_H$1-18 (Matsuda et al., 1993, *Nature Genetics* 3:88-94) or $V_H$1-2 (Shin et al., 1991, *EMBO J.* 10:3641-3645) and for the hinge region ($J_H$), exon $J_H$-6 (Mattila et al., 1995, *Eur. J. Immunol.* 25:2578-2582). In other examples, germline Vκ exon B3 (Cox et al., 1994, *Eur. J. Immunol.* 24:827-836) and Jκ exon Jκ-1 (Hieter et al., 1982, *J. Biol. Chem.* 257:1516-1522) can be chosen as acceptor sequences for c1F6 $V_L$ domain humanization.

In some embodiments, the sequence of the framework region of the humanized anti-CD70 antibody includes a derivative of the acceptor human germline exon used, including derivatives in which mouse donor residues are reintroduced. These residues include reintroduction of the mouse donor residue at one or more of positions H46, H67, H68, H69, H70, H71, H80, H81, H82, H82A and H91 in the $V_H$ domain, according to the Kabat numbering convention.

The following table indicates the regions of humanized 1F6 to which each SEQ ID NO. corresponds.

TABLE 1

| MOLECULE | NUCLEOTIDE OR AMINO ACID | SEQ ID NO |
|---|---|---|
| c1F6 Heavy Chain Variable Region | Nucleotide | 1 |
| c1F6 Heavy Chain Variable Region | Amino Acid | 2 |
| h1F6 h$V_H$-D + hIgG$_1$ Constant Domain | Nucleotide | 3 |
| h1F6 h$V_H$-D + hIgG$_1$ Constant Domain | Amino Acid | 4 |
| h1F6 h$V_H$-E | Nucleotide | 5 |
| h1F6 h$V_H$-E | Amino Acid | 6 |
| h1F6 h$V_H$-E + hIgG$_1$ Constant Domain | Nucleotide | 7 |
| h1F6 h$V_H$-E + hIgG$_1$ Constant Domain | Amino Acid | 8 |
| h1F6 h$V_H$-H | Nucleotide | 9 |
| h1F6 h$V_H$-H | Amino Acid | 10 |
| h1F6 h$V_H$-H + hIgG$_1$ Constant Domain | Nucleotide | 11 |
| h1F6 h$V_H$-H + hIgG$_1$ Constant Domain | Amino Acid | 12 |
| h1F6 h$V_H$-J | Nucleotide | 13 |
| h1F6 h$V_H$-J | Amino Acid | 14 |
| h1F6 h$V_H$-J + hIgG$_1$ Constant Domain | Nucleotide | 15 |
| h1F6 h$V_H$-J + hIgG$_1$ Constant Domain | Amino Acid | 16 |
| h1F6 h$V_H$-M | Nucleotide | 17 |
| h1F6 h$V_H$-M | Amino Acid | 18 |
| h1F6 h$V_H$-M + hIgG$_1$ Constant Domain | Nucleotide | 19 |
| h1F6 h$V_H$-M + hIgG$_1$ Constant Domain | Amino Acid | 20 |
| c1F6 Light Chain Variable Region | Nucleotide | 21 |
| c1F6 Light Chain Variable Region | Amino Acid | 22 |
| h$V_L$A | Nucleotide | 23 |
| h$V_L$A | Amino Acid | 24 |
| h$V_L$A + human κ constant domain | Nucleotide | 25 |
| h$V_L$A + human κ constant domain | Amino Acid | 26 |
| c2F2 Heavy Chain Variable Region | Nucleotide | 27 |
| c2F2 Heavy Chain Variable Region | Amino Acid | 28 |
| c2F2 Light Chain Variable Region | Nucleotide | 29 |
| c2F2 Light Chain Variable Region | Amino Acid | 30 |

In some embodiments, the CD70 binding agent can be a humanized antibody or antigen-binding fragment of antibody 1F6 or 2F2. In some embodiments, the antibody or antigen-binding fragment comprises a polypeptide chain having the amino acid sequence of SEQ ID NO:6, SEQ ID NO:10, SEQ ID NO:14, SEQ ID NO:18, or amino acids 20-137 of SEQ ID NO:4. In some embodiments, the antibody or antigen-binding fragment comprises a polypeptide chain having the amino acid sequence of SEQ ID NO:24.

In some embodiments, the antibody or antigen-binding fragment comprises a polypeptide chain that is at least 80% identical to the amino acid sequence of SEQ ID NO:6, SEQ ID NO:10, SEQ ID NO:14, SEQ ID NO:18, or amino acids 20-137 of SEQ ID NO:4. In some embodiments, the antibody or antigen-binding fragment comprises a polypeptide chain that is at least 85% identical to the amino acid sequence of SEQ ID NO:6, SEQ ID NO:10, SEQ ID NO:14, SEQ ID NO:18, or amino acids 20-137 of SEQ ID NO:4. In some embodiments, the antibody or antigen-binding fragment comprises a polypeptide chain that is at least 90% identical to the amino acid sequence of SEQ ID NO:6, SEQ ID NO:10, SEQ ID NO:14, SEQ ID NO:18, or amino acids 20-137 of SEQ ID NO:4. In some embodiments, the antibody or antigen-binding fragment comprises a polypeptide chain that is at least 95% identical to the amino acid sequence of SEQ ID NO:6, SEQ ID NO:10, SEQ ID NO:14, SEQ ID NO:18, or amino acids 20-137 of SEQ ID NO:4. In some embodiments, the antibody or antigen-binding fragment comprises a polypeptide chain that is at least 99% identical to the amino acid sequence of SEQ ID NO:6, SEQ ID NO:10, SEQ ID NO:14, SEQ ID NO:18, or amino acids 20-137 of SEQ ID NO:4. In some embodiments, the polypeptide does not have the amino acid sequence of the heavy chain variable region of antibody 1F6 or 2F2.

In some embodiments, the antibody or antigen-binding fragment comprises a polypeptide chain that is at least 80% identical to the amino acid sequence of SEQ ID NO:24. In some embodiments, the antibody or antigen-binding fragment comprises a polypeptide chain that is at least 85% identical to the amino acid sequence of SEQ ID NO:24. In some embodiments, the antibody or antigen-binding fragment comprises a polypeptide chain that is at least 90% identical to the amino acid sequence of SEQ ID NO:24. In some embodiments, the antibody or antigen-binding fragment comprises a polypeptide chain that is at least 95% identical to the amino acid sequence of SEQ ID NO:24. In some embodiments, the antibody or antigen-binding fragment comprises a polypeptide chain that is at least 99% identical to the amino acid sequence of SEQ ID NO:24. In some embodiments, the polypeptide does not have the amino acid sequence of the light chain variable region of antibody 1F6 or 2F2.

In some embodiments, the anti-CD70 binding agent competes with monoclonal antibody 1F6 or 2F2 for binding to human CD70. In some embodiments, the CD70 binding agent does not induce an agonistic or antagonistic signal when binding to CD70 (e.g., does not stimulate proliferation). In some embodiments, the CD70 binding agent blocks binding of CD27 to CD70 by at least 20%, at least 30%, at least 40%, at least 50%, at least 60, at least 70%, at least 80% or at least 90%.

The CD70-binding agent can optionally include an antibody effector domain that mediates or stimulates an ADCC, ADCP and/or CDC response against a CD70-expressing target cell. The effector domain(s) can be, for example, an Fc domain or domains of an Ig molecule. Such a CD70-binding agent can exert a cytotoxic or cytostatic effect on CD70-expressing cancer cells, or exert a cytotoxic, cytostatic, or immunomodulatory effect on activated lymphocytes or dendritic cells, for example, in the treatment of a CD70-expressing cancer or an immunological disorder, respectively. Typically, the CD70-binding agent recruits and/or activates cytotoxic white blood cells (e.g., natural killer (NK) cells, phagocytotic cells (e.g., macrophages), and/or serum complement components).

The anti-CD70 antibody can be a humanized antibody, a single chain antibody, an scFv, a diabody, an Fab, a minibody, an scFv-Fc, an Fv, or the like. In some embodiments, a CD70 antigen-binding region can be joined to an effector domain or domains such as, for example, the hinge-$C_H2$-$C_H3$ domains of an immunoglobulin, or a portion or fragment of an effector domain(s) having effector function. Antigen-binding antibody fragments, including single-chain antibodies, can comprise, for example, the variable region(s) in combination with the entirety or a portion of an effector domain (e.g., a $C_H2$ and/or $C_H3$ domain alone or in combination with a $C_H1$, hinge and/or $C_L$ domain). Also, antigen-binding fragments can comprise any combination of effector domains. In some embodiments, the anti-CD70 antibody can be a single chain antibody comprising a CD70-binding variable region joined to hinge-$C_H2$-$C_H3$ domains.

The effector domains of the anti-CD70 antibody can be from any suitable human immunoglobulin isotype. For example, the ability of human immunoglobulin to mediate CDC and ADCC/ADCP is generally in the order of IgM≈IgG1≈IgG3>IgG2>IgG4 and IgG1≈IgG3>IgG2/IgM/IgG4, respectively. A CD70-binding polypeptide can be expressed as a recombinant fusion protein comprising of the appropriate constant domains to yield the desired effector function(s). Upon binding to target cells, the anti-CD70 antibodies or derivatives can trigger in vitro and in vivo target cell destruction through an antibody effector function, such as ADCC, CDC, and ADCP.

The CD70-binding agent optionally can be conjugated to a therapeutic agent, such as a cytotoxic, cytostatic or immunomodulatory agent. Suitable therapeutic agents are described herein.

In some embodiments, an anti-CD70 antibody can be chimeric, comprising a human or non-human Fc region or portion thereof. For example, the antibody can include a Fc domain or portion of non-human origin, e.g., rodent (e.g., mouse or rat), donkey, sheep, rabbit, goat, guinea pig, camelid, horse, chicken or monkey (e.g., macaque, rhesus or the like).

An anti-CD70 binding agent, such as an antibody, can be monospecific, bispecific, trispecific, or of greater multispecificity. Multispecific antibodies may be specific for different epitopes of CD70 and/or may be specific for both CD70 as well as for a heterologous protein. (See, e.g., PCT Publications WO 93/17715, WO 92/08802, WO 91/00360, and WO 92/05793; Tutt et al., 1991, J. Immunol. 147:60-69; U.S. Pat. Nos. 4,474,893; 4,714,681; 4,925,648; 5,573,920; and 5,601,819; Kostelny et al., 1992, J. Immunol. 148:1547-1553.) Multispecific antibodies, including bispecific and trispecific antibodies, useful for practicing the methods described herein are antibodies that immunospecifically bind to both CD70 (including but not limited to antibodies that have the CDRs of the monoclonal antibodies 2F2 and 1F6) and a second cell surface receptor or receptor complex that mediates ADCC, ADCP, and/or CDC, such as CD16/FcγRIII, CD64/FcγRI, killer inhibitory or activating receptors, or the complement control protein CD59. In some embodiments, the binding of the portion of the multispecific antibody to the second cell surface molecule or receptor complex may enhance the effector functions of the anti-CD70 antibody or other CD70 binding agent.

Anti-CD70 antibodies and derivatives thereof and other binding agents may also be described or specified in terms of their binding affinity to CD70. Typical binding affinities include those with a dissociation constant or Kd less than $5 \times 10^{-2}$ M, $10^{-2}$ M, $5 \times 10^{-3}$ M, $10^{-3}$ M, $5 \times 10^{-4}$ M, $10^{-4}$ M, $5 \times 10^{-5}$ M, $10^{-5}$ M, $5 \times 10^{-6}$ M, $10^{-6}$M, $5 \times 10^{-7}$ M, $10^{-7}$ M, $5 \times 10^{-8}$ M, $10^{-8}$ M, $5 \times 10^{-9}$ M, $10^{-9}$ M, $5 \times 10^{-10}$ M, $10^{-10}$ M, $5\times10^{-11}$ M, $10^{-11}$ M, $5\times10^{-12}$ M, $10^{-12}$ M, $5\times^{-13}$ M, $5\times10^{-14}$ M, $5\times10^{-14}$ M, $10^{-14}$ M, $5\times10^{-15}$ M, or $10^{-15}$ M.

The antibodies can be generated by methods known in the art. For example, monoclonal antibodies can be prepared using a wide variety of techniques including, e.g., the use of hybridoma, recombinant, and phage display technologies, or a combination thereof. Hybridoma techniques are generally discussed in, for example, Harlow et al., *Antibodies: A Laboratory Manual* (Cold Spring Harbor Laboratory Press, 2nd ed., 1988); and Hammerling et al., In *Monoclonal Antibodies and T-Cell Hybridomas*, pp. 563-681 (Elsevier, N.Y., 1981). Examples of phage display methods that can be used to make the anti-CD70 antibodies include, e.g., those disclosed in Hoogenboom and Winter, 1991, *J. Mol. Biol.* 227:381; Marks et al., 1991, *J. Mol. Biol.* 222:581; Quan and Carter, 2002, *The rise of monoclonal antibodies as therapeutics in Anti-IgE and Allergic Disease*, Jardieu and Fick Jr., eds., Marcel Dekker, New York, N.Y., Chapter 20, pp. 427-469; Brinkman et al., 1995, *J. Immunol. Methods* 182:41-50; Ames et al., 1995, *J. Immunol. Methods* 184:177-186; Kettleborough et al., 1994, *Eur. J. Immunol.* 24:952-958; Persic et al., 1997, *Gene* 187:9-18; Burton et al., 1994, *Advances in Immunology* 57:191-280; PCT Application No. PCT/GB91/01134; PCT Publications WO 90/02809, WO 91/10737, WO 92/01047, WO 92/18619, WO 93/11236, WO 95/15982, WO 95/20401, and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108 (the disclosures of which are incorporated by reference herein).

Examples of techniques that can be used to produce single-chain antibodies include those described in U.S. Pat. Nos. 4,946,778 and 5,258,498; Huston et al., 1991, *Methods in Enzymology* 203:46-88; Shu et al., 1993, *Proc. Natl. Acad. Sci. USA* 90:7995-7999; and Skerra et al., 1988, *Science* 240:1038-1040.

Methods for making bispecific antibodies are known in the art. Traditional production of full-length bispecific antibodies is based on the coexpression of two immunoglobulin heavy chain-light chain pairs, where the two chains have different specificities (see, e.g., Milstein et al., 1983, Nature 305:537-39). Because of the random assortment of immunoglobulin heavy and light chains, these hybridomas (quadromas) produce a potential mixture of 10 different antibody molecules, of which some have the correct bispecific structure. Similar procedures are disclosed in International Publication No. WO 93/08829, and in Traunecker et al., 1991, EMBO J. 10:3655-59.

According to a different approach, antibody variable domains with the desired binding specificities (antibody-antigen combining sites) are fused to immunoglobulin constant domain sequences. The fusion typically is with an immunoglobulin heavy chain constant domain, comprising at least part of the hinge, $C_H2$, and $C_H3$ regions. In some embodiments, the fusion includes a first heavy-chain constant region ($C_H1$) containing the site necessary for light chain binding, present in at least one of the fusions. Nucleic acids with sequences encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In an embodiment of this approach, the bispecific antibodies have a hybrid immunoglobulin heavy chain with a first binding specificity in one arm, and a hybrid immunoglobulin heavy chain-light chain pair (providing a second binding specificity) in the other arm. This asymmetric structure facilitates the separation of the desired bispecific compound from unwanted immunoglobulin chain combinations, as the presence of an immunoglobulin light chain in only one half of the bispecific molecule provides for a facile way of separation (see, e.g., International Publication No. WO 94/04690, which is incorporated herein by reference in its entirety).

For further discussion of bispecific antibodies see, for example, Suresh et al., 1986, *Methods in Enzymology* 121:210; Rodrigues et al., 1993, *J. Immunology* 151:6954-61; Carter et al., 1992, *Bio/Technology* 10:163-67; Carter et al., 1995, *J. Hematotherapy* 4:463-70; Merchant et al., 1998, *Nature Biotechnology* 16:677-81. Using such techniques, bispecific antibodies can be prepared for use in the treatment or prevention of disease as defined herein.

Bifunctional antibodies are also described in European Patent Publication No. EPA 0 105 360. As disclosed in this reference, hybrid or bifunctional antibodies can be derived either biologically, i.e., by cell fusion techniques, or chemically, especially with cross-linking agents or disulfide-bridge forming reagents, and may comprise whole antibodies or fragments thereof. Methods for obtaining such hybrid antibodies are disclosed for example in International Publication WO 83/03679 and European Patent Publication No. EPA 0 217 577, both of which are incorporated herein by reference.

In some embodiments, framework residues in the human framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., U.S. Pat. No. 5,585,089; Riechmann et al., 1988, *Nature* 332:323.) Antibodies can be humanized using a variety of techniques known in the art including, for example, CDR-grafting (see, e.g., EP 0 239 400; PCT Publication WO 91/09967; U.S. Pat. Nos. 5,225,539; 5,530,101; and 5,585,089), veneering or resurfacing (see, e.g., EP 0 592 106; EP 0 519 596; Padlan, 1991, *Molecular Immunology* 28(4/5):489-498; Studnicka et al., 1994, *Protein Engineering* 7(6):805-814; Roguska et al., 1994, *Proc. Natl. Acad. Sci. USA* 91:969-973), and chain shuffling (see, e.g., U.S. Pat. No. 5,565,332) (all of these references are incorporated by reference herein).

Humanized monoclonal antibodies can be produced by recombinant DNA techniques known in the art, for example using methods described in International Publication No. WO 87/02671; European Patent Publication No. 0 184 187; European Patent Publication No. 0 171 496; European Patent Publication No. 0 173 494; International Publication No. WO 86/01533; U.S. Pat. No. 4,816,567; European Patent Publication No. 0 012 023; Berter et al., 1988, *Science* 240:1041-43; Liu et al., 1987, *Proc. Natl. Acad. Sci. USA* 84:3439-43; Liu et al., 1987, *J. Immunol.* 139:3521-26; Sun et al., 1987, *Proc. Natl. Acad. Sci. USA* 84:214-18; Nishimura et al., 1987, *Cancer. Res.* 47:999-1005; Wood et al., 1985, *Nature* 314:446-449; Shaw et al., 1988, *J. Natl.*

Cancer Inst. 80:1553-59; Morrison, 1985, Science 229: 1202-07; Oi et al., 1986, BioTechniques 4:214; U.S. Pat. No. 5,225,539; Jones et al., 1986, Nature 321:552-25; Verhoeyan et al., 1988, Science 239:1534; and Beidler et al., 1988, J. Immunol. 141:4053-60; each of which is incorporated herein by reference in its entirety.

As set forth supra, a CD70 binding agent can be a derivative of an anti-CD70 antibody. Generally, an anti-CD70 antibody derivative comprises an anti-CD70 antibody (including e.g., an antigen-binding fragment or conservatively substituted polypeptides) and at least one polypeptide region or other moiety heterologous to the anti-CD70 antibody. For example, an anti-CD70 antibody can be modified, e.g., by the covalent attachment of any type of molecule. Typical modifications include, e.g., glycosylation, acetylation, pegylation, phosphorylation, amidation, derivatization by known protecting/blocking groups, proteolytic cleavage, linkage to a cellular ligand (e.g., an albumin-binding molecule) or other protein, and the like. Any of numerous chemical modifications may be carried out by known techniques, including, but not limited to specific chemical cleavage, acetylation, formylation, metabolic synthesis of tunicamycin, etc.

In some embodiments, the covalent attachment does not interfere with effector function, e.g., prevent the antibody derivative from specifically binding to CD70 via the antigen-binding region or region derived therefrom, or the effector domains(s) from specifically binding Fc receptor.

In some embodiments, the antibody derivative is a multimer, such as, for example, a dimer, comprising one or more monomers, where each monomer includes (i) an antigen-binding region of an anti-CD70 antibody, or a polypeptide region derived therefrom (such as, e.g., by conservative substitution of one or more amino acids), and (ii) a multimerizing (e.g., dimerizing) polypeptide region, such that the antibody derivative forms multimers (e.g., homodimers) that specifically bind to CD70. In typical embodiments, an antigen-binding region of an anti-CD70 antibody, or a polypeptide region derived therefrom, is recombinantly or chemically fused with a heterologous protein, wherein the heterologous protein comprises a dimerization or multimerization domain. Prior to administration of the antibody derivative to a subject for the purpose of treating or preventing immunological disorders or CD70-expressing cancers, the derivative is subjected to conditions that allow formation of a homodimer or heterodimer. A heterodimer, as used herein, may comprise identical dimerization domains but different CD70 antigen-binding regions, identical CD70 antigen-binding regions but different dimerization domains, or different CD70 antigen-binding regions and dimerization domains.

Typical dimerization domains are those that originate from transcription factors. In one embodiment, the dimerization domain is that of a basic region leucine zipper ("bZIP") (see Vinson et al., 1989, Science 246:911-916). Useful leucine zipper domains include, for example, those of the yeast transcription factor GCN4, the mammalian transcription factor CCAAT/enhancer-binding protein C/EBP, and the nuclear transform in oncogene products, Fos and Jun. (See, e.g., Landschultz et al., 1988, Science 240:1759-64; Baxevanis and Vinson, 1993, Curr. Op. Gen. Devel. 3:278-285; O'Shea et al., 1989, Science 243:538-542.) In another embodiment, the dimerization domain is that of a basic-region helix-loop-helix ("bHLH") protein. (See, e.g., Murre et al., 1989, Cell 56:777-783. See also Davis et al., 1990, Cell 60:733-746; Voronova and Baltimore, 1990, Proc. Natl. Acad. Sci. USA 87:4722-26.) Particularly useful hHLH proteins are myc, max, and mac.

In yet other embodiments, the dimerization domain is an immunoglobulin constant region such as, for example, a heavy chain constant region or a domain thereof (e.g., a $C_H1$ domain, a $C_H2$ domain, and/or a $C_H3$ domain). (See, e.g., U.S. Pat. Nos. 5,155,027; 5,336,603; 5,359,046; and 5,349,053; EP 0 367 166; and WO 96/04388.)

Heterodimers are known to form between Fos and Jun (Bohmann et al., 1987, Science 238:1386-1392), among members of the ATF/CREB family (Hai et al., 1989, Genes Dev. 3:2083-2090), among members of the C/EBP family (Cao et al., 1991, Genes Dev. 5:1538-52; Williams et al., 1991, Genes Dev. 5:1553-67; Roman et al., 1990, Genes Dev. 4:1404-15), and between members of the ATF/CREB and Fos/Jun families (Hai and Curran, 1991, Proc. Natl. Acad. Sci. USA 88:3720-24). Therefore, when a CD70-binding protein is administered to a subject as a heterodimer comprising different dimerization domains, any combination of the foregoing may be used.

In other embodiments, an anti-CD70 antibody derivative is an anti-CD70 antibody conjugated to a second antibody (an "antibody heteroconjugate") (see, e.g., U.S. Pat. No. 4,676,980). Heteroconjugates useful for practicing the present methods comprise an antibody that binds to CD70 (e.g., an antibody that has the CDRs and/or heavy chains of the monoclonal antibodies 2F2 or 1F6) and an antibody that binds to a surface receptor or receptor complex that mediates ADCC, phagocytosis, and/or CDC, such as CD16/FcgRIII, CD64/FcgRI, killer cell activating or inhibitory receptors, or the complement control protein CD59. In a typical embodiment, the binding of the portion of the multispecific antibody to the second cell surface molecule or receptor complex enhances the effector functions of an anti-CD70 antibody. In other embodiments, the antibody can be a therapeutic agent. Suitable antibody therapeutic agents are described herein.

In some embodiments, the anti-CD70 antibody or derivative thereof competitively inhibits binding of mAb 1F6 or 2F2 to CD70, as determined by any method known in the art for determining competitive binding (such as e.g., the immunoassays described herein). In typical embodiments, the antibody competitively inhibits binding of 1F6 or 2F2 to CD70 by at least 50%, at least 60%, at least 70%, or at least 75%. In other embodiments, the antibody competitively inhibits binding of 1F6 or 2F2 to CD70 by at least 80%, at least 85%, at least 90%, or at least 95%.

Antibodies can be assayed for specific binding to CD70 by any of various known methods. Immunoassays which can be used include, for example, competitive and non-competitive assay systems using techniques such as Western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, and protein A immunoassays. Such assays are routine and well-known in the art. (See, e.g., Ausubel et al., eds., Short Protocols in Molecular Biology (John Wiley and Sons, Inc., New York, 4th ed. 1999); Harlow and Lane, Using Antibodies: A Laboratory Manual (Cold Spring Harbor Laboratory Press, Cold Spring Harbor, N.Y., 1999.)

Further, the binding affinity of an antibody to CD70 and the off-rate of an antibody CD70 interaction can be determined by competitive binding assays. One example of a competitive binding assay is a radioimmunoassay comprising the incubation of labeled CD70 (e.g., $^3H$ or $^{125}I$) with the antibody of interest in the presence of increasing amounts of unlabeled CD70, and the detection of the antibody bound to the labeled CD70. The affinity of the antibody for CD70 and the binding off-rates can then be determined from the data by Scatchard plot analysis. Competition with a second antibody (such as e.g., mAb 1F6 or 2F2) can also be determined using radioimmunoassays. In this case, CD70 is incubated with the antibody of interest conjugated to a labeled compound (e.g., $^3$H or $^{125}$I) in the presence of increasing amounts of an unlabeled second antibody. Alternatively, the binding affinity of an antibody to CD70 and the on- and off-rates of an antibody-CD70 interaction can be determined by surface plasmon resonance. In some embodiments, the anti-CD70 antibodies or derivatives thereof can be targeted to and accumulate on the membrane of a CD70-expressing cell.

Anti-CD70 antibodies and derivatives thereof can be produced by methods known in the art for the synthesis of proteins, typically, e.g., by recombinant expression techniques. Recombinant expression of an antibody or derivative thereof that binds to CD70 typically includes construction of an expression vector containing a nucleic acid that encodes the antibody or derivative thereof. A vector for the production of the protein molecule may be produced by recombinant DNA technology using techniques known in the art. Standard techniques such as, for example, those described in Sambrook and Russell, *Molecular Cloning: A Laboratory Manual* (Cold Spring Harbor Laboratory Press, Cold Spring Harbor, N.Y., 3rd ed., 2001); Sambrook et al., *Molecular Cloning: A Laboratory Manual* (Cold Spring Harbor Laboratory Press, Cold Spring Harbor, N.Y., 2nd ed., 1989); *Short Protocols in Molecular Biology* (Ausubel et al., John Wiley and Sons, New York, 4th ed., 1999); and Glick and Pasternak, *Molecular Biotechnology: Principles and Applications of Recombinant DNA* (ASM Press, Washington, D.C., 2nd ed., 1998) can be used for recombinant nucleic acid methods, nucleic acid synthesis, cell culture, transgene incorporation, and recombinant protein expression.

For example, for recombinant expression of an anti-CD70 antibody, an expression vector may encode a heavy or light chain thereof, or a heavy or light chain variable domain, operably linked to a promoter. An expression vector may include, for example, the nucleotide sequence encoding the constant region of the antibody molecule (see, e.g., PCT Publication WO 86/05807; PCT Publication WO 89/01036; and U.S. Pat. No. 5,122,464), and the variable domain of the antibody may be cloned into such a vector for expression of the entire heavy or light chain. The expression vector is transferred to a host cell by conventional techniques, and the transfected cells are then cultured by conventional techniques to produce the anti-CD70 antibody. In typical embodiments for the expression of double-chained antibodies, vectors encoding both the heavy and light chains can be co-expressed in the host cell for expression of the entire immunoglobulin molecule.

A variety of prokaryotic and eukaryotic host-expression vector systems can be utilized to express an anti-CD70 antibody or derivative thereof. Typically, eukaryotic cells, particularly for whole recombinant anti-CD70 antibody molecules, are used for the expression of the recombinant protein. For example, mammalian cells such as Chinese hamster ovary cells (CHO), in conjunction with a vector such as the major intermediate early gene promoter element from human cytomegalovirus, is an effective expression system for the production of anti-CD70 antibodies and derivatives thereof (see, e.g., Foecking et al., 1986, *Gene* 45:101; Cockett et al., 1990, *Bio/Technology* 8:2).

Other host-expression systems include, for example, plasmid-based expression systems in bacterial cells (see, e.g., Ruther et al., 1983, EMBO 1, 2:1791; Inouye and Inouye, 1985, *Nucleic Acids Res.* 13:3101-3109; Van Heeke and Schuster, 1989, *J. Biol. Chem.* 24:5503-5509); insect systems such as, e.g., the use of *Autographa californica* nuclear polyhedrosis virus (AcNPV) expression vector in *Spodoptera frugiperda* cells; and viral-based expression systems in mammalian cells, such as, e.g., adenoviral-based systems (see, e.g., Logan and Shenk, 1984, *Proc. Natl. Acad. Sci. USA* 81:355-359; Bittner et al., 1987, *Methods in Enzymol.* 153:51-544).

In addition, a host cell strain can be chosen that modulates the expression of the inserted sequences, or modifies and processes the gene product in the specific fashion desired. Appropriate cell lines or host systems can be chosen to ensure the correct modification and processing (e.g., glycosylation, phosphorylation, and cleavage) of the protein expressed. To this end, eukaryotic host cells which possess the cellular machinery for proper processing of the primary transcript and gene product can be used. Such mammalian host cells include, for example, CHO, VERO, BHK, HeLa, COS, MDCK, 293, 3T3, and W138.

A stable expression system is typically used for long-term, high-yield production of recombinant anti-CD70 antibody or derivative thereof or other CD70 binding agent. For example, cell lines that stably express the anti-CD70 antibody or derivative thereof can be engineered by transformation of host cells with DNA controlled by appropriate expression control elements (e.g., promoter and enhancer sequences, transcription terminators, polyadenylation sites) and a selectable marker, followed by growth of the transformed cells in a selective media. The selectable marker confers resistance to the selection and allows cells to stably integrate the DNA into their chromosomes and grow to form foci which in turn can be cloned and expanded into cell lines. A number of selection systems can be used, including, for example, the herpes simplex virus thymidine kinase, hypoxanthineguanine phosphoribosyltransferase, and adenine phosphoribosyltransferase genes, which can be employed in tk$^-$, hgprt$^-$ or aprt$^-$ cells, respectively. Also, antimetabolite resistance can be used as the basis of selection for the following genes: dhfr, which confers resistance to methotrexate; gpt, which confers resistance to mycophenolic acid; neo, which confers resistance to the aminoglycoside G-418; and hygro, which confers resistance to hygromycin. Methods commonly known in the art of recombinant DNA technology can be routinely applied to select the desired recombinant clone, and such methods are described, for example, in *Current Protocols in Molecular Biology* (Ausubel et al. eds., John Wiley and Sons, N.Y., 1993); Kriegler, *Gene Transfer and Expression, A Laboratory Manual* (Stockton Press, N.Y., 1990); *Current Protocols in Human Genetics* (Dracopoli et al. eds., John Wiley and Sons, N.Y., 1994, Chapters 12 and 13); and Colberre-Garapin et al., 1981, *J. Mol. Biol.* 150:1.

The expression levels of an antibody or derivative can be increased by vector amplification. (See generally, e.g., Bebbington and Hentschel, *The Use of Vectors Based on Gene Amplification for the Expression of Cloned Genes in Mammalian Cells in DNA Cloning*, Vol. 3 (Academic Press, New York, 1987).) When a marker in the vector system expressing an anti-CD70 antibody or derivative thereof is amplifiable, an increase in the level of inhibitor present in host cell culture media will select host cells that have increased copy number of a marker gene conferring resistance to the inhibitor. The copy number of an associated antibody gene will also be increased, thereby increasing expression of the antibody or derivative thereof (see Crouse et al., 1983, *Mol. Cell. Biol.* 3:257).

Where the anti-CD70 antibody comprises both a heavy and a light chain or derivatives thereof, the host cell may be co-transfected with two expression vectors, the first vector encoding the heavy chain protein and the second vector encoding the light chain protein. The two vectors may contain identical selectable markers which enable equal expression of heavy and light chain proteins. Alternatively, a single vector may be used which encodes, and is capable of expressing, both heavy and light chain proteins. In such situations, the light chain is typically placed before the heavy chain to avoid an excess of toxic free heavy chain (see Proudfoot, 1986, *Nature* 322:52; Kohler, 1980, *Proc. Natl. Acad. Sci. USA* 77:2197). The coding sequences for the heavy and light chains may comprise cDNA or genomic DNA.

Once an anti-CD70 antibody or derivative thereof has been produced (e.g., by an animal, chemical synthesis, or recombinant expression), it can be purified by any suitable method for purification of proteins, including, for example, by chromatography (e.g., ion exchange or affinity chromatography (such as, for example, Protein A chromatography for purification of antibodies having an intact Fc region)), centrifugation, differential solubility, or by any other standard technique for the purification of proteins. An anti-CD70 antibody or derivative thereof can, for example, be fused to a marker sequence, such as a peptide, to facilitate purification by affinity chromatography. Suitable marker amino acid sequences include, e.g., a hexa-histidine peptide, such as the tag provided in a pQE vector (QIAGEN, Inc., Chatsworth, Calif., 91311), and the "HA" tag, which corresponds to an epitope derived from the influenza hemagglutinin protein (Wilson et al., 1984, *Cell* 37:767), and the "flag" tag.

Once an anti-CD70 antibody or derivative thereof is produced, its ability to exert a cytostatic or cytotoxic effect on CD70-expressing cancer cells or an immunomodulatory effect on a CD70-expressing immune cell is determined by the methods described infra or as known in the art.

To minimize activity of the anti-CD70 antibody outside the activated immune cells or CD70-expressing cancer cells, an antibody that specifically binds to cell membrane-bound CD70, but not to soluble CD70, can be used, so that the anti-CD70 antibody is concentrated at the cell surface of the activated immune cell or CD70-expressing cancer cell.

Typically, the anti-CD70 antibody or derivative is substantially purified (e.g., substantially free from substances that limit its effect or produce undesired side-effects). In some embodiments, the anti-CD70 antibody or derivative is at least about 40% pure, at least about 50% pure, or at least about 60% pure. In some embodiments, the anti-CD70 antibody or derivative is at least about 60-65%, 65-70%, 70-75%, 75-80%, 80-85%, 85-90%, 90-95%, or 95-98% pure. In some embodiments, the anti-CD70 antibody or derivative is approximately 99% pure.

III. OTHER CD70-BINDING AGENTS

Further CD70-binding agents include fusion proteins (i.e., proteins that are recombinantly fused or chemically conjugated, including both covalent and non-covalent conjugation) to heterologous proteins (of typically at least 10, 20, 30, 40, 50, 60, 70, 80, 90 or at least 100 amino acids). Such CD70-binding agents can include a portion that binds to CD70 and an immunoglobulin effector domain or a functional equivalent thereof. As used herein, a functional equivalent of immunoglobulin effector domain binds to an Fc receptor on an immune cell with phagocytic or lytic activity or by binding of an Fc effector domain(s) to components of the complement system. The fusion protein does not necessarily need to be direct, but may occur through linker sequences.

For example, a CD70-binding agent can be produced recombinantly by fusing the coding region of one or more of the CDRs or the variable region of an anti-CD70 antibody in frame with a sequence coding for a heterologous protein. The heterologous protein can include, for example, an effector domain, a functional equivalent thereof or other functional domain to provide one or more of the following characteristics: promote stable expression; provide a means of facilitating high yield recombinant expression; provide a cytostatic, cytotoxic or immunomodulatory activity; and/or provide a multimerization domain.

In some embodiments, the CD70-binding agent can include one or more CDRs from an antibody that binds to CD70 and depletes or inhibits the proliferation of CD70-expressing cells alone, without conjugation to a cytotoxic agent.

IV. METHODS TO IMPROVE EFFECTOR FUNCTIONS OF ANTI-CD70-TARGETING AGENTS

In some embodiments, the effector function of a CD70-binding agent can be augmented by improving its effector functions using one or more antibody engineering approaches known in the art. Illustrative, non-limiting examples for such approaches are provided below.

ADCC and ADCP are mediated through the interaction of cell-bound antibodies with Fcγ receptors (FcγR) expressed on effector cells. Both the glycosylation status and primary amino acid sequence of the IgG Fc region have functional effects on the Fcγ-FcγR interaction. A stronger Fcγ-FcγR interaction is associated with better target cell killing by effector cells.

Oligosaccharides covalently attached to the conserved Asn297 are involved in the Fc region of an IgG to bind FcγR (Lund et al., 1996, *J. Immunol.* 157:4963-69; Wright and Morrison, 1997, *Trends Biotechnol.* 15:26-31). Engineering of this glycoform on IgG can significantly improve IgG-mediated ADCC. Addition of bisecting N-acetylglucosamine modifications (Umana et al., 1999, *Nat. Biotechnol.* 17:176-180; Davies et al., 2001, *Biotech. Bioeng.* 74:288-94) to this glycoform or removal of fucose (Shields et al., 2002, *J. Biol. Chem.* 277:26733-40; Shinkawa et al., 2003, *J. Biol. Chem.* 278:6591-604; Niwa et al., 2004, *Cancer Res.* 64:2127-33) from this glycoform are two examples of IgG Fc engineering that improves the binding between IgG Fc and FcγR, thereby enhancing Ig-mediated ADCC activity.

A systemic substitution of solvent-exposed amino acids of human IgG1 Fc region has generated IgG variants with altered FcγR binding affinities (Shields et al., 2001, *J. Biol. Chem.* 276:6591-604). When compared to parental IgG1, a subset of these variants involving substitutions at Thr256/Ser298, Ser298/Glu333, Ser298/Lys334, or Ser298/Glu333/Lys334 to Ala demonstrate increased in both binding affinity toward FcγR and ADCC activity (Shields et al., 2001, *J. Biol. Chem.* 276:6591-604; Okazaki et al., 2004, *J. Mol. Biol.* 336:1239-49).

Antibody-mediated CDC begins with the binding of C1q to cell bound IgG molecules. Specific amino acid residues on human IgG1 responsible for C1q binding and species-specific differences of C1q binding have been reported (Idusogie et al., 2000, *J. Immunol.* 164:4178-4184). Complement fixation activity of antibodies have been improved by substitutions at Lys326 and Glu333; for example, such substitutions can improve both C1q binding and CDC activity of the human IgG1 antibody rituximab (Idusogie et al., 2001, *J. Immunol.* 166:2571-2575). The same substitutions on a human IgG2 backbone can convert an antibody isotype that binds poorly to C1q and is severely deficient in complement activation activity to one that can both bind C1q and mediate CDC (Idusogie et al., 2001, *J. Immunol.* 166:2571-75). Several other methods have also been applied to improve complement fixation activity of antibodies. For example, the grafting of an 18-amino acid carboxyl-terminal tail piece of IgM to the carboxyl-termini of IgG greatly enhances their CDC activity. This is observed even with IgG4, which normally has no detectable CDC activity (Smith et al., 1995, *J. Immunol.* 154:2226-36). Also, substituting Ser444 located close to the carboxy-terminal of IgG1 heavy chain with Cys induced tail-to-tail dimerization of IgG1 with a 200-fold increase of CDC activity over monomeric IgG1 (Shopes et al., 1992, *J. Immunol.* 148: 2918-22). In addition, a bispecific diabody construct with specificity for C1q also confers CDC activity (Kontermann et al., 1997, *Nat. Biotech.* 15:629-31).

The in vivo half-life of an antibody can also impact on its effector functions. In some embodiments, it is desirable to increase or decrease the half-life of an antibody to modify its therapeutic activities. FcRn is a receptor that is structurally similar to MHC Class I antigen that non-covalently associates with β2-microglobulin. FcRn regulates the catabolism of IgGs and their transcytosis across tissues (Ghetie and Ward, 2000, *Annu. Rev. Immunol.* 18:739-766; Ghetie and Ward, 2002, *Immunol. Res.* 25:97-113). The IgG-FcRn interaction takes place at pH 6.0 (pH of intracellular vesicles) but not at pH 7.4 (pH of blood); this interaction enables IgGs to be recycled back to the circulation (Ghetie and Ward, 2000, *Ann. Rev. Immunol.* 18:739-766; Ghetie and Ward, 2002, *Immunol. Res.* 25:97-113). The region on human $IgG_1$ involved in FcRn binding has been mapped (Shields et al., 2001, *J. Biol. Chem.* 276:6591-604). Alanine substitutions at positions Pro238, Thr256, Thr307, Gln311, Asp312, Glu380, Glu382, or Asn434 of human $IgG_1$ enhance FcRn binding (Shields et al., 2001, *J. Biol. Chem.* 276:6591-604). $IgG_1$ molecules harboring these substitutions are expected to have longer serum half-lives. Consequently, these modified $IgG_1$ molecules may be able to carry out their effector functions, and hence exert their therapeutic efficacies, over a longer period of time compared to unmodified $IgG_1$.

V. ASSAYS FOR CYTOTOXIC, CYTOSTATIC, AND IMMUNOMODULATORY ACTIVITIES

Methods of determining whether an antibody mediates effector function against a target cell are known. Illustrative examples of such methods are described infra.

For determining whether an anti-CD70 antibody or derivative mediates antibody-dependent cellular cytotoxicity against activated immune cells or CD70-expressing cancer cells, an assay that measures target cell death in the presence of antibody and effector immune cells may be used. An assay used to measure this type of cytotoxicity can be based on determination of $^{51}Cr$ release from metabolically-labeled targets cells after incubation in the presence of effector cells and target-specific antibody (see, e.g., Perussia and Loza, 2000, *Methods in Molecular Biology* 121:179-92; and "$^{51}Cr$ Release Assay of Antibody-Dependent Cell-Mediated Cytotoxicity (ADCC)" in *Current Protocols in Immunology*, Coligan et al. eds., Wiley and Sons, 1993). For example, activated immune cells (e.g., activated lymphocytes) or CD70-expressing cancer cells labeled with $Na_2{}^{51}CrO_4$ and plated at a density of 5,000 cells per well of a 96-well plate can be treated with varying concentrations of anti-CD70 antibody for 30 minutes then mixed with normal human peripheral blood mononuclear cells (PBMC) for 4 hours. The membrane disruption that accompanies target cell death releases $^{51}Cr$ into the culture supernatant which may be collected and assessed for radioactivity as a measure of cytotoxic activity. Other assays to measure ADCC may involve nonradioactive labels or be based on induced release of specific enzymes. For example, a non-radioactive assay based on time-resolved fluorometry is commercially available (Delphia, Perkin Elmer). This assay is based on loading target cells with an acetoxymethyl ester of fluorescence enhancing ligand (BATDA) that penetrates the cell membrane then hydrolyses to form a membrane impermeable hydrophilic ligand (TDA). When mixed with target specific antibody and PBMC effector cells, TDA is released from lysed cells and is available to form a highly fluorescent chelate when mixed with Europium. The signal, measured with a time-resolved fluorometer, correlates with the amount of cell lysis.

To determine whether an anti-CD70 antibody or derivative mediates antibody-dependent cellular phagocytosis against activated immune cells or CD70-expressing cancer cells, an assay that measures target cell internalization by effector immune cells (e.g., fresh cultured macrophages or established macrophage-like cell line) may be used (see, e.g., Munn and Cheung, 1990, *J. Exp. Med.* 172:231-37; Keler et al., 2000, *J. Immunol.* 164:5746-52; Akewanlop et al., 2001, *Cancer Res.* 61:4061-65). For example, target cells may be labeled with a lipophilic membrane dye such as PKH67 (Sigma), coated with target-specific antibody, and mixed with effector immune cells for 4-24 hours. The effector cells may then be identified by counterstaining with a fluorochrome-labeled antibody specific for a phagocytic cell surface marker (e.g., CD14) and the cells analyzed by two-color flow cytometry or fluorescence microscopy. Dual-positive cells represent effector cells that have internalized target cells. For these assays, effector cells may be monocytes derived from PBMC that have been differentiated into macrophages by culture for 5-10 days with M-CSF or GM-CSF (see, e.g., Munn and Cheung, supra). Human macrophage-like cell lines U937 (Larrick et al., 1980, *J. Immunology* 125:6-12) or THP-1 (Tsuchiya et al., 1980, *Int. J. Cancer* 26:171-76) which are available from ATCC may be used as an alternative phagocytic cell source.

Methods of determining whether an antibody mediates complement-dependent cytotoxicity upon binding to target cells are also known. The same methods can be applied to determine whether a CD70-binding agent mediates CDC on activated immune cells or CD70-expressing cancer cells. Illustrative examples of such methods are described infra.

The source of active complement can either be normal human serum or purified from laboratory animal including rabbits. In a standard assay, a CD70-binding agent is incubated with CD70-expressing activated immune cells (e.g., activated lymphocytes) or CD70-expressing cancer cells in the presence of complement. The ability of such CD70-binding agent to mediate cell lysis can be determined by several readouts. In one example, a $Na^{51}CrO_4$ release assay is used. In this assay, target cells are labeled with $Na^{51}CrO_4$. Unincorporated $Na^{51}CrO_4$ is washed off and cells are plated at a suitable density, typically between 5,000 to 50,000 cells/well, in a 96-well plate. Incubation with the CD70-binding agent in the presence of normal serum or purified complement typically last for 2-6 hours at 37° C. in a 5% $CO_2$ atmosphere. Released radioactivity, indicating cell lysis, is determined in an aliquot of the culture supernatant by gamma ray counting. Maximum cell lysis is determined by releasing incorporated $Na^{51}CrO_4$ by detergent (0.5-1% NP-40 or Triton X-100) treatment. Spontaneous background cell lysis is determined in wells where only complement is present without any CD70-binding agents. Percentage cell lysis is calculated as (CD70-binding agent-induced lysis–spontaneous lysis)/maximum cell lysis. The second readout is a reduction of metabolic dyes, e.g., Alamar Blue, by viable cells. In this assay, target cells are incubated with CD70-binding agent with complement and incubated as described above. At the end of incubation, 1/10 volume of Alamar Blue (Biosource International, Camarillo, Calif.) is added. Incubation is continued for up to 16 hours at 37° C. in a 5% $CO_2$ atmosphere. Reduction of Alamar Blue as an indication of metabolically active viable cells is determined by fluorometric analysis with excitation at 530 nm and emission at 590 nm. The third readout is cellular membrane permeability to propidium iodide (PI). Formation of pores in the plasma membrane as a result of complement activation facilitates entry of PI into cells where it will diffuse into the nuclei and bind DNA. Upon binding to DNA, PI fluorescence in the 600 nm significantly increases. Treatment of target cells with CD70-binding agent and complement is carried out as described above. At end of incubation, PI is added to a final concentration of 5 μg/ml. The cell suspension is then examined by flow cytometry using a 488 nm argon laser for excitation. Lysed cells are detected by fluorescence emission at 600 nm.

VI. ANIMAL MODELS OF IMMUNOLOGICAL DISORDERS OR CD70-EXPRESSING CANCERS

The anti-CD70 binding agents, e.g., antibodies or derivatives, can be tested or validated in animal models of immunological disorders or CD70-expressing cancers. A number of established animal models of immunological disorders or CD70-expressing cancers are known to the skilled artisan, any of which can be used to assay the efficacy of the anti-CD70 antibody or derivative. Non-limiting examples of such models are described infra.

Examples for animal models of systemic and organ-specific autoimmune diseases including diabetes, lupus, systemic sclerosis, Sjögren's Syndrome, experimental autoimmune encephalomyelitis (multiple sclerosis), thyroiditis, myasthenia gravis, arthritis, uveitis, and inflammatory bowel disease have been described by Bigazzi, "Animal Models of Autoimmunity: Spontaneous and Induced," in *The Autoimmune Diseases* (Rose and Mackay eds., Academic Press, 1998) and in "Animal Models for Autoimmune and Inflammatory Disease," in *Current Protocols in Immunology* (Coligan et al. eds., Wiley and Sons, 1997).

Allergic conditions, e.g., asthma and dermatitis, can also be modeled in rodents. Airway hypersensitivity can be induced in mice by ovalbumin (Tomkinson et al., 2001, *J. Immunol.* 166:5792-800) or *Schistosoma mansoni* egg antigen (Tesciuba et al., 2001, *J. Immunol.* 167:1996-2003). The Nc/Nga strain of mice show marked increase in serum IgE and spontaneously develop atopic dermatitis-like lesions (Vestergaard et al., 2000, *Mol. Med. Today* 6:209-10; Watanabe et al., 1997, *Int. Immunol.* 9:461-66; Saskawa et al., 2001, *Int. Arch. Allergy Immunol.* 126:239-47).

Injection of immuno-competent donor lymphocytes into a lethally irradiated histo-incompatible host is a classical approach to induce GVHD in mice. Alternatively, the parent B6D2F1 murine model provides a system to induce both acute and chronic GVHD. In this model the B6D2F1 mice are F1 progeny from a cross between the parental strains of C57BL/6 and DBA/2 mice. Transfer of DBA/2 lymphoid cells into non-irradiated B6D2F1 mice causes chronic GVHD, whereas transfer of C57BL/6, C57BL/10 or B10.D2 lymphoid cells causes acute GVHD (Slayback et al., 2000, *Bone Marrow Transpl.* 26:931-938; Kataoka et al., 2001, *Immunology* 103:310-318).

Additionally, both human hematopoietic stem cells and mature peripheral blood lymphoid cells can be engrafted into SCID mice, and these human lympho-hematopoietic cells remain functional in the SCID mice (McCune et al., 1988, *Science* 241:1632-1639; Kamel-Reid and Dick, 1988, *Science* 242:1706-1709; Mosier et al., 1988, *Nature* 335: 256-259). This has provided a small animal model system for the direct testing of potential therapeutic agents on human lymphoid cells. (See, e.g., Tournoy et al., 2001, *J. Immunol.* 166:6982-6991).

Moreover, small animal models to examine the in vivo efficacies of the anti-CD70 antibodies or derivatives can be created by implanting CD70-expressing human tumor cell lines into appropriate immunodeficient rodent strains, e.g., athymic nude mice or SCID mice. Examples of CD70-expressing human lymphoma cell lines include, for example, Daudi (Ghetie et al., 1994, *Blood* 83:1329-36; Ghetie et al., 1990, *Int. J. Cancer* 15:481-85; de Mont et al., 2001, *Cancer Res.* 61:7654-59), HS-Sultan (Cattan and Maung, 1996, *Cancer Chemother. Pharmacol.* 38:548-52; Cattan and Douglas, 1994, *Leuk. Res.* 18:513-22), Raji (Ochakovskaya et al., 2001, *Clin. Cancer Res.* 7:1505-10; Breisto et al., 1999, *Cancer Res.* 59:2944-49), and CA46 (Kreitman et al., 1999, *Int. J. Cancer* 81:148-55). Non-limiting example of a CD70-expressing Hodgkin's lymphoma line is L428 (Drexler, 1993, *Leuk. Lymphoma* 9:1-25; Dewan et al., 2005, *Cancer Sci.* 96:466-473). Non-limiting examples of CD70 expressing human renal cell carcinoma cell lines include 786-O (Ananth et al., 1999, *Cancer Res.* 59:2210-16; Datta et al., 2001, *Cancer Res.* 61:1768-75), ACHN (Hara et al., 2001, *J. Urol.* 166:2491-94; Miyake et al., 2002, *J. Urol.* 167:2203-08), Caki-1 (Prewett et al., 1998, *Clin. Cancer Res.* 4:2957-66; Shi and Siemann, 2002, *Br. J. Cancer* 87:119-26), and Caki-2 (Zellweger et al., 2001, *Neoplasia* 3:360-67). Non-limiting examples of CD70-expressing nasopharyngeal carcinoma cell lines include C15 and C17 (Busson et al., 1988, *Int. J. Cancer* 42:599-606; Bernheim et al., 1993, *Cancer Genet. Cytogenes.* 66:11-5). Non-limiting examples of CD70-expressing human glioma cell lines include U373 (Palma et al., 2000, *Br. J. Cancer* 82:480-7) and U87MG (Johns et al., 2002, *Int. J. Cancer* 98:398-408). Non-limiting examples of multiple myeloma cell lines include MM.1S (Greenstein et al., 2003, *Experimental Hematology* 31:271-282) and L363 (Diehl et al., 1978, *Blut* 36:331-338). (See also Drexler and Matsuo, 2000, *Leukemia Research* 24:681-703). These tumor cell lines can be established in immunodeficient rodent hosts either as solid tumor by subcutaneous injections or as disseminated tumors by intravenous injections. Once established within a host, these tumor models can be applied to evaluate the therapeutic efficacies of the anti-CD70 antibody or derivatives as described herein on modulating in vivo tumor growth.

VII. CD70-ASSOCIATED DISORDERS

The anti-CD70 binding agents (e.g., antibodies and derivatives) as described herein are useful for treating or preventing a CD70-expressing cancer or an immunological disorder characterized by expression of CD70 by inappropriate activation of immune cells (e.g., lymphocytes or dendritic cells). Such expression of CD70 can be due to, for example, increased CD70 protein levels on the cells surface and/or altered antigenicity of the expressed CD70. Treatment or prevention of the immunological disorder, according to the methods described herein, is achieved by administering to a subject in need of such treatment or prevention an effective amount of the anti-CD70 antibody or derivative, whereby the antibody or derivative (i) binds to activated immune cells that express CD70 and that are associated with the disease state and (ii) exerts a cytotoxic, cytostatic, or immunomodulatory effect on the activated immune cells. In some embodiments, the cytotoxic, cytostatic, or immunomodulatory is exerted without conjugation to a cytotoxic, cytostatic, or immunomodulatory agent. In some embodiments, the cytotoxic, cytostatic, or immunomodulatory is exerted by conjugation to a cytotoxic, cytostatic, or immunomodulatory agent.

Immunological diseases that are characterized by inappropriate activation of immune cells and that can be treated or prevented by the methods described herein can be classified, for example, by the type(s) of hypersensitivity reaction(s) that underlie the disorder. These reactions are typically classified into four types: anaphylactic reactions, cytotoxic (cytolytic) reactions, immune complex reactions, or cell-mediated immunity (CMI) reactions (also referred to as delayed-type hypersensitivity (DTH) reactions). (See, e.g., *Fundamental Immunology* (William E. Paul ed., Raven Press, N.Y., 3rd ed. 1993).)

Specific examples of such immunological diseases include the following: rheumatoid arthritis, psoriatic arthritis, autoimmune demyelinative diseases (e.g., multiple sclerosis, allergic encephalomyelitis), endocrine ophthalmopathy, uveoretinitis, systemic lupus erythematosus, myasthenia gravis, Grave's disease, glomerulonephritis, autoimmune hepatological disorder, inflammatory bowel disease (e.g., Crohn's disease), anaphylaxis, allergic reaction, Sjogren's syndrome, type I diabetes mellitus, primary biliary cirrhosis, Wegener's granulomatosis, fibromyalgia, polymyositis, dermatomyositis, multiple endocrine failure, Schmidt's syndrome, autoimmune uveitis, Addison's disease, adrenalitis, thyroiditis, Hashimoto's thyroiditis, autoimmune thyroid disease, pernicious anemia, gastric atrophy, chronic hepatitis, lupoid hepatitis, atherosclerosis, subacute cutaneous lupus erythematosus, hypoparathyroidism, Dressler's syndrome, autoimmune thrombocytopenia, idiopathic thrombocytopenic purpura, hemolytic anemia, pemphigus vulgaris, pemphigus, dermatitis herpetiformis, alopecia arcata, pemphigoid, scleroderma, progressive systemic sclerosis, CREST syndrome (calcinosis, Raynaud's phenomenon, esophageal dysmotility, sclerodactyl), and telangiectasia), male and female autoimmune infertility, ankylosing spondolytis, ulcerative colitis, mixed connective tissue disease, polyarteritis nedosa, systemic necrotizing vasculitis, atopic dermatitis, atopic rhinitis, Goodpasture's syndrome, Chagas' disease, sarcoidosis, rheumatic fever, asthma, recurrent abortion, anti-phospholipid syndrome, farmer's lung, erythema multiforme, post cardiotomy syndrome, Cushing's syndrome, autoimmune chronic active hepatitis, bird-fancier's lung, toxic epidermal necrolysis, Alport's syndrome, alveolitis, allergic alveolitis, fibrosing alveolitis, interstitial lung disease, erythema nodosum, pyoderma gangrenosum, transfusion reaction, Takayasu's arteritis, polymyalgia rheumatica, temporal arteritis, schistosomiasis, giant cell arteritis, ascariasis, aspergillosis, Sampter's syndrome, eczema, lymphomatoid granulomatosis, Behcet's disease, Caplan's syndrome, Kawasaki's disease, dengue, encephalomyelitis, endocarditis, endomyocardial fibrosis, endophthalmitis, erythema elevatum et diutinum, psoriasis, erythroblastosis fetalis, eosinophilic faciitis, Shulman's syndrome, Felty's syndrome, filariasis, cyclitis, chronic cyclitis, heterochronic cyclitis, Fuch's cyclitis, IgA nephropathy, Henoch-Schonlein purpura, graft versus host disease, transplantation rejection, cardiomyopathy, Eaton-Lambert syndrome, relapsing polychondritis, cryoglobulinemia, Waldenstrom's macroglobulemia, Evan's syndrome, and autoimmune gonadal failure.

Accordingly, the methods described herein encompass treatment of disorders of B lymphocytes (e.g., systemic lupus erythematosus, Goodpasture's syndrome, rheumatoid arthritis, and type I diabetes), $Th_1$-lymphocytes (e.g., rheumatoid arthritis, multiple sclerosis, psoriasis, Sjorgren's syndrome, Hashimoto's thyroiditis, Grave's disease, primary biliary cirrhosis, Wegener's granulomatosis, tuberculosis, or graft versus host disease), or $Th_2$-lymphocytes (e.g., atopic dermatitis, systemic lupus erythematosus, atopic asthma, rhinoconjunctivitis, allergic rhinitis, Omenn's syndrome, systemic sclerosis, or chronic graft versus host disease). Generally, disorders involving dendritic cells involve disorders of $Th_1$-lymphocytes or $Th_2$-lymphocytes.

In some embodiments, the immunological disorder is a T cell-mediated immunological disorder, such as a T cell disorder in which activated T cells associated with the disorder express CD70. Anti-CD70 binding agents (e.g., antibodies or derivatives) can be administered to deplete such CD70-expressing activated T cells. In a specific embodiment, administration of anti-CD70 antibodies or derivatives can deplete CD70-expressing activated T cells, while resting T cells are not substantially depleted by the anti-CD70 or derivative. In this context, "not substantially depleted" means that less than about 60%, or less than about 70% or less than about 80% of resting T cells are not depleted.

The anti-CD70 binding agents (e.g., antibodies and derivatives) are also useful for treating or preventing a CD70-expressing cancer. Treatment or prevention of a CD70-expressing cancer, according to the methods described herein, is achieved by administering to a subject in need of such treatment or prevention an effective amount of the anti-CD70 antibody or derivative, whereby the antibody or derivative (i) binds to CD70-expressing cancer cells and (ii) exerts a cytotoxic or cytostatic effect to deplete or inhibit the proliferation of the CD70-expressing cancer cells. In some embodiments, the cytotoxic, cytostatic, or immunomodulatory is exerted without conjugation to a cytotoxic, cytostatic, or immunomodulatory agent. In some embodiments, the cytotoxic, cytostatic, or immunomodulatory is exerted by conjugation to a cytotoxic, cytostatic, or immunomodulatory agent.

CD70-expressing cancers that can be treated or prevented by the methods described herein include, for example, different subtypes of Non-Hodgkin's Lymphoma (indolent NHLs, follicular NHLs, small lymphocytic lymphomas, lymphoplasmacytic NHLs, or marginal zone NHLs); Hodgkin's disease (e.g., Reed-Sternberg cells); cancers of the B-cell lineage, including, e.g., diffuse large B-cell lymphomas, follicular lymphomas, Burkitt's lymphoma, mantle cell lymphomas, B-cell lymphocytic leukemias (e.g., acute lymphocytic leukemia, chronic lymphocytic leukemia); Epstein Barr Virus positive B cell lymphomas; renal cell carcinomas (e.g., clear cell and papillary); nasopharyngeal carcinomas; thymic carcinomas; gliomas; glioblastomas; neuroblastomas; astrocytomas; meningiomas; Waldenstrom macroglobulinemia; multiple myelomas; and colon, stomach, and rectal carcinomas. The cancer can be, for example, newly diagnosed, pre-treated or refractory or relapsed. In some embodiments, a CD70-expressing cancer has at least about 15,000, at least about 10,000 or at least about 5,000 CD70 molecules/cell.

VIII. PHARMACEUTICAL COMPOSITIONS COMPRISING ANTI-CD70 ANTIBODIES AND DERIVATIVES AND ADMINISTRATION THEREOF

A composition comprising a CD70 binding agent (e.g., an anti-CD70 antibody or derivative) can be administered to a subject having or at risk of having an immunological disorder or a CD70-expressing cancer. The invention further provides for the use of a CD70 binding agent (e.g., an anti-CD70 antibody or derivative) in the manufacture of a medicament for prevention or treatment of a CD70 expressing cancer or immunological disorder. The term "subject" as used herein means any mammalian patient to which a CD70-binding agent can be administered, including, e.g., humans and non-human mammals, such as primates, rodents, and dogs. Subjects specifically intended for treatment using the methods described herein include humans. The antibodies or derivatives can be administered either alone or in combination with other compositions in the prevention or treatment of the immunological disorder or CD70-expressing cancer.

Various delivery systems are known and can be used to administer the CD70 binding agent. Methods of introduction include but are not limited to intradermal, intramuscular, intraperitoneal, intravenous, subcutaneous, intranasal, epidural, and oral routes. The CD70 binding agent can be administered, for example by infusion or bolus injection (e.g., intravenous or subcutaneous), by absorption through epithelial or mucocutaneous linings (e.g., oral mucosa, rectal and intestinal mucosa, and the like) and can be administered together with other biologically active agents such as chemotherapeutic agents. Administration can be systemic or local.

In specific embodiments, the CD70 binding agent composition is administered by injection, by means of a catheter, by means of a suppository, or by means of an implant, the implant being of a porous, non-porous, or gelatinous material, including a membrane, such as a sialastic membrane, or a fiber. Typically, when administering the composition, materials to which the anti-CD70 binding agent does not absorb are used.

In other embodiments, the anti-CD70 binding agent is delivered in a controlled release system. In one embodiment, a pump may be used (see Langer, 1990, *Science* 249:1527-1533; Sefton, 1989, *CRC Crit. Ref. Biomed. Eng.* 14:201; Buchwald et al., 1980, *Surgery* 88:507; Saudek et al., 1989, *N. Engl. J. Med.* 321:574). In another embodiment, polymeric materials can be used. (See *Medical Applications of Controlled Release* (Langer and Wise eds., CRC Press, Boca Raton, Fla., 1974); *Controlled Drug Bioavailability, Drug Product Design and Performance* (Smolen and Ball eds., Wiley, New York, 1984); Ranger and Peppas, 1983, *Macromol. Sci. Rev. Macromol. Chem.* 23:61. See also Levy et al., 1985, *Science* 228:190; During et al., 1989, *Ann. Neurol.* 25:351; Howard et al., 1989, *J. Neurosurg.* 71:105.) Other controlled release systems are discussed, for example, in Langer, supra.

A CD70 binding agent (e.g., an anti-CD70 antibody or derivative) can be administered as pharmaceutical compositions comprising a therapeutically effective amount of the binding agent and one or more pharmaceutically compatible ingredients. For example, the pharmaceutical composition typically includes one or more pharmaceutical carriers (e.g., sterile liquids, such as water and oils, including those of petroleum, animal, vegetable or synthetic origin, such as peanut oil, soybean oil, mineral oil, sesame oil and the like). Water is a more typical carrier when the pharmaceutical composition is administered intravenously. Saline solutions and aqueous dextrose and glycerol solutions can also be employed as liquid carriers, particularly for injectable solutions. Suitable pharmaceutical excipients include, for example, starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulations can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the protein, typically in purified form, together with a suitable amount of carrier so as to provide the form for proper administration to the patient. The formulations correspond to the mode of administration.

In typical embodiments, the pharmaceutical composition is formulated in accordance with routine procedures as a pharmaceutical composition adapted for intravenous administration to human beings. Typically, compositions for intravenous administration are solutions in sterile isotonic aqueous buffer. Where necessary, the pharmaceutical can also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the pharmaceutical is to be administered by infusion, it can be dispensed with an infusion bottle containing sterile pharmaceutical grade water or saline. Where the pharmaceutical is administered by injection, an ampoule of sterile water for injection or saline can be provided so that the ingredients can be mixed prior to administration.

Further, the pharmaceutical composition can be provided as a pharmaceutical kit comprising (a) a container containing a CD70 binding agent (e.g., an anti-CD70 antibody or derivative) in lyophilized form and (b) a second container containing a pharmaceutically acceptable diluent (e.g., sterile water) for injection. The pharmaceutically acceptable diluent can be used for reconstitution or dilution of the lyophilized anti-CD70 antibody or derivative. Optionally associated with such container(s) can be a notice in the form prescribed by a governmental agency regulating the manufacture, use or sale of pharmaceuticals or biological products, which notice reflects approval by the agency of manufacture, use or sale for human administration.

The amount of the CD70 binding agent (e.g., anti-CD70 antibody or derivative) that is effective in the treatment or prevention of an immunological disorder or CD70-expressing cancer can be determined by standard clinical techniques. In addition, in vitro assays may optionally be employed to help identify optimal dosage ranges. The precise dose to be employed in the formulation will also depend on the route of administration, and the stage of immunological disorder or CD70-expressing cancer, and should be decided according to the judgment of the practitioner and each patient's circumstances. Effective doses may be extrapolated from dose-response curves derived from in vitro or animal model test systems.

For example, toxicity and therapeutic efficacy of the anti-CD70 antibody or derivative can be determined in cell cultures or experimental animals by standard pharmaceutical procedures for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. A CD70-binding agent (e.g., an anti-CD70 antibody or derivative) that exhibits a large therapeutic index is preferred. Where a CD70-binding agent exhibits toxic side effects, a delivery system that targets the CD70-binding agent to the site of affected tissue can be used to minimize potential damage non-CD70-expressing cells and, thereby, reduce side effects.

The data obtained from the cell culture assays and animal studies can be used in formulating a range of dosage for use in humans. The dosage of the CD70 binding agent typically lies within a range of circulating concentrations that include the $ED_{50}$ with little or no toxicity. The dosage may vary within this range depending upon the dosage form employed and the route of administration utilized. For a CD70 binding agent used in the method, the therapeutically effective dose can be estimated initially from cell culture assays. A dose can be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma can be measured, for example, by high performance liquid chromatography.

Generally, the dosage of an anti-CD70 antibody or derivative administered to a patient with an immunological disorder or CD70-expressing cancer is about 0.1 mg/kg to 100 mg/kg of the subject's body weight. More typically, the dosage administered to a subject is 0.1 mg/kg to 50 mg/kg of the subject's body weight, even more typically 1 mg/kg to 30 mg/kg, 1 mg/kg to 20 mg/kg, 1 mg/kg to 15 mg/kg, 1 mg/kg to 12 mg/kg, 1 mg/kg to 10 mg/kg, or 1 mg/kg to 7.5 mg/kg of the subject's body weight. Generally, human antibodies have a longer half-life within the human body than antibodies from other species due to the immune response to the foreign proteins. Thus, lower dosages of anti-CD70 antibody or derivative comprising humanized or chimeric antibodies and less frequent administration is often possible.

A dose of an anti-CD70 binding agent can be administered, for example, daily, once per week (weekly), twice per week, thrice per week, four times per week, five times per week, biweekly, monthly or otherwise as needed.

In some embodiments, the dosage of an anti-CD70 binding agent corresponds to a sub-optimal dosage (i.e., below the $EC_{50}$ for the anti-CD70 binding agent (e.g., an antibody drug conjugate). For example, the dosage of an anti-CD70 binding agent can comprise a dosage selected from the lowest 25%, lowest 15%, lowest 10% or lowest 5% of the therapeutic window. As used herein, the term "therapeutic window" refers to the range of dosage of a drug or of its concentration in a bodily system that provides safe and effective therapy.

In some embodiments, the dosage of an anti-CD70 binding agent (e.g., an antibody drug conjugate) is from about 0.05 mg/kg to about 1 mg/kg, or about 0.1 mg/kg to about 0.9 mg/kg, or about 0.15 to about 0.75 mg/kg of the subject's body weight. Such a dosage can be administered from 1 to about 15 times per week. Each dose can be the same or different. For example, a dosage of about 0.15 mg/kg of an anti-CD70 binding agent can be administered from 1 to 10 times per four day, five day, six day or seven day period.

In some embodiments, the pharmaceutical compositions comprising the CD70 binding agent can further comprise a therapeutic agent (e.g., a non-conjugated cytotoxic or immunomodulatory agent such as, for example, any of those described herein). The anti-CD70 binding agent also can be co-administered in combination with one or more therapeutic agents for the treatment or prevention of immunological disorders or CD70-expressing cancers. For example, combination therapy can include a therapeutic agent (e.g., a cytostatic, cytotoxic, or immunomodulatory agent, such as an unconjugated cytostatic, cytotoxic, or immunomodulatory agent such as those conventionally used for the treatment of cancers or immunological disorders). Combination therapy can also include, e.g., administration of an agent that targets a receptor or receptor complex other than CD70 on the surface of activated lymphocytes, dendritic cells or CD70-expressing cancer cells. An example of such an agent includes a second, non-CD70 antibody that binds to a molecule at the surface of an activated lymphocyte, dendritic cell or CD70-expressing cancer cell. Another example includes a ligand that targets such a receptor or receptor complex. Typically, such an antibody or ligand binds to a cell surface receptor on activated lymphocytes, dendritic cell or CD70-expressing cancer cell and enhances the cytotoxic or cytostatic effect of the anti-CD70 antibody by delivering a cytostatic or cytotoxic signal to the activated lymphocyte, dendritic cell or CD70-expressing cancer cell. Such combinatorial administration can have an additive or synergistic effect on disease parameters (e.g., severity of a symptom, the number of symptoms, or frequency of relapse).

With respect to therapeutic regimens for combinatorial administration, in a specific embodiment, an anti-CD70 binding agent is administered concurrently with a therapeutic agent. In another specific embodiment, the therapeutic agent is administered prior or subsequent to administration of the anti-CD70 antibody or derivative, by at least an hour and up to several months, for example at least an hour, five hours, 12 hours, a day, a week, a month, or three months, prior or subsequent to administration of the anti-CD70 antibody or derivative. In some embodiments, the subject is monitored following administration of the anti-CD70 binding agent, and optionally the therapeutic agent.

The therapeutic agent can be, for example, any agent that exerts a therapeutic effect on cancer cells or activated immune cells. Typically, the therapeutic agent is a cytotoxic or immunomodulatory agent. Such combinatorial administration can have an additive or synergistic effect on disease parameters (e.g., severity of a symptom, the number of symptoms, or frequency of relapse).

Useful classes of cytotoxic or immunomodulatory agents include, for example, antitubulin agents, auristatins, DNA minor groove binders, DNA replication inhibitors, alkylating agents (e.g., platinum complexes such as cis-platin, mono(platinum), bis(platinum) and tri-nuclear platinum complexes and carboplatin), anthracyclines, antibiotics, antifolates, antimetabolites, chemotherapy sensitizers, duocarmycins, etoposides, fluorinated pyrimidines, ionophores, lexitropsins, nitrosoureas, platinols, pre-forming compounds, purine antimetabolites, puromycins, radiation sensitizers, steroids, taxanes, topoisomerase inhibitors, vinca alkaloids, and the like.

Individual cytotoxic or immunomodulatory agents include, for example, an androgen, anthramycin (AMC), asparaginase, 5-azacytidine, azathioprine, bleomycin, busulfan, buthionine sulfoximine, camptothecin, carboplatin, carmustine (BSNU), CC-1065, chlorambucil, cisplatin, colchicine, cyclophosphamide, cytarabine, cytidine arabinoside, cytochalasin B, dacarbazine, dactinomycin (actinomycin), daunorubicin, decarbazine, docetaxel, doxorubicin, an estrogen, 5-fluorodeoxyuridine, 5-fluorouracil, gramicidin D, hydroxyurea, idarubicin, ifosfamide, irinotecan, lomustine (CCNU), mechlorethamine, melphalan, 6-mercaptopurine, methotrexate, mithramycin, mitomycin C, mitoxantrone, nitroimidazole, paclitaxel, plicamycin, procarbizine, rapamycin (Sirolimus), streptozotocin, tenoposide, 6-thioguanine, thioTEPA, topotecan, vinblastine, vincristine, vinorelbine, VP-16 and VM-26.

In some typical embodiments, the therapeutic agent is a cytotoxic agent. Suitable cytotoxic agents include, for example, dolastatins (e.g., auristatin E, AFP, MMAF, MMAE), DNA minor groove binders (e.g., enediynes and lexitropsins), duocarmycins, taxanes (e.g., paclitaxel and docetaxel), puromycins, vinca alkaloids, CC-1065, SN-38, topotecan, morpholino-doxorubicin, rhizoxin, cyanomorpholino-doxorubicin, echinomycin, combretastatin, netropsin, epothilone A and B, estramustine, cryptophysins, cemadotin, maytansinoids, discodermolide, eleutherobin, and mitoxantrone.

In some embodiments, the cytotoxic agent is a conventional chemotherapeutic such as, for example, doxorubicin, paclitaxel, melphalan, vinca alkaloids, methotrexate, mitomycin C or etoposide. In some embodiments, the therapeutic agent can be a combined therapy, such as CHOP (Cyclophosphamide, Doxorubicin, Prednisolone and Vincristine), CHOP-R (Cyclophosphamide, Doxorubicin Vincristine, Prednisolone, and rituximab) or ABVD (Doxorubicin, Bleomycin, Vinblastine and Dacarbazine). Agents such as CC-1065 analogues, calicheamicin, maytansine, analogues of dolastatin 10, rhizoxin, and palytoxin can be linked to the anti-CD70 antibodies or derivatives thereof.

In specific embodiments, the cytotoxic or cytostatic agent is auristatin E (also known in the art as dolastatin-10) or a derivative thereof. Typically, the auristatin E derivative is, e.g., an ester formed between auristatin E and a keto acid. For example, auristatin E can be reacted with paraacetyl benzoic acid or benzoylvaleric acid to produce AEB and AEVB, respectively. Other typical auristatin derivatives include AFP, MMAF, and MMAE. The synthesis and structure of auristatin E and its derivatives are described in U.S. Patent Application Publication Nos. 20030083263 and 20050009751), International Patent Application No. PCT/US03/24209, International Patent Application No. PCT/US02/13435, and U.S. Pat. Nos. 6,323,315; 6,239,104; 6,034,065; 5,780,588; 5,665,860; 5,663,149; 5,635,483; 5,599,902; 5,554,725; 5,530,097; 5,521,284; 5,504,191; 5,410,024; 5,138,036; 5,076,973; 4,986,988; 4,978,744; 4,879,278; 4,816,444; and 4,486,414.

In specific embodiments, the cytotoxic agent is a DNA minor groove binding agent. (See, e.g., U.S. Pat. No. 6,130, 237.) For example, in some embodiments, the minor groove binding agent is a CBI compound. In other embodiments, the minor groove binding agent is an enediyne (e.g., calicheamicin).

Examples of anti-tubulin agents include, but are not limited to, taxanes (e.g., Taxol® (paclitaxel), Taxotere® (docetaxel)), T67 (Tularik), vinca alkyloids (e.g., vincristine, vinblastine, vindesine, and vinorelbine), and dolastatins (e.g., auristatin E, AFP, MMAF, MMAE, AEB, AEVB). Other antitubulin agents include, for example, baccatin derivatives, taxane analogs (e.g., epothilone A and B), nocodazole, colchicine and colcimid, estramustine, cryptophysins, cemadotin, maytansinoids, combretastatins, discodermolide, and eleutherobin.

In some embodiments, the cytotoxic agent is a maytansinoid, another group of anti-tubulin agents. For example, in specific embodiments, the maytansinoid is maytansine or DM-1 (ImmunoGen, Inc.; see also Chari et al., 1992, *Cancer Res.* 52:127-131).

In some embodiments, the therapeutic agent is not a radioisotope. In some embodiments, the therapeutic agent is not ricin or saporin.

In certain embodiments, the therapeutic agent is an anti-VEGF agent, such as AVASTIN (bevacizumab) or NEXAVAR (Sorafenib); a PDGF blocker, such as SUTENT (sunitinib malate); or a kinase inhibitor, such as NEXAVAR (sorafenib tosylateor).

In some embodiments, the cytotoxic or immunomodulatory agent is an antimetabolite. The antimetabolite can be, for example, a purine antagonist (e.g., azothioprine or mycophenolate mofetil), a dihydrofolate reductase inhibitor (e.g., methotrexate), acyclovir, gangcyclovir, zidovudine, vidarabine, ribavarin, azidothymidine, cytidine arabinoside, amantadine, dideoxyuridine, iododeoxyuridine, poscarnet, or trifluridine.

In other embodiments, the cytotoxic or immunomodulatory agent is tacrolimus, cyclosporine or rapamycin. In further embodiments, the cytoxic agent is aldesleukin, alemtuzumab, alitretinoin, allopurinol, altretamine, amifostine, anastrozole, arsenic trioxide, bexarotene, bexarotene, calusterone, capecitabine, celecoxib, cladribine, Darbepoetin alfa, Denileukin diftitox, dexrazoxane, dromostanolone propionate, epirubicin, Epoetin alfa, estramustine, exemestane, Filgrastim, floxuridine, fludarabine, fulvestrant, gemcitabine, gemtuzumab ozogamicin, goserelin, idarubicin, ifosfamide, imatinib mesylate, Interferon alfa-2a, irinotecan, letrozole, leucovorin, levamisole, meclorethamine or nitrogen mustard, megestrol, mesna, methotrexate, methoxsalen, mitomycin C, mitotane, nandrolone phenpropionate, oprelvekin, oxaliplatin, pamidronate, pegademase, pegaspargase, pegfilgrastim, pentostatin, pipobroman, plicamycin, porfimer sodium, procarbazine, quinacrine, rasburicase, Sargramostim, streptozocin, tamoxifen, temozolomide, teniposide, testolactone, thioguanine, toremifene, Tositumomab, Trastuzumab, tretinoin, uracil mustard, vairubicin, vinblastine, vincristine, vinorelbine or zoledronate.

In additional embodiments, the therapeutic agent is an antibody, such as a humanized anti HER2 monoclonal antibody, RITUXAN (rituximab; Genentech; a chimeric anti CD20 monoclonal antibody); OVAREX (AltaRex Corporation, MA); PANOREX (Glaxo Wellcome, NC; a murine IgG2a antibody); Cetuximab Erbitux (Imclone Systems Inc., NY; an anti-EGFR IgG chimeric antibody); Vitaxin (Med-Immune, Inc., MD; Campath I/H (Leukosite, MA; a humanized IgG1 antibody); Smart MI95 (Protein Design Labs, Inc., CA; a humanized anti-CD33 IgG antibody); LymphoCide (Immunomedics, Inc., NJ; a humanized anti-CD22

IgG antibody); Smart ID10 (Protein Design Labs, Inc., CA; a humanized anti-HLA-DR antibody); Oncolym (Techniclone, Inc., CA; a radiolabeled murine anti-HLA-Dr10 antibody); Allomune (BioTransplant, CA; a humanized anti-CD2 mAb); Avastin (Genentech, Inc., CA; an anti-VEGF humanized antibody); Epratuzamab (Immunomedics, Inc., NJ and Amgen, CA; an anti-CD22 antibody); CEAcide (Immunomedics, NJ; a humanized anti-CEA antibody); or an anti-CD40 antibody (e.g., as disclosed in U.S. Pat. No. 6,838,261).

Other suitable antibodies include, but are not limited to, antibodies against the following antigens: CA125, CA15-3, CA19-9, L6, Lewis Y, Lewis X, alpha fetoprotein, CA 242, placental alkaline phosphatase, prostate specific membrane antigen, prostatic acid phosphatase, epidermal growth factor, MAGE-1, MAGE-2, MAGE-3, MAGE-4, anti-transferrin receptor, p97, MUC1-KLH, CEA, gp100, MART1, Prostate Specific Antigen, IL-2 receptor, CD20, CD52, CD30, CD33, CD22, human chorionic gonadotropin, CD38, CD40, mucin, P21, MPG, and Neu oncogene product.

In some embodiments, the therapeutic agent is an immunomodulatory agent. The immunomodulatory agent can be, for example, gancyclovir, etanercept, tacrolimus, cyclosporine, rapamycin, REVLIMID (lenalidomide), cyclophosphamide, azathioprine, mycophenolate mofetil or methotrexate. Alternatively, the immunomodulatory agent can be, for example, a glucocorticoid (e.g., cortisol or aldosterone) or a glucocorticoid analogue (e.g., prednisone or dexamethasone).

In some typical embodiments, the immunomodulatory agent is an anti-inflammatory agent, such as arylcarboxylic derivatives, pyrazole-containing derivatives, oxicam derivatives and nicotinic acid derivatives. Classes of anti-inflammatory agents include, for example, cyclooxygenase inhibitors, 5-lipoxygenase inhibitors, and leukotriene receptor antagonists. In some embodiments, the immodulatory agent is a cytokine, such as G-CSF, GM-CSF or IL-2.

Suitable cyclooxygenase inhibitors include meclofenamic acid, mefenamic acid, carprofen, diclofenac, diflunisal, fenbufen, fenoprofen, ibuprofen, indomethacin, ketoprofen, nabumetone, naproxen, sulindac, tenoxicam, tolmetin, and acetylsalicylic acid.

Suitable lipoxygenase inhibitors include redox inhibitors (e.g., catechol butane derivatives, nordihydroguaiaretic acid (NDGA), masoprocol, phenidone, Ianopalen, indazolinones, naphazatrom, benzofuranol, alkylhydroxylamine), and non-redox inhibitors (e.g., hydroxythiazoles, methoxyalkylthiazoles, benzopyrans and derivatives thereof, methoxytetrahydropyran, boswellic acids and acetylated derivatives of boswellic acids, and quinolinemethoxyphenylacetic acids substituted with cycloalkyl radicals), and precursors of redox inhibitors.

Other suitable lipoxygenase inhibitors include antioxidants (e.g., phenols, propyl gallate, flavonoids and/or naturally occurring substrates containing flavonoids, hydroxylated derivatives of the flavones, flavonol, dihydroquercetin, luteolin, galangin, orobol, derivatives of chalcone, 4,2',4'-trihydroxychalcone, ortho-aminophenols, N-hydroxyureas, benzofuranols, ebselen and species that increase the activity of the reducing selenoenzymes), iron chelating agents (e.g., hydroxamic acids and derivatives thereof, N-hydroxyureas, 2-benzyl-1-naphthol, catechols, hydroxylamines, carnosol trolox C, catechol, naphthol, sulfasalazine, zyleuton, 5-hydroxyanthranilic acid and 4-(omega-arylalkyl)phenylalkanoic acids), imidazole-containing compounds (e.g., ketoconazole and itraconazole), phenothiazines, and benzopyran derivatives.

Yet other suitable lipoxygenase inhibitors include inhibitors of eicosanoids (e.g., octadecatetraenoic, eicosatetraenoic, docosapentaenoic, eicosahexaenoic and docosahexaenoic acids and esters thereof, PGE1 (prostaglandin E1), PGA2 (prostaglandin A2), viprostol, 15-monohydroxyeicosatetraenoic, 15-monohydroxy-eicosatrienoic and 15-monohydroxyeicosapentaenoic acids, and leukotrienes B5, C5 and D5), compounds interfering with calcium flows, phenothiazines, diphenylbutylamines, verapamil, fuscoside, curcumin, chlorogenic acid, caffeic acid, 5,8,11,14-eicosatetrayenoic acid (ETYA), hydroxyphenylretinamide, Ionapalen, esculin, diethylcarbamazine, phenantroline, baicalein, proxicromil, thioethers, diallyl sulfide and di-(1-propenyl)sulfide.

Leukotriene receptor antagonists include calcitriol, ontazolast, Bayer Bay-x-1005, Ciba-Geigy CGS-25019C, ebselen, Leo Denmark ETH-615, Lilly LY-293111, Ono ONO-4057, Terumo TMK-688, Boehringer Ingleheim BI-RM-270, Lilly LY 213024, Lilly LY 264086, Lilly LY 292728, Ono ONO LB457, Pfizer 105696, Perdue Frederick PF 10042, Rhone-Poulenc Rorer RP 66153, SmithKline Beecham SB-201146, SmithKline Beecham SB-201993, SmithKline Beecham SB-209247, Searle SC-53228, Sumitamo SM 15178, American Home Products Way 121006, Bayer Bay-o-8276, Warner-Lambert CI-987, Warner-Lambert CI-987BPC-15LY 223982, Lilly LY 233569, Lilly LY-255283, MacroNex MNX-160, Merck and Co. MK-591, Merck and Co. MK-886, Ono ONO-LB-448, Purdue Frederick PF-5901, Rhone-Poulenc Rorer RG 14893, Rhone-Poulenc Rorer RP 66364, Rhone-Poulenc Rorer RP 69698, Shionoogi S-2474, Searle SC-41930, Searle SC-50505, Searle SC-51146, Searle SC-52798, SmithKline Beecham SKand F-104493, Leo Denmark SR-2566, Tanabe T-757 and Teijin TEI-1338.

The invention is further described in the following examples, which are in not intended to limit the scope of the invention. Cell lines described in the following examples were maintained in culture according to the conditions specified by the American Type Culture Collection (ATCC) or Deutsche Sammlung von Mikroorganismen und Zellkulturen GmbH, Braunschweig, Germany (DMSZ), or as otherwise known. Cell culture reagents were obtained from Invitrogen Corp., Carlsbad, Calif.

Example 1

Production of Humanized Anti-CD70 Antibody Variants

The nucleotide and amino acid sequences of the heavy and light variable regions of antiCD70 murine monoclonal antibody, 1F6, and a chimeric variant of 1F6, c1F6, are set forth as SEQ ID NOS:1, 2, 21 and 22, respectively. (See also U.S. Patent Application No. 60/645,355, filed Jan. 19, 2005). Human acceptor sequences for humanization of c1F6 were chosen from human germline exon $V_H$, $J_H$, Vκ and Jκ sequences. Acceptor sequences for c1F6 $V_H$ domain humanization were chosen from germline $V_H$ exons $V_H$1-18 (Matsuda et al., 1993, *Nature Genetics* 3:88-94) or $V_H$1-2 (Shin et al., 1991, *EMBO J.* 10:3641-3645) and $J_H$ exon $J_H$-6 (Mattila et al., 1995, *Eur. J. Immunol.* 25:2578-2582). Germline Vκ exon B3 (Cox et al., 1994, *Eur. J. Immunol.* 24:827-836) and Jκ exon Jκ-1 (Hieter et al., 1982, *J. Biol. Chem.* 257:1516-1522) were chosen as acceptor sequences for c1F6 $V_L$ domain humanization. 1F6 murine CDRs, determined according to the Kabat definition, were grafted onto the chosen human germline template. Briefly, synthetic overlapping oligonucleotides spanning the humanized $V_H$ or $V_L$ domain were generated and PCR overlap extension was used to assemble each domain. Restriction sites incorporated into the PCR product were used to directionally clone the $V_H$ and $V_L$ domain into a pCMV expression vector in frame with human IgG1 constant domains or Kappa constant domain, respectively.

Several framework positions were chosen for reintroduction of mouse donor residues. These were positions H46, H67, H68, H69, H70, H71, H80, H81, H82, H82A and H91 in the $V_H$ domain, according to the Kabat numbering convention. No framework positions were altered in the $V_L$ domain, although mouse CDR1 residues at positions L25 and L33 were chosen for introduction of the human acceptor residue for that position.

Several variants of humanized 1F6 were generated by incorporating different combinations of mouse framework donor residues in the $V_H$ domain or human CDR residues in the $V_L$ domain. These variants are summarized in Tables 2 and 3 below.

TABLE 2

| $V_H$ variant | VH exon acceptor sequence | donor framework residues |
|---|---|---|
| h$V_H$ A | VH1-18 | H71, H91 |
| h$V_H$ B | VH1-18 | H71 |
| h$V_H$ C | VH1-18 | H91 |
| h$V_H$ D | VH1-18 | none |
| h$V_H$ E | VH1-2 | none |
| h$V_H$ F | VH1-18 | H67, H68, H69, H70, H71 |
| h$V_H$ G | VH1-18 | H80, H81, H82, H82A |
| h$V_H$ H | VH1-18 | H67, H68, H69, H70, H71, H80, H81, H82, H82A |
| h$V_H$ I | VH1-18 | H46, H71, H91 |
| h$V_H$ J | VH1-2 | H46 |
| h$V_H$ K | VH1-2 | H71 |
| h$V_H$ L | VH1-2 | H46, H71 |
| h$V_H$ M | VH1-18 | H46, H67, H68, H69, H70, H71 |
| h$V_H$ N | VH1-18 | H69, H70, H71, H80 |

TABLE 3

| $V_L$ variant | Acceptor CDR residue |
|---|---|
| h$V_L$ A | none |
| h$V_L$ B | L25 |
| h$V_L$ C | L33 |
| h$V_L$ D | L25, L33 |

The differences between some of the humanized variants with the murine and human $V_H$ sequences are illustrated in FIGS. 1 and 2. An alignment of humanized 1F6 $V_H$ variants h$V_H$E and h$V_H$J with 1F6 m$V_H$ and human germline $V_H$ exon $V_H$1-2 and $J_H$ exon JH6 is shown in FIG. 1. An alignment of humanized 1F6 $V_H$ variants h$V_H$H and h$V_H$M with 1F6 m$V_H$ and human germline $V_H$ exon VH1-18 and $J_H$ exon JH6 is shown in FIG. 2. An alignment of humanized 1F6 $V_L$ variant h$V_L$A with 1F6 m$V_L$ and human germline $V_K$ exon B3 and $J_K$ exon JK-1 is shown in FIG. 3.

Example 2

Binding Affinities of Humanized 1F6 Variants

Humanized 1F6 variants HDLA (h$V_H$D and h$V_L$A), HHLA (h$V_H$H and h$V_L$A), and HJLA (h$V_H$J and h$V_L$A), were selected for binding affinity analysis. One mg of each humanized antibody and c1F6 were transiently expressed in 293 cells and labeled with europium using the Eu-N1 iodoacetamido chelate (Perkin Elmer). Saturation binding to a panel of CD70 positive cell lines was assessed for each labeled antibody. The cell lines selected were ACHN, Caki-2, Caki-1, and 786-O with antigen copies/cell determined by quantitative flow cytometry (or fluorescence activated cell sorting, i.e., FACS) of 30,000, 99,000, 235,000, and 252,000 respectively.

Europium-labeled antibodies were incubated with cells for 1 hour at 4° C. over a range of concentrations in 96 well plates. Following incubation europium was released by resuspension of the cells in Enhancement Buffer (Perkin Elmer). Fluorescence was read in a Fusion HT plate reader using a top detector format and excitation of 335 nm and emission of 620 nm Data was fit to a one binding site hyperbola using GraphPad Prism 4. The results are shown below in Table 4.

TABLE 4

| Cell line | Antigen/cell | Apparent binding affinity $K_D$ (nM) | | | |
|---|---|---|---|---|---|
| | | c1F6 | h1F6 HDLA | h1F6 HHLA | h1F6 HJLA |
| ACHN | 30,000 | 0.30 | 1.44 | 0.29 | 0.68 |
| Caki-1 | 235,000 | 1.28 | 1.29 | 1.22 | 1.36 |
| Caki-2 | 99,000 | 0.26 | 0.86 | 0.15 | 0.37 |
| 786-O | 252,000 | 0.56 | 0.55 | 0.28 | 0.46 |

The $K_D$ values for the humanized variants are very similar to c1F6 on all of the cell lines tested, confirming that the humanization process did not significantly reduce antigen binding activity.

Example 3

ADCC Activity of Humanized 1F6

The ability of humanized 1F6 antibody variants to mediate ADCC against the CD70$^+$ cell lines WIL2-S, 786-O and 769-P was measured using a standard $^{51}$Cr release assay. The HHLA, HJLA and HELA variants of humanized 1F6 lysed WIL-2S target cells equivalently and in a dose dependent manner. In contrast, tumor cells treated with CD70-binding murine 1F6 (m1F6) or non-binding control human Ig (hIg) were not killed (FIG. 4A). Similarly, humanized 1F6 mediated the lysis of two renal cell carcinoma targets in a manner comparable to chimeric 1F6 (FIG. 4B).

Example 4

CDC Activity of Humanized 1F6

The ability of humanized 1F6 to mediate CDC was examined using a multiple myeloma cell line (LP-1) and two lymphoma cell lines (MHH PreB-1 and WIL2-S). Target cells were treated with graded doses of chimeric 1F6, humanized 1F6 HJLA or a non-binding human Ig control in the presence of normal human serum. After incubation at 37° C. for 2 hours, lysed cells were identified by flow cytometry after the addition of propidium iodide (5 µg/mL). Cells stained with propidium iodide were considered to have lost plasma membrane integrity as a result of antibody-mediated complement activation and formation of the membrane attack complex. Using this assay, chimeric 1F6 and humanized 1F6 mediated dose-dependent lysis of each target in an equivalent manner (FIG. 5).

Example 5

ADCP Activity of Humanized 1F6

The ability of humanized 1F6 to mediate phagocytosis was examined using the CD70+ renal cell carcinoma line 786-O pre-labeled with a red fluorescent membrane dye. Target cells were treated with graded doses of chimeric 1F6, humanized 1F6 HJLA or a non-binding human Ig control and were then mixed with macrophages generated from adherent peripheral blood monocytes cultured in GM-CSF. After incubation at 37° C. for 1 hour, the macrophages were detected with a green fluorescent antibody to the macrophage cell surface marker CD11b. Macrophages that had phagocytosed tumor cells were identified by dual red and green fluorescence as detected by flow cytometry. The presence of tumor cells within macrophages in the dual-positive population was confirmed by fluorescence microscopy. As shown in FIG. 6, chimeric and humanized 1F6 facilitated phagocytosis of target cells in an antibody-dose dependent fashion and to an equivalent degree. In contrast, target cells incubated with a non-binding control antibody were minimally engulfed by macrophages.

Example 6

In Vitro Cytotoxicity Activity of Humanized 1F6 Variant Drug Conjugates

Humanized 1F6 variants HELA ($hV_HE$ and $hV_LA$), HHLA, HJLA, and HMLA ($hV_HM$ and $hV_LA$), and c1F6 were transiently expressed in 293 cells and conjugated to vcMMAF (described in U.S. Ser. No. 10/983,340; published as U.S. Patent Publication No. 2005-0238649, Oct. 27, 2005) at a loading level of an average of eight drug units per antibody. The resulting conjugates, h1F6 HELA-F8, h1F6 HHLA-F8, h1F6 HJLA-F8, h1F6 HMLA-F8, and c1F6-F8 were tested for cytotoxicity against two CD70 expressing cell lines, 786-O and Caki-1. The conjugates were incubated with the cells for 92 hours, followed by addition of 50 µM resazurin. After a 4 hour incubation period, dye reduction was measured using a Fusion HT fluorescent plate reader (Packard Instruments, Meriden, Conn.). The results of triplicate sampling are shown below in Table 5. The $IC_{50}$ values of all four humanized variants are active within two-fold of c1F6 on both cell lines tested with a potency ranking of c1F6-F8>h1F6 HHLA-F8>h1F6 HMLA-F8>h1F6 HJLA-F8>h1F6 HELA-F8.

TABLE 5

| h1F6-vcMMAF | No. of mouse FR residues | Caki-1 IC50 [ng/ml] | 786-O IC50 [ng/ml] |
| --- | --- | --- | --- |
| h1F6 HELA-F8 | 0 | 3.4 (mean = 2.87, n = 3) | 5.2 (mean = 3.9, n = 3) |
| h1F6 HHLA-F8 | 9 | 1.4 (mean = 1.87, n = 3) | 2.3 (mean = 1.93, n = 3) |
| h1F6 HJLA-F8 | 1 | 2.2 (mean = 2.3, n = 3) | 3.4 (mean = 3.03, n = 3) |
| h1F6 HMLA-F8 | 6 | 1.8 (mean = 2.07, n = 3) | 2.8 (mean = 2.03, n = 3) |
| c1F6(293)-F8 | 0 | 1.8 (mean = 2.17, n = 3) | 2.4 (mean = 1.45, n = 3) |

Example 7

In Vivo Screening of Humanized 1F6 Drug Conjugates

Humanized 1F6 variants HDLA, HHLA, HJLA, and HELA, were transiently expressed in 293 cells and conjugated to mcMMAF (described in U.S. Ser. No. 10/983,340; published as U.S. Patent Publication No. 2005-0238649, Oct. 27, 2005) at a loading level of eight drug units per antibody. An efficacy study of a single dose at 3 mg/kg or 10 mg/kg was performed in a 786-O renal cell carcinoma solid tumor model in nude mice. Tumor volume was measured regularly for 80 days post-tumor implant. The results indicate that tumor volume was greatly reduced in all treated mice in comparison to untreated mice, and all humanized 1F6 variants conjugated to mcMMAF were comparable in efficacy to c1F6mcMMAF.

Example 8

In Vivo Activity of Humanized 1F6 in SCID Mouse Xenograft Models of Disseminated Lymphoma and Multiple Myeloma The in vivo antitumor activity of humanized 1F6 (HJLA) was examined in disseminated lymphoma and multiple myeloma xenograft mouse models. To establish disseminated disease, $1\times10^6$ Raji or $1\times10^7$ MM1.S or L363 cells were injected into the lateral tail vein of C.B.-17 SCID mice. Mice were dosed with humanized 1F6 (HJLA) or control non-binding antibody by intraperitoneal (i.p.) injection every four days for a total of six doses (Raji) or by intravenous injection into the lateral tail vein once weekly for a total of four weeks (MM.1S and L363) starting one day after cell implant. Disease requiring euthanasia was manifested by hunched posture and lack of grooming, weight loss, cranial swelling and hind limb paralysis, or, in L363-bearing mice, the development of palpable lymphoid tissue-associated tumors.

The results show that, in each tumor model (FIGS. 7A, 7B and 7C), survival of mice treated with humanized 1F6 was significantly prolonged compared to that of untreated mice or mice receiving non-binding control antibody. The effect of humanized 1F6 treatment was further evaluated in multiple myeloma xenografts (L363 and MM.1S cells) by measuring the level of tumor-derived monoclonal protein (λ light chain) in the sera of individual mice. As shown in FIGS. 7B and 7C (right panels), circulating λ light chain concentrations were significantly lower in mice treated with humanized 1F6 as compared to untreated mice. Mean serum levels of λ light chain in L363-bearing mice treated with humanized 1F6 were 0.006 µg/mL compared to 0.10 µg/mL in sera of untreated mice. Similarly, λ light chain levels in humanized 1F6-treated MM.1S-bearing mice were 0.03 µg/mL compared to 1.25 µg/mL in untreated mice. These results were consistent with the increased survival rates of the mice (FIGS. 7B and 7C, right panels).

Example 9

In Vitro Deletion of CD70+ Antigen-Specific T Cells by Humanized 1F6 Antibody To test the ability of humanized 1F6 antibody to deplete antigen-specific activated T cells, PBMC from a normal donor expressing HLA-A0201 were stimulated with the M1 peptide in the presence or absence of varying concentrations of humanized anti-CD70 antibody. Humanized 1F6 antibody (HJLA) was prepared as described above. PBMC were seeded in a 24-well plate at a concentration of $0.5 \times 10^6$ cells/ml with 5 μg/ml M1 peptide in 2 ml of medium supplemented with IL-2 and IL-15. On day 5, half of the culture supernatant was replaced with fresh cytokine-containing medium. On day 9, the percentage of antigen-reactive cells (the $CD8^+/V\beta17^+$ population) was determined by flow cytometric analysis of cells stained with FITC-conjugated anti-Vβ17- and PE-Cy5-conjugated anti-CD8 antibodies.

Figure 8:
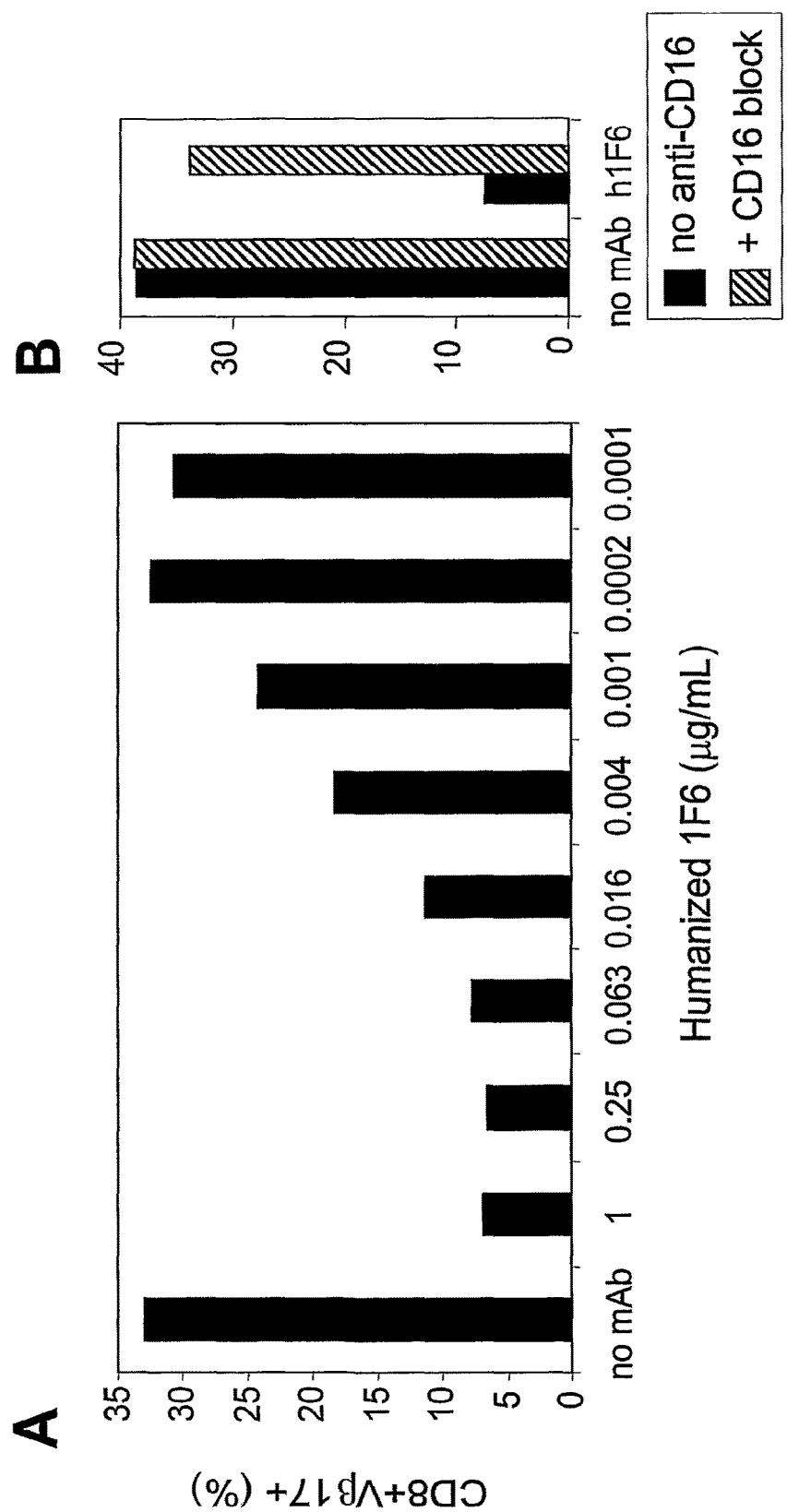
FIG. 8 shows humanized 1F6 mediates depletion of antigen-specific CD8+/Vβ17+ cells. PBMCs from a normal HLA-A0201 donor were stimulated with the M1 peptide. (A) Peptide-stimulated cultures were untreated or treated with concurrent addition of graded doses of humanized 1F6 antibody, as indicated. The percent CD8+/Vβ17+ cells after 9 days was determined by flow cytometry. (B) Peptide-stimulated cultures were untreated or treated on day 0 with 1 µg/ml humanized 1F6 in the absence (solid bars) or presence (hatched bars) of 10 µg/ml antibody specific for FcγRIII (CD16). The percent CD8+/Vβ7+ cells after 9 days was determined by flow cytometry.

FIG. 8A shows that antigen-specific $CD8^+/V\beta17^+$ cells expanded to comprise 33% of all viable cells within the culture in the absence of antibody. In contrast, addition of humanized 1F6 to the cultures on day 0 significantly limited expansion of the antigen-reactive population in an antibody-dose dependent manner. These results show that humanized 1F6 selectively targets and prevents the expansion of antigen-activated T cells.

In a second study (FIG. 8B), M1-peptide stimulated cultures were untreated or treated with humanized 1F6 in the absence or presence of antibody that specifically blocks FcγRIII (CD16). In untreated cultures, the antigen-specific $CD8+V\beta17^+$ population expanded to comprise 39% of all viable cells within the culture. Addition of humanized 1F6 significantly diminished expansion of the reactive population. This activity was largely reversed when FcγRIII receptors were blocked with anti-CD16 specific antibody, indicating that deletion of peptide-reactive cells was mediated via humanized 1F6 interaction with FcgRIII-bearing effector cells.

Example 10

Anti-CD70 Antibody does not Affect Antigen-Negative Bystander Cells

To determine the effect of 1F6-mediated depletion on antigen-negative bystander T cells, the TCR Vβ family representation of CD4 and CD8 lymphocytes was examined in M1-activated cultures that were untreated or treated with a chimeric variant of 1F6 (c1F6) (human IgG1 isotype) and compared to resting, non-antigen stimulated PBMC. Chimeric and humanized 1F6 variants are comparable in binding affinity, capacity to mediate effector functions, and ability to deplete activated CD8+ T cell subsets.

Figure 9:
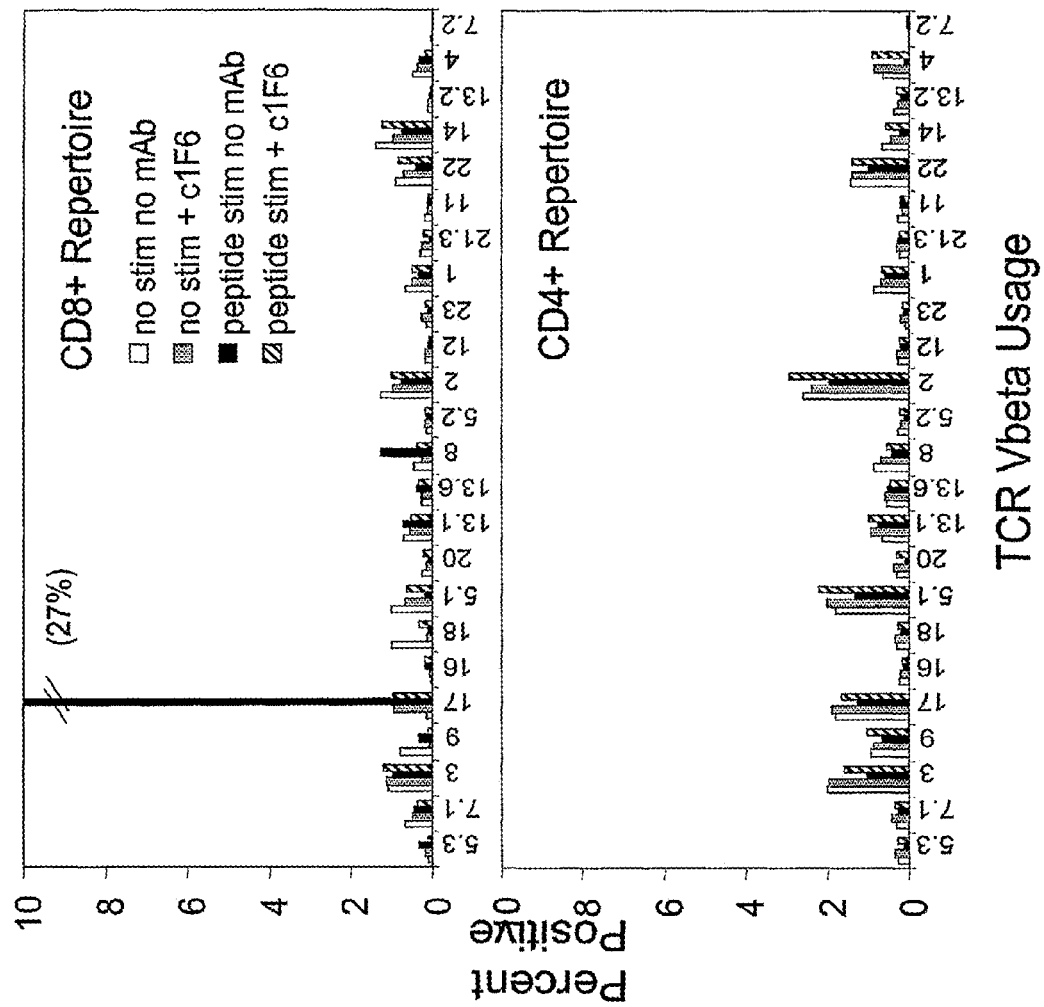
FIG. 9 shows minimal impact of anti-CD70 1F6 antibody on bystander resting T cells. PBMCs from a normal HLA-A0201 donor were untreated (no stim) or stimulated with M1 peptide (peptide stim) in the presence or absence of 1 µg/mL c1F6. After nine days in culture, Vβ TCR representation among CD4 and CD8 cells from each group was analyzed by flow cytometry using the IOTest® Beta Mark TCR Vβ Repertoire Kit.

As shown in FIG. 9, stimulation of $HLA-A0201^+$ PBMC with M1 peptide caused the expansion of $CD8^+$ cells bearing the Vβ17 TCR approximately 30-fold, whereas all other Vβ TCR families tested in $CD8^+$ cells and all families tested in the CD4 cell population demonstrated minimal change. In the control population, cell expansion was limited to the $V\beta17^+CD8^+$ T cell subset, which increased from <1% of $CD8^+$ cells to 27%; this observation confirms the specificity of the M1-peptide immune response. Unlike T cells stimulated in the absence of CD 70-specific antibody, expansion of M1-peptide specific $CD8^+$ cells was prevented by the addition of c1F6 antibody to the culture. In the presence of c1F6 antibody, the percent $V\beta17^+CD8^+$ cells was comparable to that of resting, non-peptide stimulated cells. Treatment with c1F6 antibody did not significantly perturb the relative representations of other $CD8^+$ or $CD4^+$ Vβ TCR families; no group was observed to be eliminated. These data demonstrate that exposure to c1F6 antibody selectively depletes $CD70^+$ activated T cells without causing detectable collateral damage to bystander T cell populations.

Example 11

Mouse Xenograft Model of Renal Cell Carcinoma

Figure 10A:
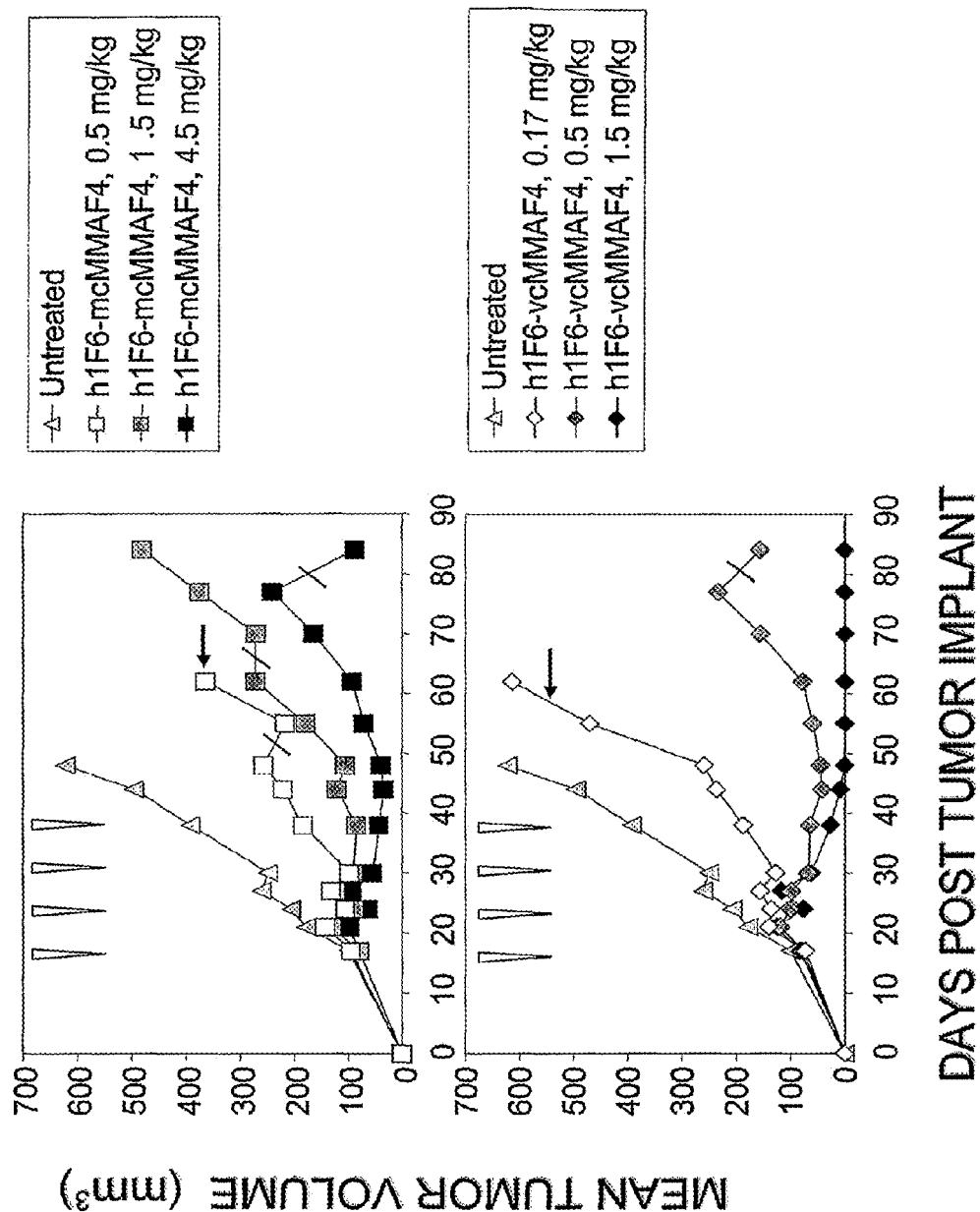
FIG. 10 shows a mouse Xenograft model of Renal Cell Carcinoma. (A) Subcutaneous 786-O tumors were initiated in nude mice by implanting tumor fragments (N=5 or 6/group) of approximately 30 mm$^3$. Tumor growth was allowed to establish and treatment began when average tumor size within each group was approximately 100 mm$^3$ h1F6-mcMMAF4 or h1F6-vcMMAF4 at the indicated doses was administered at a q4d×4 schedule beginning on day 17 after tumor implantation, as indicated by the arrows. Cross-strikes indicate when animals with tumors >1000 mm$^3$ were euthanized. (B) 786-O tumor implantation and treatment initiation are the same as given in (A). Groups of mice (N=5-7) were administered with h1F6-mcMMAF4 or h1F6-vcMMAF4 at 0.17 mg/kg at a q4d×4 or q4d×10 schedule beginning on day 13 after tumor implantation. Tumor growth is represented by Kaplan-Meier plots. An event was registered when a mouse with a tumor quadrupled in size compared to day 13 when treatment began. Mice with tumors that did not quadruple in size at the end of the experiment on day 43 were censored. The log-rank test was used to generate p values between treatment groups and the untreated group.

A 786-O subcutaneous xenograft model was used to evaluate antitumor activity of anti-CD70 ADCs administered at different dosages and schedules. Subcutaneous 786-O tumors were initiated in nude mice by implanting tumor fragments (N=5 or 6/group) of approximated 30 mm³. Tumor growth was allowed to establish and treatment began when average tumor size was approximately 100 mm³. Tumor dimensions were determined by caliper measurements to monitor growth. Tumor size was calculated using the formula of (length×width²)/2. In the absence of any treatment, mean tumor volume increased to approximately 600 mm³ within 40 to 50 days after tumor implantation (see FIG. 10A). A dose-dependent effect in tumor growth suppression was observed in mice which received either humanized 1F6-mcMMAF4 (HJLA with a loading level of an average of four drug units per antibody) or humanized 1F6-vcMMAF4 (HJLA with a loading level of an average of four drug units per antibody). Detectable delay in tumor growth was observed even at 0.5 and 0.17 mg/kg of h1F6-mcMMAF4 and h1F6-vcMMAF4, respectively.

Figure 10B:
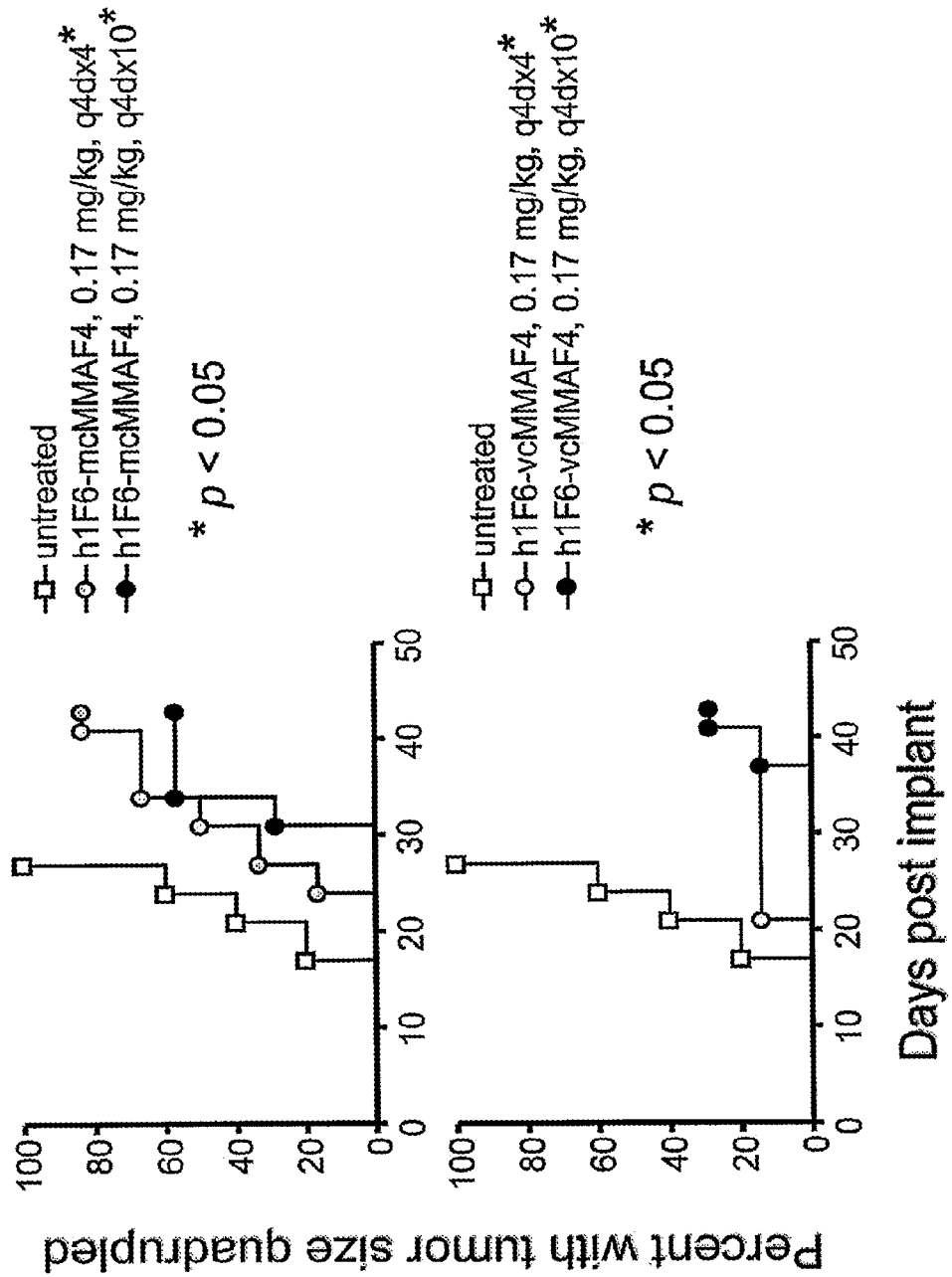

Tumor growth was also assessed by time needed for tumors to quadruple in size (see FIG. 10B). Treatment with either h1F6-mcMMAF4 or h1F6-vcMMAF4 at 0.17 mg/kg significantly delayed the growth of tumors. This delay was observed when the ADCs were given on a q4d×4 or q4d×10 schedule. However, additional administrations as exemplified by the q4d×10 schedule appeared to have a stronger growth inhibitory activity compared to the q4d×4 schedule.

Example 12

Expression of CD70 on Multiple Myeloma Cell Lines

Cell surface CD70 expression was evaluated in a panel of multiple myeloma cell lines (Table 6). Copy number of CD70 molecules expressed by each cell line was determined by quantitative flow cytometry using the QIFIKit® (Dako, Carpinteria, Calif.). Response of these cells to anti-CD70 ADC-mediated cytotoxicity was determined. In this model, the activity of chimeric anti-CD70 ADCs is a proxy for activity of human anti-CD70 ADCs. Both chimeric 1F6 (c1F6)-vcMMAF4 and c1F6-mcMMAF4 were cytotoxic against CD70-expressing multiple myeloma cells. The $IC_{50}$ values obtained with c1F6-vcMMAF4 ranged from 1.2-160 ng/mL while that obtained with c1F6-mcMMAF4 ranged from 1.7-500 ng/mL.

TABLE 6

Cytotoxic Activity of Chimeric Anti-CD70 ADCs against Multiple Myeloma Cell Lines

| | | $IC_{50}$ (ng/mL) | |
|---|---|---|---|
| | CD70 copies/cell | c1F6-vcMMAF4 | c1F6-mcMMAF4 |
| MM.1S | 14,000 | 20 | 22 |
| MM.1R | 25,000 | 13 | 20 |
| AMO-1 | 92,000 | 16 | 38 |
| JJN-3 | 19,000 | 46 | 61 |

TABLE 6-continued

Cytotoxic Activity of Chimeric Anti-CD70 ADCs against Multiple Myeloma Cell Lines

| | | $IC_{50}$ (ng/mL) | |
|---|---|---|---|
| | CD70 copies/cell | c1F6-vcMMAF4 | c1F6-mcMMAF4 |
| L363 | 13,000 | 78 | 210 |
| LB | 45,000 | 80 | 500 |
| U266 | 155,000 | 1.2 | 1.7 |
| LP-1 | 34,000 | 160 | 155 |
| MOLP-8 | 9,000 | 73 | 33 |

Example 13

Mouse Xenograft Models of Multiple Myeloma

Figure 11A:
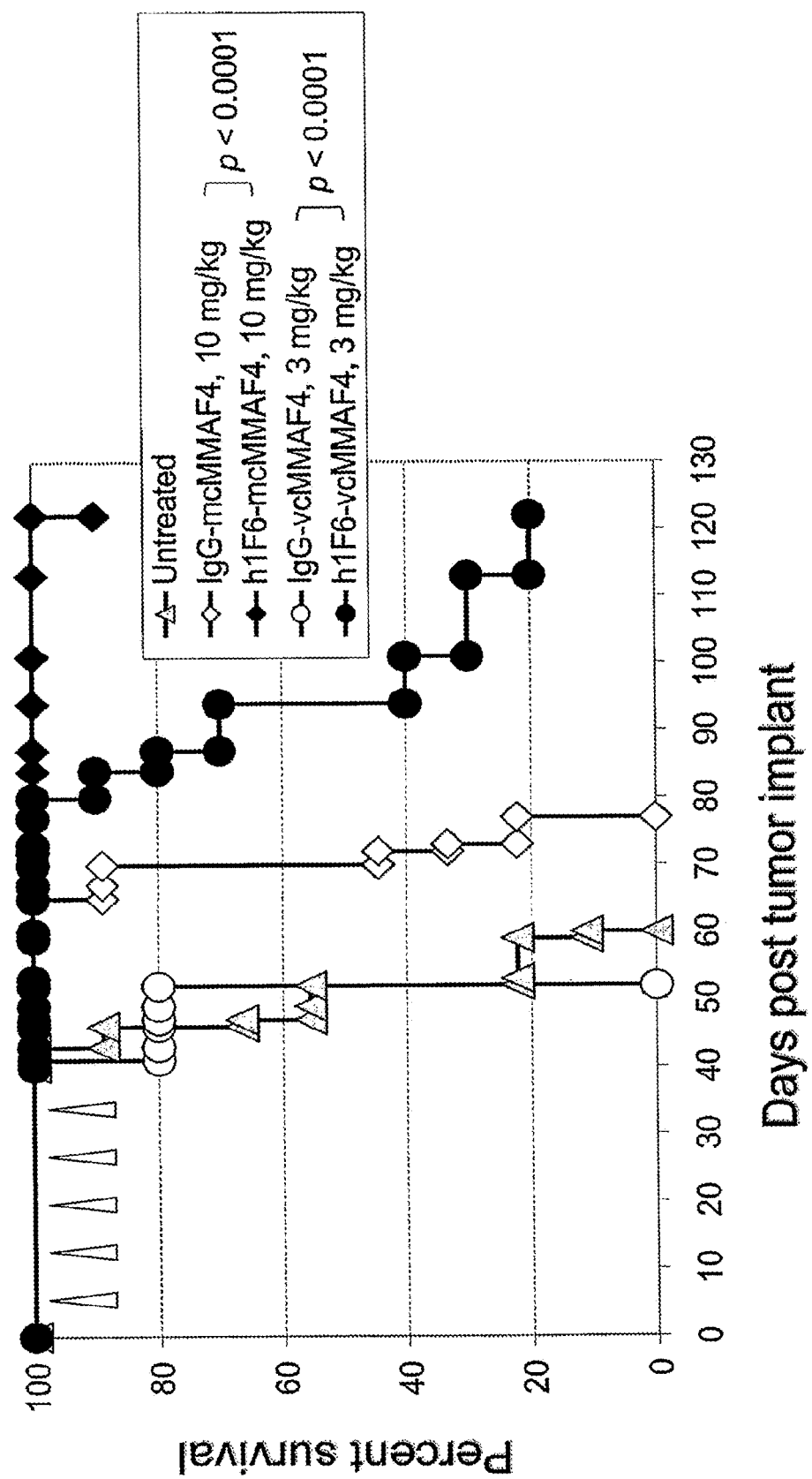
FIG. 11 shows a mouse Xenograft Model of Multiple Myeloma. (A) Ten million MM-1S cells were injected intravenously into each SCID mouse. Groups of mice (N=8-10) were left untreated, received IgG-vcMMAF4, IgG-mcMMAF4, h1F6-vcMMAF4, or h1F6-mcMMAF4 at the specified doses on a q7d×5 schedule, as indicated by the arrows. Mice showing symptoms of hind limb paralysis, hunched posture, cranial swelling, and/or scruffy coat were euthanized, and the percent survival of each group was plotted. The log-rank test was used to generate p values between treatment groups and the control groups. (B) Bone marrow cells were recovered from the femurs of euthanized mice due to the above disease symptoms or on day 122 post tumor cell implantation when the experiment was terminated. The percentage of CD138-expressing MM-1S cells in the femers of each mouse was determined by flow cytometry. The Mann-Whitney test was used to derived p values between the indicated groups.

The in vivo activity of anti-CD70 ADCs in xenograft models of multiple myeloma was further examined. Human multiple myeloma cell lines MM-1S (FIGS. 11A & 11B) or L363 (FIGS. 12A & 12B) were resuspended in RPMI-1640 medium at the concentration of $10 \times 10^6$ cells/300 μL. To establish tumors 300 μL of cell suspension were injected intravenously through the tail veins of SCID mice. In the MM-1S model, untreated mice succumbed to the injected tumor cells and manifested symptoms around 40 days post tumor implant including hind limb paralysis, hunched posture, cranial swelling, and/or scruffy coat. Mice were euthanized when they demonstrated one or more of these symptoms. Both h1F6(HJLA)-vcMMAF4 and h1F6(HJLA)-mcMMAF4 provided significant survival benefits to tumor bearing mice compared to control non-binding IgG-vcMMAF4 and IgG-mcMMAF4 (see FIG. 11A). Tumor burden in the MM-1S model was also assessed by enumerating the number of bone marrow cells expressing human CD138, a plasma cell marker expressed by the MM-1S cells. Bone marrow cells were recovered from mice that were euthanized due to manifestation of symptom or at the end of the experiment on day 122, and the number of CD138-expressing MM-1S cells was determined by flow cytometry. Compared to untreated mice, both control IgG-vcMMAF4 and IgG-mcMMAF4 did not significantly reduce the number of CD138-expressing cells in the bone marrow. On the other hand, h1F6-vcMMAF4 and h1F6-mcMMAF4 significantly reduce tumor burden as demonstrated by much lower number of bone marrow CD138-expressing cells compared to the control ADCs (see FIG. 11B).

Figure 12A:
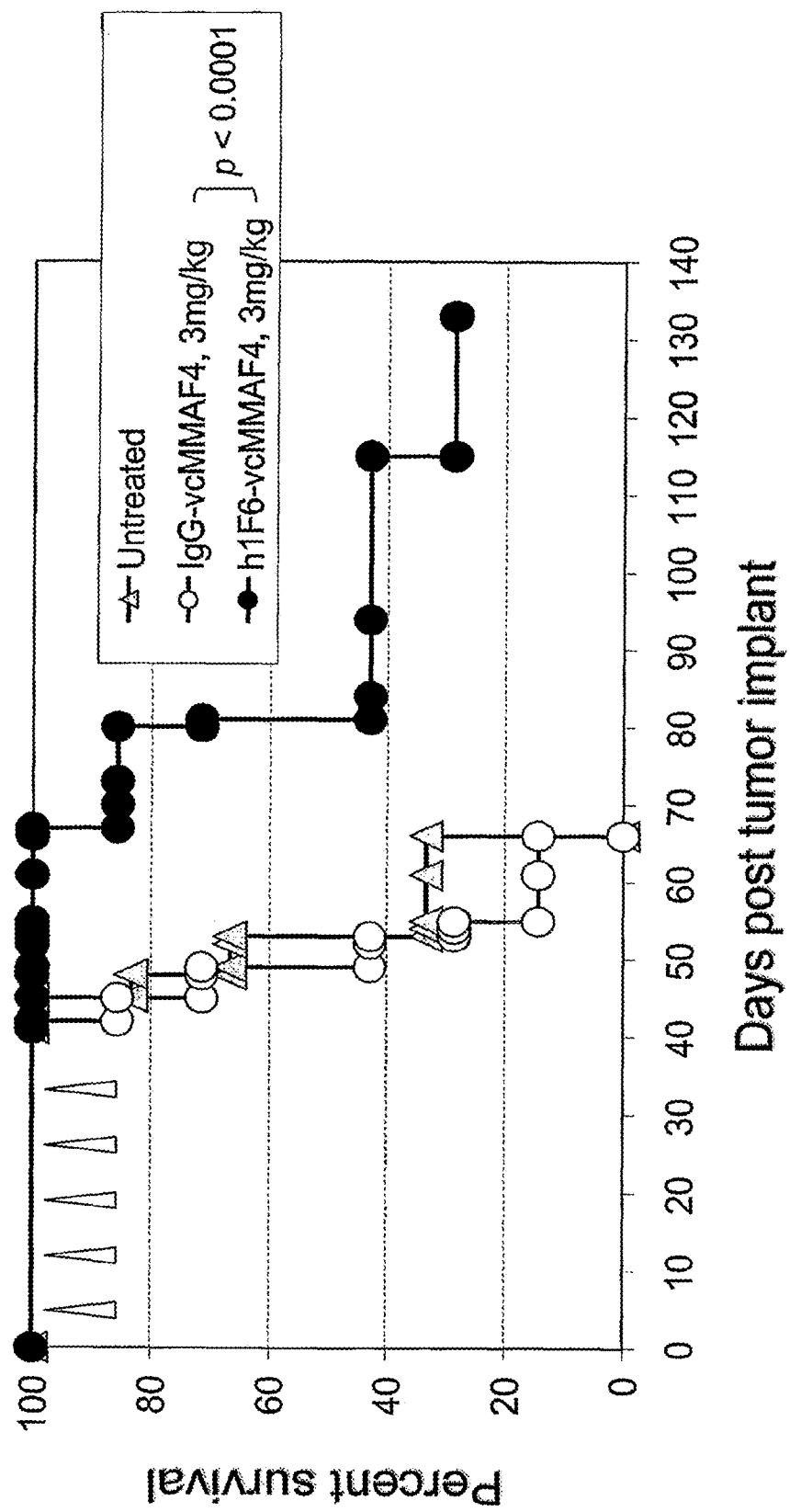
FIG. 12 shows a mouse Xenograft model of Multiple Myeloma. (A) Ten million L363 cells were injected intravenously into each SCID mouse. Groups of mice (N=7) were left untreated, received IgG-vcMMAF4, or h1F6-vcMMAF4 at the specified doses on a q7d×5 schedule as indicated by the arrows. Mice showing palpable tumor masses were euthanized, and the percent survival of each group was plotted. The log-rank test was used to generate the p value between the treated group and the untreated group. (B) Serum samples were obtained from mice 40 days after tumor implant. The concentration of human λ light chain in the serum of each mouse was determined by ELISA. The Mann-Whitney test was used to derive p values between the indicated groups.

In the L363 model, disseminated tumor masses develop at multiple locations in mice receiving no treatment, and tumor masses became palpable around 40 days after tumor injection, at which tumor bearing mice would be euthanized. Similar to the MM-1S model, control IgG-vcMMAF4 provided no survival advantage, whereas h1F6-vcMMAF4 significantly prolonged survival (see FIG. 12A). Since L363 cells secrete immunoglobulin lambda light chain (λ LC), tumor burden can be determined by monitoring the level of human λ LC in the plasma of tumor bearing mice. An ELISA was used to detect secreted λ LC. Ninety six-well flat-bottom Immuno plates (Nunc Maxisorp, #442404, Nalge Nunc International, Rochester, N.Y.) was coated with 100 μL/well of goat anti-human Ig (Southern Biotech #2010-01, Birmingham, Ala.) at 2 μg/mL in 0.1M sodium carbonate/bicarbonate overnight at 4° C. Wells were washed 5× with 1×PBST (PBS, 0.05% Tween-20), and blocked with 200 μL/well of 1% BSA/PBST (0.05% Tween-20) for 1 hour at room temperature. After 5 washes with 1×PBST, serially diluted human λ LC-containing mouse serum samples were added. Purified human λ LC (Bethyl labs, #P80-127, Montgomery, Tex.) was used as the standard. After one hour of incubation at room temperature, wells were washed 5 times with 1×PBST. HRP-goat anti-human lambda chain specific F(ab')₂ (Southern Biotech #2072-05) at 1:4000 dilution in 1% BSA/PBST was added. After an additional one hour incubation at room temperature, wells were washed 5 times with 1×PBST. TMB substrate 100 μL/well (Sigma, #T8665, St. Louis, Mo.) was used to detect captured λ LC. FIG. 12B shows the results at forty days after L363 cell implant serum. λ LC levels were comparable between the untreated mice and the IgG-vcMMAF4-treated mice. In contrast, serum λ LC levels in the h1F6-vcMMAF4-treated mice were significantly lower, confirming the ability of anti-CD70 ADC to reduce tumor burden in mice bearing multiple myeloma xenografts.

Example 14

Expression of CD70 on Hodgkin's and Glioblastoma Cell Lines

Cell surface CD70 expression was also evaluated in panels of Hodgkin's disease (Table 7) and glioblastoma cell lines (Table 8). The copy number of CD70 molecules expressed by each cell line was determined by quantitative flow cytometry using the QIFIKit® (Dako, Carpinteria, Calif.). The response of these cells to chimeric anti-CD70 ADC-mediated cytotoxicity was determined. In this model, the activity of chimeric anti-CD70 ADCs is a proxy for activity of human anti-CD70 ADCs. Both chimeric 1F6 (c1F6)-vcMMAF4 and c1F6-mcMMAF4 were cytotoxic against these CD70-expressing cell lines. In the Hodgkin's disease panel, the $IC_{50}$ values obtained with c1F6-vcMMAF4 ranged from 0.41-42 ng/mL while that obtained with c1F6-mcMMAF4 ranged from 5.2-310 ng/mL (Table 7). In the glioblastoma panel, the $IC_{50}$ values obtained with h1F6-vcMMAF4 ranged from 2.3-27 ng/mL while that obtained with h1F6-mcMMAF4 ranged from 15-110 ng/mL (Table 8).

TABLE 7

Cytotoxic Activity of Anti-CD70 ADCs against Hodgkin's Disease Cell Lines

| | | $IC_{50}$ (ng/mL) | |
|---|---|---|---|
| | CD70 copies/cell | c1F6-vcMMAF4 | c1F6-mcMMAF4 |
| RPMI-6666 | 21,000 | 42 | 230 |
| Hs445 | 64,000 | 7.3 | 310 |
| L428 | 105,000 | 1.4 | 35 |
| KMH2 | 160,000 | 0.41 | 5.2 |
| SUP-HD-1 | 221,000 | 6.3 | 53 |

TABLE 8

Cytotoxic Activity of Chimeric Anti-CD70 ADCs against Glioblastoma Cell Lines

| | | $IC_{50}$ (ng/mL) | |
|---|---|---|---|
| | CD70 copies/cell | h1F6-vcMMAF4 | h1F6-mcMMAF4 |
| U251 | 117,000 | 5.3 | 15 |
| SNB-19 | 90,000 | 12 | 27 |
| U373MG | 70,000 | 16 | 35 |
| GMS-10 | 64,000 | 27 | 110 |
| DBTRG-05MG | 59,000 | 2.3 | 20 |

The present invention is not to be limited in scope by the specific embodiments described herein. Indeed, various modifications of the invention in addition to those described

What is claimed is:

1. An isolated polynucleotide encoding a humanized heavy chain variable region comprising the three CDRs from SEQ ID NO:2 and a variable region framework sequence of human germline $V_H1$-2 or $V_H1$-18 and exon $J_H$-6, provided that any of positions H46, H67, H68, H69, H70, H71, H80, H81, H82, H82A and H91 (Kabat numbering) can be occupied by the amino acid occupying the corresponding position from SEQ ID NO:2.

2. The isolated polynucleotide of claim 1, further encoding a human IgG constant region.

3. The isolated polynucleotide of claim 2, wherein the IgG constant region is IgG1 or IgG3.

4. The isolated polynucleotide of claim 2, wherein the humanized heavy chain variable region and the human IgG constant region together comprise the amino acid sequence corresponding to residues 20-467 of SEQ ID NO:16 or residues 20-467 of SEQ ID NO:20.

5. The isolated polynucleotide of claim 4, comprising the nucleotide sequence of nucleotides 58-1401 of SEQ ID NO:15 or nucleotides 58-1401 of SEQ ID NO:19.

6. The isolated polynucleotide of claim 1, wherein position H46 is occupied by the amino acid occupying the corresponding position from SEQ ID NO:2.

7. The isolated polynucleotide of claim 1, wherein at least one of positions H46, H67, H68, H69, H70, H71, H80, H81, H82, H82A and H91 (Kabat numbering) in the humanized heavy chain variable region is occupied by the residue occupying the corresponding position in SEQ ID NO:2.

8. The isolated polynucleotide of claim 7, wherein at least one of positions H71 and H91 (Kabat numbering) in the humanized heavy chain variable region is occupied by the residue occupying the corresponding position in SEQ ID NO:2.

9. The isolated polynucleotide of claim 1, wherein the humanized heavy chain variable region comprises the amino acid sequence set forth in SEQ ID NO:6, SEQ ID NO:10, SEQ ID NO:14, SEQ ID NO:18, or amino acids 20-137 of SEQ ID NO:4.

10. An isolated polynucleotide, comprising the nucleotide sequence set forth in SEQ ID NO:5, SEQ ID NO:9, SEQ ID NO:13, SEQ ID NO:17, or nucleotides 58-411 of SEQ ID NO:3.

11. An isolated polynucleotide encoding a humanized light chain variable region comprising the three CDRs from SEQ ID NO:22 and a variable region framework sequence of human germline Vκ exon B3 and Jκ exon Jκ-1, provided that any of positions L25 and L33 can be occupied by the amino acid occupying the corresponding position from SEQ ID NO:22.

12. The isolated polynucleotide of claim 11, further encoding a light chain constant region.

13. The isolated polynucleotide of claim 12, wherein the light chain constant region is a human kappa constant domain.

14. The isolated polynucleotide of claim 12, wherein the humanized light chain variable region and the light chain constant region together comprise the amino acid sequence corresponding to residues 21-238 of SEQ ID NO:26.

15. The isolated polynucleotide of claim 14, comprising the nucleotide sequence of nucleotides 61-714 of SEQ ID NO:25.

16. The isolated polynucleotide of claim 11, wherein at least one of positions L25 and L33 in the humanized light chain variable region is occupied by the residue occupying the corresponding position in SEQ ID NO:22.

17. The isolated polynucleotide of claim 11, wherein the humanized light chain variable region comprises the amino acid sequence of SEQ ID NO:24.

18. An isolated polynucleotide, comprising the nucleotide sequence set forth in SEQ ID NO:23.

19. The isolated polynucleotide of claim 11, further encoding a humanized heavy chain variable region comprising the three CDRs from SEQ ID NO:2 and a variable region framework sequence of human germline $V_H$1-2 or $V_H$1-18 and exon $J_H$-6, provided that any of positions H46, H67, H68, H69, H70, H71, H80, H81, H82, H82A and H91 (Kabat numbering) can be occupied by the amino acid occupying the corresponding position from SEQ ID NO:2.

20. The isolated polynucleotide of claim 10, further comprising the nucleotide sequence set forth in SEQ ID NO:23.

21. The isolated polynucleotide of claim 20, wherein the humanized heavy chain variable region is encoded by the nucleotide sequence set forth in SEQ ID NO:13 or SEQ ID NO:17, and the humanized light chain variable region is encoded by the sequence set forth in SEQ ID NO:23.

22. A vector comprising the isolated polynucleotide of claim 1.

23. A vector comprising the isolated polynucleotide of claim 11.

24. A host cell transfected with the vector of claim 22.

25. A host cell transfected with the vector of claim 23.

26. The host cell of claim 24 that is a mammalian host cell.

27. The host cell of claim 26, wherein the mammalian host cell is selected from the group consisting of CHO, VERO, BHK, HeLa, COS, MDCK, 293, 3T3, and W138 cells.

28. The host cell of claim 25 that is a mammalian host cell.

29. The host cell of claim 28, wherein the mammalian host cell is selected from the group consisting of CHO, VERO, BHK, HeLa, COS, MDCK, 293, 3T3, and W138 cells.

30. A method of producing an antibody, comprising culturing the host cell of claim 24 to produce the antibody.

31. A method of producing an antibody, comprising culturing the host cell of claim 25 to produce the antibody.

* * * * *

SEQUENCE LISTING

<160> NUMBER OF SEQ ID NOS: 33

<210> SEQ ID NO 1
<211> LENGTH: 411
<212> TYPE: DNA
<213> ORGANISM: Mus musculus

<400> SEQUENCE: 1

| | | | | | |
|---|---|---|---|---|---|
| atggcttggg | tgtggacctt | gctattcctg | atggcagctg | cccaaagtgc | ccaagcacag | 60 |
| atccagttgg | tgcagtctgg | acctgaggtg | aagaagcctg | agagacagt | caagatctcc | 120 |
| tgcaaggctt | ctgggtatac | cttcacaaac | tatggaatga | actgggtgaa | gcaggctcca | 180 |
| ggaaagggtt | taaagtggat | gggctggata | aacacctaca | ctggagagcc | aacatatgct | 240 |
| gatgccttca | agggacggtt | tgccttctct | ttggaaacct | ctgccagcac | tgcctatttg | 300 |
| cagatcaaca | acctcaaaaa | tgaggacacg | gctacatatt | tctgtgcaag | agactacggc | 360 |
| gactatggta | tggactactg | gggtcaagga | acctcagtca | ccgtctcctc | a | 411 |

<210> SEQ ID NO 2
<211> LENGTH: 137
<212> TYPE: PRT
<213> ORGANISM: Mus musculus

<400> SEQUENCE: 2

Met Ala Trp Val Trp Thr Leu Leu Phe Leu Met Ala Ala Ala Gln Ser
1               5                   10                  15

Ala Gly Ala Gln Ile Gln Leu Val Gln Ser Gly Pro Glu Val Lys Lys
            20                  25                  30

Pro Gly Glu Thr Val Lys Ile Ser Cys Lys Ala Ser Gly Tyr Thr Phe
        35                  40                  45

Thr Asn Tyr Gly Met Asn Trp Val Lys Gln Ala Pro Gly Lys Gly Leu
    50                  55                  60

Lys Trp Met Gly Trp Ile Asn Thr Tyr Thr Gly Glu Pro Thr Tyr Ala
65                  70                  75                  80

Asp Ala Phe Lys Gly Arg Phe Ala Phe Ser Leu Glu Thr Ser Ala Ser
                85                  90                  95

Thr Ala Tyr Leu Gln Ile Asn Asn Leu Lys Asn Glu Asp Thr Ala Thr
            100                 105                 110

Tyr Phe Cys Ala Arg Asp Tyr Gly Asp Tyr Gly Met Asp Tyr Trp Gly
        115                 120                 125

Gln Gly Thr Ser Val Thr Val Ser Ser
    130                 135

<210> SEQ ID NO 3
<211> LENGTH: 1404
<212> TYPE: DNA
<213> ORGANISM: Artificial
<220> FEATURE:
<223> OTHER INFORMATION: murine CDR, human FR in HV Domain

<400> SEQUENCE: 3

| | | | | | |
|---|---|---|---|---|---|
| atggcttggg | tgtggacctt | gctattcctg | atggcagctg | cccaaagtgc | ccaagcacag | 60 |
| gttcagctgg | tgcagtctgg | agctgaggtg | aagaagcctg | gggcctcagt | gaaggtctcc | 120 |

-continued

```
tgcaaggctt ctggttacac ctttaccaac tatggaatga actgggtgcg acaggcccct      180
ggacaagggc ttgagtggat gggatggatc aacacctaca ctggagagcc aacatatgct      240
gatgccttca agggcagagt caccatgacc acagacacat ccacgagcac agcctacatg      300
gagctgagga gcctgagatc tgacgacacg gccgtgtatt actgtgcgag agactacggc      360
gactatggta tggactactg gggtcaagga accaccgtca ccgtctcctc agctagcacc      420
aagggcccat cggtcttccc cctggcaccc tcctccaaga gcacctctgg gggcacagcg      480
gccctgggct gcctggtcaa ggactacttc cccgaaccgg tgacggtgtc gtggaactca      540
ggcgccctga ccagcggcgt gcacaccttc ccggctgtcc tacagtcctc aggactctac      600
tccctcagca gcgtggtgac cgtgccctcc agcagcttgg gcacccagac ctacatctgc      660
aacgtgaatc acaagcccag caacaccaag gtggacaaga agttgagcc caaatcttgt      720 gacaaaactc acacatgccc accgtgccca gcacctgaac tcctgggggg accgtcagtc      780
ttcctcttcc ccccaaaacc caaggacacc ctcatgatct cccggacccc tgaggtcaca      840
tgcgtggtgg tggacgtgag ccacgaagac cctgaggtca agttcaactg gtacgtggac      900
ggcgtggagg tgcataatgc caagacaaag ccgcgggagg agcagtacaa cagcacgtac      960
cgtgtggtca gcgtcctcac cgtcctgcac caggactggc tgaatggcaa ggagtacaag     1020
tgcaaggtct ccaacaaagc cctcccagcc cccatcgaga aaccatctc caaagccaaa      1080 gggcagcccc gagaaccaca ggtgtacacc ctgcccccat cccgggatga gctgaccaag     1140
aaccaggtca gcctgacctg cctggtcaaa ggcttctatc ccagcgacat cgccgtggag     1200
tgggagagca atgggcagcc ggagaacaac tacaagacca cgcctcccgt gctggactcc     1260
gacggctcct tcttcctcta cagcaagctc accgtggaca agagcaggtg gcagcagggg     1320
aacgtcttct catgctccgt gatgcatgag gctctgcaca accactacac gcagaagagc     1380
ctctccctgt ctccgggtaa atga                                            1404
```

<210> SEQ ID NO 4
<211> LENGTH: 467
<212> TYPE: PRT
<213> ORGANISM: Artificial
<220> FEATURE:
<223> OTHER INFORMATION: murine CDR, human FR in HV Domain

<400> SEQUENCE: 4

```
Met Ala Trp Val Trp Thr Leu Leu Phe Leu Met Ala Ala Ala Gln Ser
1               5                   10                  15

Ala Gln Ala Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Asn Tyr Gly Met Asn Trp Val Arg Gln Ala Pro Gly Gln Gly Leu
    50                  55                  60

Glu Trp Met Gly Trp Ile Asn Thr Tyr Thr Gly Glu Pro Thr Tyr Ala
65                  70                  75                  80

Asp Ala Phe Lys Gly Arg Val Thr Met Thr Thr Asp Thr Ser Thr Ser
                85                  90                  95

Thr Ala Tyr Met Glu Leu Arg Ser Leu Arg Ser Asp Asp Thr Ala Val
            100                 105                 110

Tyr Tyr Cys Ala Arg Asp Tyr Gly Asp Tyr Gly Met Asp Tyr Trp Gly
        115                 120                 125

Gln Gly Thr Thr Val Thr Val Ser Ser Ala Ser Thr Lys Gly Pro Ser
```

```
          130                 135                 140
Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
                180                 185                 190

Val Leu Gln Ser Ser Gly Leu Tyr Ser Leu Ser Ser Val Val Thr Val
                195                 200                 205

Pro Ser Ser Ser Leu Gly Thr Gln Thr Tyr Ile Cys Asn Val Asn His
            210                 215                 220

Lys Pro Ser Asn Thr Lys Val Asp Lys Val Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
                260                 265                 270

Ile Ser Arg Thr Pro Glu Val Thr Cys Val Val Val Asp Val Ser His
            275                 280                 285

Glu Asp Pro Glu Val Lys Phe Asn Trp Tyr Val Asp Gly Val Glu Val
290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
                340                 345                 350

Glu Lys Thr Ile Ser Lys Ala Lys Gly Gln Pro Arg Glu Pro Gln Val
                355                 360                 365

Tyr Thr Leu Pro Pro Ser Arg Asp Glu Leu Thr Lys Asn Gln Val Ser
        370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
                420                 425                 430

Asp Lys Ser Arg Trp Gln Gln Gly Asn Val Phe Ser Cys Ser Val Met
                435                 440                 445

His Glu Ala Leu His Asn His Tyr Thr Gln Lys Ser Leu Ser Leu Ser
450                 455                 460

Pro Gly Lys
465

<210> SEQ ID NO 5
<211> LENGTH: 354
<212> TYPE: DNA
<213> ORGANISM: Artificial
<220> FEATURE:
<223> OTHER INFORMATION: murine CDR, human FR

<400> SEQUENCE: 5
caggttcagc tggtgcagtc tggagctgag gtgaagaagc ctggggcctc agtgaaggtc    60
tcctgcaagg cttctggtta cacctttacc aactatggaa tgaactgggt gcgacaggcc   120
```

| | | |
|---|---|---|
| cctggacaag ggcttgagtg gatgggatgg atcaacacct acactggaga gccaacatat | 180 | |
| gctgatgcct tcaagggcag agtcaccatg accagagaca catccatcag cacagcctac | 240 | |
| atggagctga gcaggctgag atctgacgac acggccgtgt attactgtgc gagagactac | 300 | |
| ggcgactatg gtatggacta ctggggtcaa ggaaccaccg tcaccgtctc ctca | 354 | |

<210> SEQ ID NO 6
<211> LENGTH: 118
<212> TYPE: PRT
<213> ORGANISM: Artificial
<220> FEATURE:
<223> OTHER INFORMATION: murine CDR, human FR

<400> SEQUENCE: 6

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Pro Thr Tyr Ala Asp Ala Phe
    50                  55                  60

Lys Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Tyr Gly Asp Tyr Gly Met Asp Tyr Trp Gly Gln Gly Thr
            100                 105                 110

Thr Val Thr Val Ser Ser
        115

<210> SEQ ID NO 7
<211> LENGTH: 1404
<212> TYPE: DNA
<213> ORGANISM: Artificial
<220> FEATURE:
<223> OTHER INFORMATION: murine CDR, human FR in HV Domain

<400> SEQUENCE: 7

| | | |
|---|---|---|
| atggcttggg tgtggacctt gctattcctg atgcagctg cccaaagtgc ccaagcacag | 60 | |
| gttcagctgg tgcagtctgg agctgaggtg aagaagcctg ggcctcagt gaaggtctcc | 120 | |
| tgcaaggctt ctggttacac ctttaccaac tatggaatga ctgggtgcg acaggcccct | 180 | |
| ggacaagggc ttgagtggat gggatggatc aacacctaca ctggagagcc aacatatgct | 240 | |
| gatgccttca gggcagagt caccatgacc agagacacat ccatcagcac agcctacatg | 300 | |
| gagctgagca ggctgagatc tgacgacacg gccgtgtatt actgtgcgag agactacggc | 360 | |
| gactatggta tggactactg gggtcaagga accaccgtca ccgtctcctc agctagcacc | 420 | |
| aagggcccat cggtcttccc cctggcaccc tcctccaaga gcacctctgg gggcacagcg | 480 | |
| gccctgggct gcctggtcaa ggactacttc cccgaaccgg tgacggtgtc gtggaactca | 540 | |
| ggcgccctga ccagcggcgt gcacaccttc ccggctgtcc tacagtcctc aggactctac | 600 | |
| tccctcagca gcgtggtgac cgtgccctcc agcagcttgg gcacccagac ctacatctgc | 660 | |
| aacgtgaatc acaagcccag caacaccaag gtggacaaga agttgagcc caaatcttgt | 720 | |
| gacaaaactc acacatgccc accgtgccca gcacctgaac tcctggggg accgtcagtc | 780 | |
| ttcctcttcc cccaaaaacc caaggacacc ctcatgatct cccggacccc tgaggtcaca | 840 | |

```
tgcgtggtgg tggacgtgag ccacgaagac cctgaggtca agttcaactg gtacgtggac    900
ggcgtggagg tgcataatgc caagacaaag ccgcgggagg agcagtacaa cagcacgtac    960
cgtgtggtca gcgtcctcac cgtcctgcac caggactggc tgaatggcaa ggagtacaag   1020
tgcaaggtct ccaacaaagc cctcccagcc cccatcgaga aaaccatctc caaagccaaa   1080
gggcagcccc gagaaccaca ggtgtacacc ctgcccccat cccgggatga gctgaccaag   1140
aaccaggtca gcctgacctg cctggtcaaa ggcttctatc ccagcgacat cgccgtggag   1200
tgggagagca atgggcagcc ggagaacaac tacaagacca cgcctcccgt gctggactcc   1260
gacggctcct tcttcctcta cagcaagctc accgtggaca agagcaggtg gcagcagggg   1320
aacgtcttct catgctccgt gatgcatgag gctctgcaca accactacac gcagaagagc   1380 ctctcccctgt ctccgggtaa atga                                          1404
```

<210> SEQ ID NO 8
<211> LENGTH: 467
<212> TYPE: PRT
<213> ORGANISM: Artificial
<220> FEATURE:
<223> OTHER INFORMATION: murine CDR, human FR in HV Domain

<400> SEQUENCE: 8

```
Met Ala Trp Val Trp Thr Leu Leu Phe Leu Met Ala Ala Ala Gln Ser
1               5                   10                  15

Ala Gln Ala Gln Val Gln Leu Val Gln Ser Gly Ala Glu Val Lys Lys
                20                  25                  30

Pro Gly Ala Ser Val Lys Val Ser Cys Lys Ala Ser Gly Tyr Thr Phe
            35                  40                  45

Thr Asn Tyr Gly Met Asn Trp Val Arg Gln Ala Pro Gly Gln Gly Leu
        50                  55                  60

Glu Trp Met Gly Trp Ile Asn Thr Tyr Thr Gly Glu Pro Thr Tyr Ala
65                  70                  75                  80

Asp Ala Phe Lys Gly Arg Val Thr Met Thr Arg Asp Thr Ser Ile Ser
                85                  90                  95

Thr Ala Tyr Met Glu Leu Ser Arg Leu Arg Ser Asp Asp Thr Ala Val
            100                 105                 110

Tyr Tyr Cys Ala Arg Asp Tyr Gly Asp Tyr Gly Met Asp Tyr Trp Gly
        115                 120                 125

Gln Gly Thr Thr Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Val Glu Pro Lys Ser Cys
225                 230                 235                 240

Asp Lys Thr His Thr Cys Pro Pro Cys Pro Ala Pro Glu Leu Leu Gly
                245                 250                 255
```

```
Gly Pro Ser Val Phe Leu Phe Pro Pro Lys Pro Lys Asp Thr Leu Met
            260                 265                 270
Ile Ser Arg Thr Pro Glu Val Thr Cys Val Val Val Asp Val Ser His
        275                 280                 285
Glu Asp Pro Glu Val Lys Phe Asn Trp Tyr Val Asp Gly Val Glu Val
    290                 295                 300
His Asn Ala Lys Thr Lys Pro Arg Glu Glu Gln Tyr Asn Ser Thr Tyr
305                 310                 315                 320
Arg Val Val Ser Val Leu Thr Val Leu His Gln Asp Trp Leu Asn Gly
                325                 330                 335
Lys Glu Tyr Lys Cys Lys Val Ser Asn Lys Ala Leu Pro Ala Pro Ile
            340                 345                 350
Glu Lys Thr Ile Ser Lys Ala Lys Gly Gln Pro Arg Glu Pro Gln Val
        355                 360                 365
Tyr Thr Leu Pro Pro Ser Arg Asp Glu Leu Thr Lys Asn Gln Val Ser
    370                 375                 380
Leu Thr Cys Leu Val Lys Gly Phe Tyr Pro Ser Asp Ile Ala Val Glu
385                 390                 395                 400
Trp Glu Ser Asn Gly Gln Pro Glu Asn Asn Tyr Lys Thr Thr Pro Pro
                405                 410                 415
Val Leu Asp Ser Asp Gly Ser Phe Phe Leu Tyr Ser Lys Leu Thr Val
            420                 425                 430
Asp Lys Ser Arg Trp Gln Gln Gly Asn Val Phe Ser Cys Ser Val Met
        435                 440                 445
His Glu Ala Leu His Asn His Tyr Thr Gln Lys Ser Leu Ser Leu Ser
    450                 455                 460
Pro Gly Lys
465

<210> SEQ ID NO 9
<211> LENGTH: 354
<212> TYPE: DNA
<213> ORGANISM: Artificial
<220> FEATURE:
<223> OTHER INFORMATION: murine CDR, murine residues in human FR

<400> SEQUENCE: 9
caggttcagc tggtgcagtc tggagctgag gtgaagaagc ctggggcctc agtgaaggtc      60
tcctgcaagg cttctggtta cacctttacc aactatggaa tgaactgggt gcgacaggcc     120
cctggacaag gcttgagtg gatgggatgg atcaacacct acactggaga gccaacatat     180
gctgatgcct caagggcag atttgccttc tctttggaca catccacgag cacagcctac     240
ttgcagatca acagcctgag atctgacgac acggccgtgt attactgtgc gagagactac     300
ggcgactatg gtatggacta ctggggtcaa ggaaccaccg tcaccgtctc ctca           354

<210> SEQ ID NO 10
<211> LENGTH: 118
<212> TYPE: PRT
<213> ORGANISM: Artificial
<220> FEATURE:
<223> OTHER INFORMATION: murine CDR, murine residues in human FR

<400> SEQUENCE: 10

Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Asn Tyr
            20                  25                  30
```

Gly Met Asn Trp Val Arg Gln Ala Pro Gly Gln Gly Leu Glu Trp Met
        35                  40                  45

Gly Trp Ile Asn Thr Tyr Thr Gly Glu Pro Thr Tyr Ala Asp Ala Phe
50                  55                  60

Lys Gly Arg Phe Ala Phe Ser Leu Asp Thr Ser Thr Ser Thr Ala Tyr
65                  70                  75                  80

Leu Gln Ile Asn Ser Leu Arg Ser Asp Asp Thr Ala Val Tyr Tyr Cys
                85                  90                  95

Ala Arg Asp Tyr Gly Asp Tyr Gly Met Asp Tyr Trp Gly Gln Gly Thr
            100                 105                 110

Thr Val Thr Val Ser Ser
        115

<210> SEQ ID NO 11
<211> LENGTH: 1404
<212> TYPE: DNA
<213> ORGANISM: Artificial
<220> FEATURE:
<223> OTHER INFORMATION: murine CDR, murine residues in human FR

<400> SEQUENCE: 11

```
atggcttggg tgtggacctt gctattcctg atggcagctg cccaaagtgc ccaagcacag     60
gttcagctgg tgcagtctgg agctgaggtg aagaagcctg ggccgcagt gaaggtctcc    120
tgcaaggctt ctggttacac ctttaccaac tatggaatga actgggtgcg acaggcccct    180
ggacaagggc ttgagtggat gggatggatc aacacctaca ctggagagcc aacatatgct    240
gatgccttca agggcagatt tgccttctct ttggacacat ccacgagcac agcctacttg    300
cagatcaaca gcctgagatc tgacgacacg gccgtgtatt actgtgcgag agactacggc    360
gactatggta tggactactg gggtcaagga accaccgtca ccgtctcctc agctagcacc    420
aagggcccat cggtcttccc cctggcaccc tcctccaaga gcacctctgg gggcacagcg    480
gccctgggct gcctggtcaa ggactacttc cccgaaccgg tgacggtgtc gtggaactca    540
ggcgccctga ccagcggcgt gcacaccttc ccggctgtcc tacagtcctc aggactctac    600
tccctcagca gcgtggtgac cgtgccctcc agcagcttgg gcacccagac ctacatctgc    660
aacgtgaatc acaagcccag caacaccaag gtggacaaga agttgagcc caaatcttgt    720
gacaaaactc acacatgccc accgtgccca gcacctgaac tcctgggggg accgtcagtc    780
ttcctcttcc ccccaaaacc caaggacacc ctcatgatct cccggacccc tgaggtcaca    840
tgcgtggtgg tggacgtgag ccacgaagac cctgaggtca agttcaactg gtacgtggac    900
ggcgtggagg tgcataatgc caagacaaag ccgcgggagg agcagtacaa cagcacgtac    960
cgtgtggtca gcgtcctcac cgtcctgcac caggactggc tgaatggcaa ggagtacaag   1020
tgcaaggtct ccaacaaagc cctcccagcc cccatcgaga aaccatctc caaagccaaa   1080
gggcagcccc gagaaccaca ggtgtacacc ctgcccccat cccgggatga gctgaccaag   1140
aaccaggtca gcctgacctg cctggtcaaa ggcttctatc ccagcgacat cgccgtggag   1200
tgggagagca atgggcagcc ggagaacaac tacaagacca cgcctcccgt gctggactcc   1260
gacggctcct tcttcctcta cagcaagctc accgtggaca agagcaggtg gcagcagggg   1320
aacgtcttct catgctccgt gatgcatgag gctctgcaca accactacac gcagaagagc   1380
ctctccctgt ctccgggtaa atga                                          1404
```

<210> SEQ ID NO 12

```
<211> LENGTH: 467
<212> TYPE: PRT
<213> ORGANISM: Artificial
<220> FEATURE:
<223> OTHER INFORMATION: murine CDR, murine residues in human FR

<400> SEQUENCE: 12

Met Ala Trp Val Trp Thr Leu Leu Phe Leu Met Ala Ala Ala Gln Ser
1               5                   10                  15

Ala Gln Ala Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Asn Tyr Gly Met Asn Trp Val Arg Gln Ala Pro Gly Gln Gly Leu
    50                  55                  60

Glu Trp Met Gly Trp Ile Asn Thr Tyr Thr Gly Glu Pro Thr Tyr Ala
65                  70                  75                  80

Asp Ala Phe Lys Gly Arg Phe Ala Phe Ser Leu Asp Thr Ser Thr Ser
                85                  90                  95

Thr Ala Tyr Leu Gln Ile Asn Ser Leu Arg Ser Asp Asp Thr Ala Val
            100                 105                 110

Tyr Tyr Cys Ala Arg Asp Tyr Gly Asp Tyr Gly Met Asp Tyr Trp Gly
        115                 120                 125

Gln Gly Thr Thr Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Lys Val Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
    290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Arg Asp Glu Leu Thr Lys Asn Gln Val Ser
    370                 375                 380
```

-continued

```
Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
            405                 410                 415

Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
            435                 440                 445

His Glu Ala Leu His Asn His Tyr Thr Gln Lys Ser Leu Ser Leu Ser
            450                 455                 460

Pro Gly Lys
465

<210> SEQ ID NO 13
<211> LENGTH: 354
<212> TYPE: DNA
<213> ORGANISM: Artificial
<220> FEATURE:
<223> OTHER INFORMATION: murine CDR, murine residues in human FR

<400> SEQUENCE: 13
caggttcagc tggtgcagtc tggagctgag gtgaagaagc ctggggcctc agtgaaggtc      60
tcctgcaagg cttctggtta cacctttacc aactatggaa tgaactgggt gcgacaggcc     120
cctggacaag ggcttaagtg gatgggatgg atcaacacct acactggaga gccaacatat     180
gctgatgcct tcaagggcag agtcaccatg accagagaca catccatcag cacagcctac     240
atggagctga gcaggctgag atctgacgac acggccgtgt attactgtgc gagagactac     300
ggcgactatg gtatggacta ctggggtcaa ggaaccaccg tcaccgtctc ctca           354

<210> SEQ ID NO 14
<211> LENGTH: 118
<212> TYPE: PRT
<213> ORGANISM: Artificial
<220> FEATURE:
<223> OTHER INFORMATION: murine CDR, murine residues in human FR

<400> SEQUENCE: 14

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Lys Trp Met
        35                  40                  45

Gly Trp Ile Asn Thr Tyr Thr Gly Glu Pro Thr Tyr Ala Asp Ala Phe
50                  55                  60

Lys Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
            85                  90                  95

Ala Arg Asp Tyr Gly Asp Tyr Gly Met Asp Tyr Trp Gly Gln Gly Thr
            100                 105                 110

Thr Val Thr Val Ser Ser
        115

<210> SEQ ID NO 15
<211> LENGTH: 1404
<212> TYPE: DNA
```

<213> ORGANISM: Artificial
<220> FEATURE:
<223> OTHER INFORMATION: murine CDR, murine residues in human FR

<400> SEQUENCE: 15

```
atggcttggg tgtggacctt gctattcctg atggcagctg cccaaagtgc ccaagcacag    60
gttcagctgg tgcagtctgg agctgaggtg aagaagcctg ggcctcagt gaaggtctcc    120
tgcaaggctt ctggttacac ctttaccaac tatggaatga actgggtgcg acaggcccct    180
ggacaagggc ttaagtggat gggatggatc aacacctaca ctggagagcc aacatatgct    240
gatgccttca agggcagagt caccatgacc agagacacat ccatcagcac agcctacatg    300
gagctgagca ggctgagatc tgacgacacg gccgtgtatt actgtgcgag agactacggc    360
gactatggta tggactactg gggtcaagga accaccgtca ccgtctcctc agctagcacc    420
aagggcccat cggtcttccc cctggcaccc tcctccaaga gcacctctgg gggcacagcg    480
gccctgggct gcctggtcaa ggactacttc cccgaaccgg tgacggtgtc gtggaactca    540
ggcgccctga ccagcggcgt gcacaccttc ccggctgtcc tacagtcctc aggactctac    600
tccctcagca gcgtggtgac cgtgccctcc agcagcttgg gcacccagac ctacatctgc    660
aacgtgaatc acaagcccag caacaccaag gtggacaaga agttgagcc caaatcttgt    720
gacaaaactc acacatgccc accgtgccca gcacctgaac tcctgggggg accgtcagtc    780
ttcctcttcc cccaaaaacc caaggacacc ctcatgatct cccggacccc tgaggtcaca    840
tgcgtggtgg tggacgtgag ccacgaagac cctgaggtca agttcaactg gtacgtggac    900
ggcgtggagg tgcataatgc caagacaaag ccgcgggagg agcagtacaa cagcacgtac    960
cgtgtggtca gcgtcctcac cgtcctgcac caggactggc tgaatggcaa ggagtacaag    1020
tgcaaggtct ccaacaaagc cctcccagcc ccatcgaga aaaccatctc caaagccaaa    1080
gggcagcccc gagaaccaca ggtgtacacc ctgcccccat cccgggatga gctgaccaag    1140
aaccaggtca gcctgacctg cctggtcaaa ggcttctatc ccagcgacat cgccgtggag    1200
tgggagagca atgggcagcc ggagaacaac tacaagacca cgcctcccgt gctggactcc    1260
gacggctcct tcttcctcta cagcaagctc accgtggaca gagcaggtg gcagcagggg    1320
aacgtcttct catgctccgt gatgcatgag gctctgcaca accactacac gcagaagagc    1380
ctctccctgt ctccgggtaa atga    1404
```

<210> SEQ ID NO 16
<211> LENGTH: 467
<212> TYPE: PRT
<213> ORGANISM: Artificial
<220> FEATURE:
<223> OTHER INFORMATION: murine CDR, murine residues in human FR

<400> SEQUENCE: 16

```
Met Ala Trp Val Trp Thr Leu Leu Phe Leu Met Ala Ala Ala Gln Ser
1               5                   10                  15

Ala Gln Ala Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Asn Tyr Gly Met Asn Trp Val Arg Gln Ala Pro Gly Gln Gly Leu
    50                  55                  60

Lys Trp Met Gly Trp Ile Asn Thr Tyr Thr Gly Glu Pro Thr Tyr Ala
65                  70                  75                  80
```

```
Asp Ala Phe Lys Gly Arg Val Thr Met Thr Arg Asp Thr Ser Ile Ser
                85                  90                  95

Thr Ala Tyr Met Glu Leu Ser Arg Leu Arg Ser Asp Thr Ala Val
            100                 105                 110

Tyr Tyr Cys Ala Arg Asp Tyr Gly Asp Tyr Gly Met Asp Tyr Trp Gly
            115                 120                 125

Gln Gly Thr Thr Val Thr Val Ser Ser Ala Ser Thr Lys Gly Pro Ser
130             135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Lys Val Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
    290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Arg Asp Glu Leu Thr Lys Asn Gln Val Ser
    370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
450                 455                 460

Pro Gly Lys
465

<210> SEQ ID NO 17
<211> LENGTH: 354
<212> TYPE: DNA
```

<213> ORGANISM: Artificial
<220> FEATURE:
<223> OTHER INFORMATION: murine CDR, murine residues in human FR

<400> SEQUENCE: 17

```
caggttcagc tggtgcagtc tggagctgag gtgaagaagc ctggggcctc agtgaaggtc      60
tcctgcaagg cttctggtta cacctttacc aactatggaa tgaactgggt gcgacaggcc     120
cctggacaag gcttaagtg gatgggatgg atcaacacct acactggaga gccaacatat      180
gctgatgcct tcaagggcag atttgccttc tctttggaca catccacgag cacagcctac     240
atggagctga ggagcctgag atctgacgac acggccgtgt attactgtgc gagagactac     300
ggcgactatg gtatggacta ctggggtcaa ggaaccaccg tcaccgtctc ctca           354
```

<210> SEQ ID NO 18
<211> LENGTH: 118
<212> TYPE: PRT
<213> ORGANISM: Artificial
<220> FEATURE:
<223> OTHER INFORMATION: murine CDR, murine residues in human FR

<400> SEQUENCE: 18

```
Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Asn Tyr
            20                  25                  30
Gly Met Asn Trp Val Arg Gln Ala Pro Gly Gln Gly Leu Lys Trp Met
        35                  40                  45
Gly Trp Ile Asn Thr Tyr Thr Gly Glu Pro Thr Tyr Ala Asp Ala Phe
    50                  55                  60
Lys Gly Arg Phe Ala Phe Ser Leu Asp Thr Ser Thr Ser Thr Ala Tyr
65                  70                  75                  80
Met Glu Leu Arg Ser Leu Arg Ser Asp Asp Thr Ala Val Tyr Tyr Cys
                85                  90                  95
Ala Arg Asp Tyr Gly Asp Tyr Gly Met Asp Tyr Trp Gly Gln Gly Thr
            100                 105                 110
Thr Val Thr Val Ser Ser
        115
```

<210> SEQ ID NO 19
<211> LENGTH: 1404
<212> TYPE: DNA
<213> ORGANISM: Artificial
<220> FEATURE:
<223> OTHER INFORMATION: murine CDR, murine residues in human FR

<400> SEQUENCE: 19

```
atggcttggg tgtggacctt gctattcctg atggcagctg cccaaagtgc ccaagcacag      60
gttcagctgg tgcagtctgg agctgaggtg aagaagcctg ggcctcagt gaaggtctcc     120
tgcaaggctt ctggttacac ctttaccaac tatggaatga actgggtgcg acaggcccct    180
ggacaagggc ttaagtggat gggatggatc aacacctaca ctggagagcc aacatatgct    240
gatgccttca aggcagatt tgccttctct ttggacacat ccacgagcac agcctacatg      300
gagctgagga gcctgagatc tgacgacacg gccgtgtatt actgtgcgag agactacggc    360
gactatggta tggactactg gggtcaagga accaccgtca ccgtctcctc agctagcacc    420
aagggcccat cggtcttccc cctggcaccc tcctccaaga gcacctctgg gggcacagcg    480
gccctgggct gcctggtcaa ggactacttc cccgaaccgg tgacggtgtc gtggaactca    540
```

```
ggcgccctga ccagcggcgt gcacaccttc ccggctgtcc tacagtcctc aggactctac    600
tccctcagca gcgtggtgac cgtgccctcc agcagcttgg gcacccagac ctacatctgc    660
aacgtgaatc acaagcccag caacaccaag gtggacaaga agttgagcc caaatcttgt     720 gacaaaactc acacatgccc accgtgccca gcacctgaac tcctgggggg accgtcagtc    780
ttcctcttcc ccccaaaacc caaggacacc ctcatgatct cccggacccc tgaggtcaca    840
tgcgtggtgg tggacgtgag ccacgaagac cctgaggtca agttcaactg gtacgtggac    900
ggcgtggagg tgcataatgc caagacaaag ccgcgggagg agcagtacaa cagcacgtac    960
cgtgtggtca gcgtcctcac cgtcctgcac caggactggc tgaatggcaa ggagtacaag    1020
tgcaaggtct ccaacaaagc cctcccagcc ccatcgaga aaaccatctc caaagccaaa     1080
gggcagcccc gagaaccaca ggtgtacacc ctgcccccat cccgggatga gctgaccaag    1140
aaccaggtca gcctgacctg cctggtcaaa ggcttctatc ccagcgacat cgccgtggag    1200
tgggagagca tgggcagcc ggagaacaac tacaagacca cgcctcccgt gctggactcc     1260
gacggctcct tcttcctcta cagcaagctc accgtggaca gagcaggtg gcagcagggg     1320 aacgtcttct catgctccgt gatgcatgag gctctgcaca accactacac gcagaagagc    1380
ctctccctgt ctccgggtaa atga                                           1404
```

<210> SEQ ID NO 20
<211> LENGTH: 467
<212> TYPE: PRT
<213> ORGANISM: Artificial
<220> FEATURE:
<223> OTHER INFORMATION: murine CDR, murine residues in human FR

<400> SEQUENCE: 20

```
Met Ala Trp Val Trp Thr Leu Leu Phe Leu Met Ala Ala Ala Gln Ser
1               5                   10                  15

Ala Gln Ala Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Asn Tyr Gly Met Asn Trp Val Arg Gln Ala Pro Gly Gln Gly Leu
    50                  55                  60

Lys Trp Met Gly Trp Ile Asn Thr Tyr Thr Gly Glu Pro Thr Tyr Ala
65                  70                  75                  80

Asp Ala Phe Lys Gly Arg Phe Ala Phe Ser Leu Asp Thr Ser Thr Ser
                85                  90                  95

Thr Ala Tyr Met Glu Leu Arg Ser Leu Arg Ser Asp Asp Thr Ala Val
            100                 105                 110

Tyr Tyr Cys Ala Arg Asp Tyr Gly Asp Tyr Gly Met Asp Tyr Trp Gly
        115                 120                 125

Gln Gly Thr Thr Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205
```

Pro Ser Ser Ser Leu Gly Thr Gln Thr Tyr Ile Cys Asn Val Asn His
    210                 215                 220
Lys Pro Ser Asn Thr Lys Val Asp Lys Val Glu Pro Lys Ser Cys
225                 230                 235                 240
Asp Lys Thr His Thr Cys Pro Pro Cys Pro Ala Pro Glu Leu Leu Gly
                245                 250                 255
Gly Pro Ser Val Phe Leu Phe Pro Pro Lys Pro Lys Asp Thr Leu Met
                260                 265                 270
Ile Ser Arg Thr Pro Glu Val Thr Cys Val Val Val Asp Val Ser His
            275                 280                 285
Glu Asp Pro Glu Val Lys Phe Asn Trp Tyr Val Asp Gly Val Glu Val
290                 295                 300
His Asn Ala Lys Thr Lys Pro Arg Glu Glu Gln Tyr Asn Ser Thr Tyr
305                 310                 315                 320
Arg Val Val Ser Val Leu Thr Val Leu His Gln Asp Trp Leu Asn Gly
                325                 330                 335
Lys Glu Tyr Lys Cys Lys Val Ser Asn Lys Ala Leu Pro Ala Pro Ile
                340                 345                 350
Glu Lys Thr Ile Ser Lys Ala Lys Gly Gln Pro Arg Glu Pro Gln Val
            355                 360                 365
Tyr Thr Leu Pro Pro Ser Arg Asp Glu Leu Thr Lys Asn Gln Val Ser
370                 375                 380
Leu Thr Cys Leu Val Lys Gly Phe Tyr Pro Ser Asp Ile Ala Val Glu
385                 390                 395                 400
Trp Glu Ser Asn Gly Gln Pro Glu Asn Asn Tyr Lys Thr Thr Pro Pro
                405                 410                 415
Val Leu Asp Ser Asp Gly Ser Phe Phe Leu Tyr Ser Lys Leu Thr Val
                420                 425                 430
Asp Lys Ser Arg Trp Gln Gln Gly Asn Val Phe Ser Cys Ser Val Met
            435                 440                 445
His Glu Ala Leu His Asn His Tyr Thr Gln Lys Ser Leu Ser Leu Ser
450                 455                 460
Pro Gly Lys
465

<210> SEQ ID NO 21
<211> LENGTH: 396
<212> TYPE: DNA
<213> ORGANISM: Mus musculus

<400> SEQUENCE: 21
atggagacag acacactcct gttatgggta ctgctgctct ggttccagg ttccactggt      60 gacattgtgc tgacacagtc tcctgcttcc ttagctgtat ctctgggca gagggccacc     120 atctcatgca gggccagcaa aagtgtcagt acatctggct atagttttat gcactggtat     180
caacagaaac caggacagcc acccaaactc ctcatctatc ttgcatccaa cctagaatct     240
ggggtccctg ccaggttcag tggcagtggg tctgggacag acttcaccct caacatccat     300
cctgtggagg aggaggatgc tgcaacctat tactgtcagc acagtaggga ggttccgtgg     360
acgttcggtg gaggcaccaa gctggaaatc aaacgg                               396

<210> SEQ ID NO 22
<211> LENGTH: 132
<212> TYPE: PRT
<213> ORGANISM: Mus musculus

<400> SEQUENCE: 22

Met Glu Thr Asp Thr Leu Leu Leu Trp Val Leu Leu Leu Trp Val Pro
1               5                   10                  15

Gly Ser Thr Gly Asp Ile Val Leu Thr Gln Ser Pro Ala Ser Leu Ala
            20                  25                  30

Val Ser Leu Gly Gln Arg Ala Thr Ile Ser Cys Arg Ala Ser Lys Ser
        35                  40                  45

Val Ser Thr Ser Gly Tyr Ser Phe Met His Trp Tyr Gln Gln Lys Pro
    50                  55                  60

Gly Gln Pro Pro Lys Leu Leu Ile Tyr Leu Ala Ser Asn Leu Glu Ser
65                  70                  75                  80

Gly Val Pro Ala Arg Phe Ser Gly Ser Gly Ser Gly Thr Asp Phe Thr
                85                  90                  95

Leu Asn Ile His Pro Val Glu Glu Glu Asp Ala Ala Thr Tyr Tyr Cys
            100                 105                 110

Gln His Ser Arg Glu Val Pro Trp Thr Phe Gly Gly Gly Thr Lys Leu
        115                 120                 125

Glu Ile Lys Arg
    130

<210> SEQ ID NO 23
<211> LENGTH: 336
<212> TYPE: DNA
<213> ORGANISM: Artificial
<220> FEATURE:
<223> OTHER INFORMATION: murine CDR, human FR

<400> SEQUENCE: 23
gacatcgtga tgacccagtc tccagactcc ctggctgtgt ctctgggcga gagggccacc    60
atcaactgca gggccagcaa aagtgtcagt acatctggct atagttttat gcactggtac   120
cagcagaaac caggacagcc tcctaagctg ctcatttacc ttgcatccaa cctagaatcc   180
ggggtccctg accgattcag tggcagcggg tctgggacag atttcactct caccatcagc   240
agcctgcagg ctgaagatgt ggcagtttat tactgtcagc acagtaggga ggttccgtgg   300
acgttcggtc agggcaccaa ggtggaaatc aaacgt                             336

<210> SEQ ID NO 24
<211> LENGTH: 112
<212> TYPE: PRT
<213> ORGANISM: Artificial
<220> FEATURE:
<223> OTHER INFORMATION: murine CDR, human FR

<400> SEQUENCE: 24

Asp Ile Val Met Thr Gln Ser Pro Asp Ser Leu Ala Val Ser Leu Gly
1               5                   10                  15

Glu Arg Ala Thr Ile Asn Cys Arg Ala Ser Lys Ser Val Ser Thr Ser
            20                  25                  30

Gly Tyr Ser Phe Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln His Ser Arg
                85                  90                  95

Glu Val Pro Trp Thr Phe Gly Gln Gly Thr Lys Val Glu Ile Lys Arg
            100                 105                 110

<210> SEQ ID NO 25
<211> LENGTH: 717
<212> TYPE: DNA
<213> ORGANISM: Artificial
<220> FEATURE:
<223> OTHER INFORMATION: murine CDR, human FR

<400> SEQUENCE: 25
atggagacag acacactcct gttatgggta ctgctgctct gggttccagg ttccactggt        60
gacatcgtga tgacccagtc tccagactcc ctggctgtgt ctctgggcga gagggccacc       120
atcaactgca gggccagcaa aagtgtcagt acatctggct atagttttat gcactggtac       180
cagcagaaac aggacagcc tcctaagctg ctcatttacc ttgcatccaa cctagaatcc        240
ggggtccctg accgattcag tggcagcggg tctgggacag atttcactct caccatcagc       300
agcctgcagg ctgaagatgt ggcagtttat tactgtcagc acagtaggga ggttccgtgg       360
acgttcggtc agggcaccaa ggtggaaatc aaacgtacgg tggctgcacc atctgtcttc       420
atcttcccgc catctgatga gcagttgaaa tctggaactg cctctgttgt gtgcctgctg       480
aataacttct atcccagaga ggccaaagta cagtggaagg tggataacgc cctccaatcg       540
ggtaactccc aggagagtgt cacagagcag gacagcaagg acagcaccta cagcctcagc       600
agcaccctga cgctgagcaa agcagactac gagaaacaca agtctacgc ctgcgaagtc        660 acccatcagg gcctgagctc gcccgtcaca aagagcttca caggggaga gtgttag          717

<210> SEQ ID NO 26
<211> LENGTH: 238
<212> TYPE: PRT
<213> ORGANISM: Artificial
<220> FEATURE:
<223> OTHER INFORMATION: murine CDR, human FR

<400> SEQUENCE: 26

Met Glu Thr Asp Thr Leu Leu Leu Trp Val Leu Leu Trp Val Pro
1               5                   10                  15

Gly Ser Thr Gly Asp Ile Val Met Thr Gln Ser Pro Asp Ser Leu Ala
            20                  25                  30

Val Ser Leu Gly Glu Arg Ala Thr Ile Asn Cys Arg Ala Ser Lys Ser
        35                  40                  45

Val Ser Thr Ser Gly Tyr Ser Phe Met His Trp Tyr Gln Gln Lys Pro
    50                  55                  60

Gly Gln Pro Pro Lys Leu Leu Ile Tyr Leu Ala Ser Asn Leu Glu Ser
65                  70                  75                  80

Gly Val Pro Asp Arg Phe Ser Gly Ser Gly Ser Gly Thr Asp Phe Thr
                85                  90                  95

Leu Thr Ile Ser Ser Leu Gln Ala Glu Asp Val Ala Val Tyr Tyr Cys
            100                 105                 110

Gln His Ser Arg Glu Val Pro Trp Thr Phe Gly Gln Gly Thr Lys Val
        115                 120                 125

Glu Ile Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn 165                 170                 175
Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235

<210> SEQ ID NO 27
<211> LENGTH: 411
<212> TYPE: DNA
<213> ORGANISM: Mus musculus

<400> SEQUENCE: 27
atggaatgga cctgggtctt tctcttcctc ctgccagtaa ctgcagatgt ccaatcccag      60
gttcagctgc aacagtctgg aactgagctg atgacgcctg ggcctcagt gacgatgtcc     120 tgcaagactt ctggctacac attcagtacc tactggatag agtgggtaaa acagaggcct    180
ggacatggcc ttgagtggat tggagaaatt ttacctggaa gtggttatac tgactacaat    240
gagaagttca aggccaaggc cacattcact gcagatacat cctccaacac agcctacatg    300
caactcagca gcctggcatc tgaggactct gccgtctatt actgtgcaag atgggatagg    360
ctctatgcta tggactactg gggtcaagga acctcagtca ccgtctcctc a             411

<210> SEQ ID NO 28
<211> LENGTH: 137
<212> TYPE: PRT
<213> ORGANISM: Mus musculus

<400> SEQUENCE: 28

Met Glu Trp Thr Trp Val Phe Leu Phe Leu Leu Ser Val Thr Ala Asp
1               5                   10                  15

Val Gln Ser Gln Val Gln Leu Gln Gln Ser Gly Thr Glu Leu Met Thr
            20                  25                  30

Pro Gly Ala Ser Val Thr Met Ser Cys Lys Thr Ser Gly Tyr Thr Phe
        35                  40                  45

Ser Thr Tyr Trp Ile Glu Trp Val Lys Gln Arg Pro Gly His Gly Leu
    50                  55                  60

Glu Trp Ile Gly Glu Ile Leu Gly Pro Ser Gly Tyr Thr Asp Tyr Asn
65                  70                  75                  80

Glu Lys Phe Lys Ala Lys Ala Thr Phe Thr Ala Asp Thr Ser Ser Asn
                85                  90                  95

Thr Ala Tyr Met Gln Leu Ser Ser Leu Ala Ser Glu Asp Ser Ala Val
            100                 105                 110

Tyr Tyr Cys Ala Arg Trp Asp Arg Leu Tyr Ala Met Asp Tyr Trp Gly
        115                 120                 125

Gly Gly Thr Ser Val Thr Val Ser Ser
    130                 135

<210> SEQ ID NO 29
<211> LENGTH: 396
<212> TYPE: DNA
<213> ORGANISM: Mus musculus

<400> SEQUENCE: 29

```
atggagacag acacactcct gttatgggta ctgctgctct gggttccagg ttccactggt    60
gacattgtgc tgacacagtc tcctgcttcc ttaactgtat ctctggggca agagaccacc   120
atctcatgca gggccagcaa gagtgtcagt acatctggct atagttttat gcactggtac   180
caactgaaaa caggacagtc acccaaactc ctcatctatc ttgcgtccaa cctaccatct   240
ggggtccctg ccaggttcag tggcagtggg tctgggacag acttcaccct caaaatccat   300
cctgtggagg aggaggatgc tgcaacctat tactgtcagc acagtaggga gattccgtac   360
acgttcggag ggggaccaa gctggaaata aacacgg                              396
```

<210> SEQ ID NO 30
<211> LENGTH: 132
<212> TYPE: PRT
<213> ORGANISM: Mus musculus

<400> SEQUENCE: 30

```
Met Glu Thr Asp Thr Leu Leu Leu Trp Val Leu Leu Leu Trp Val Pro
1               5                   10                  15

Gly Ser Thr Gly Asp Ile Val Leu Thr Gln Ser Pro Ala Ser Leu Thr
            20                  25                  30

Val Ser Leu Gly Gln Lys Thr Thr Ile Ser Cys Arg Ala Ser Lys Ser
        35                  40                  45

Val Ser Thr Ser Gly Tyr Ser Phe Met His Trp Tyr Gln Leu Lys Pro
    50                  55                  60

Gly Gln Ser Pro Lys Leu Leu Ile Tyr Leu Ala Ser Asp Leu Pro Ser
65                  70                  75                  80

Gly Val Pro Ala Arg Phe Ser Gly Ser Gly Ser Gly Thr Asp Phe Thr
                85                  90                  95

Leu Lys Ile His Pro Val Glu Glu Glu Asp Ala Ala Thr Tyr Tyr Cys
            100                 105                 110

Gln His Ser Arg Glu Ile Pro Tyr Thr Phe Gly Gly Gly Thr Lys Leu
        115                 120                 125

Glu Ile Thr Arg
    130
```

<210> SEQ ID NO 31
<211> LENGTH: 118
<212> TYPE: PRT
<213> ORGANISM: Artificial
<220> FEATURE:
<223> OTHER INFORMATION: human germline VH exon VH1-2 and JH exon JH6

<400> SEQUENCE: 31

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Tyr Tyr Tyr Tyr Tyr Gly Met Asp Val Trp Gly Gln Gly Thr
            100                 105                 110
```

```
Thr Val Thr Val Ser Ser
        115

<210> SEQ ID NO 32
<211> LENGTH: 118
<212> TYPE: PRT
<213> ORGANISM: Artificial
<220> FEATURE:
<223> OTHER INFORMATION: human germline VH exon VH1-18 and JH exon JH6

<400> SEQUENCE: 32

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Gly Ile Ser Trp Val Arg Gln Ala Pro Gly Gln Gly Leu Glu Trp Met
            35                  40                  45

Gly Trp Ile Ser Ala Tyr Asn Gly Asn Thr Asn Tyr Ala Gln Lys Leu
50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Tyr Tyr Tyr Tyr Gly Met Asp Val Trp Gly Gln Gly Thr
                100                 105                 110

Thr Val Thr Val Ser Ser
        115

<210> SEQ ID NO 33
<211> LENGTH: 113
<212> TYPE: PRT
<213> ORGANISM: Artificial
<220> FEATURE:
<223> OTHER INFORMATION: human germline VL exon B3 and JL exon JK-1

<400> SEQUENCE: 33

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
                20                  25                  30

Ser Asn Asn Lys Asn Tyr Leu Ala Trp Tyr Gln Gln Lys Pro Gly Gln
            35                  40                  45

Pro Pro Lys Leu Leu Ile Tyr Trp Ala Ser Thr Arg Glu Ser Gly Val
50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Trp Thr Phe Gly Gln Gly Thr Lys Val Glu Ile
                100                 105                 110

Lys
```